United States Patent
Eggink et al.

(10) Patent No.: US 11,376,307 B2
(45) Date of Patent: Jul. 5, 2022

(54) COMPOSITIONS AND METHODS OF TREATING CANCER WITH GLYCOMIMETIC PEPTIDES

(71) Applicant: SUSAVION BIOSCIENCES, INC., Tempe, AZ (US)

(72) Inventors: Laura L. Eggink, Scottsdale, AZ (US); J. Kenneth Hoober, Phoenix, AZ (US)

(73) Assignee: Susavion Biosciences, Inc., Tempe, AZ (US)

( * ) Notice: Subject to any disclaimer, the term of this patent is extended or adjusted under 35 U.S.C. 154(b) by 64 days.

(21) Appl. No.: 16/960,267

(22) PCT Filed: Jan. 3, 2019

(86) PCT No.: PCT/US2019/012228
§ 371 (c)(1),
(2) Date: Jul. 6, 2020

(87) PCT Pub. No.: WO2019/136185
PCT Pub. Date: Jul. 11, 2019

(65) Prior Publication Data
US 2021/0069285 A1    Mar. 11, 2021

Related U.S. Application Data

(60) Provisional application No. 62/699,345, filed on Jul. 17, 2018, provisional application No. 62/614,956, filed on Jan. 8, 2018.

(51) Int. Cl.
*A61K 31/7084*    (2006.01)
*A61K 38/08*    (2019.01)
(Continued)

(52) U.S. Cl.
CPC .......... *A61K 38/08* (2013.01); *A61K 31/7084* (2013.01); *A61K 38/10* (2013.01);
(Continued)

(58) Field of Classification Search
CPC .... A61K 31/7084; A61K 38/08; A61K 38/10; A61K 47/55; A61K 47/641; A61K 47/65; C07K 7/06; C07K 7/12
See application file for complete search history.

(56) References Cited

U.S. PATENT DOCUMENTS 7,592,326 B2    9/2009    Karaolis
7,638,127 B2    12/2009    Gengrinovitch

FOREIGN PATENT DOCUMENTS

WO    2012/061113 A2    5/2012
WO    2013/096829 A2    6/2013
(Continued)

*Primary Examiner* — Jeffrey E. Russel
(74) *Attorney, Agent, or Firm* — Rodney J. Fuller; Booth Udall Fuller, PLC

(57) ABSTRACT

The present disclosure relates to pharmaceutical compositions comprising a peptide or multivalent polypeptide, and an anti-cancer agent. In some embodiments, the anti-cancer agent is conjugated to the peptide or multivalent polypeptide. The present disclosure also relates to a method of treating cancer or reducing cancer cell proliferation using the peptide or multivalent polypeptide. In some aspects, the peptide or multivalent polypeptide enhances the efficacy of the anti-cancer agent, the targeting of the anti-cancer agent to the cancer cells, or both.

20 Claims, 20 Drawing Sheets
Specification includes a Sequence Listing.

(51) Int. Cl.
*A61K 38/10* (2006.01)
*A61K 47/55* (2017.01)
*A61K 47/64* (2017.01)
*A61K 47/65* (2017.01)
*A61P 35/00* (2006.01)

(52) U.S. Cl.
CPC ............ *A61K 47/55* (2017.08); *A61K 47/641* (2017.08); *A61K 47/65* (2017.08); *A61P 35/00* (2018.01)

(56) References Cited

FOREIGN PATENT DOCUMENTS

| WO | 2015/048477 A1 | 4/2015 | |
|----|----|----|----|
| WO | WO-2016033602 A1 * | 3/2016 | ............ A61K 47/641 |
| WO | WO-2016100679 A1 * | 6/2016 | .............. A61P 37/04 |
| WO | WO-2016175878 A1 * | 11/2016 | .............. A61K 45/05 |
| WO | 2016/100679 A9 | 2/2017 | |

* cited by examiner

1A.
NH$_2$–VQATQSNQHTPRGGGS
NH$_2$–VQATQSNQHTPRGGGS
NH$_2$–VQATQSNQHTPRGGGS
NH$_2$–VQATQSNQHTPRGGGS
svL4
1C.
NH$_2$–NQHTPRGGGS
NH$_2$–NQHTPRGGGS
NH$_2$–NQHTPRGGGS
NH$_2$–NQHTPRGGGS
sv6D
1B.
[(VQATQSNQHTPR-GGGS)$_4$K]$_2$K-NH$_2$     svL4 (MW: 6,826)
[(VQATQS-     GGGS)$_4$K]$_2$K-NH$_2$        svC1 (MW: 3,893)
[(VSNQH-      GGGS)$_4$K]$_2$K-NH$_2$        svD2 (MW: 3,697)
[(NQHTPR-GGGS)$_4$K]$_2$K-NH$_2$              sv6D (MW: 4,369)
FIGs. 1A-1C

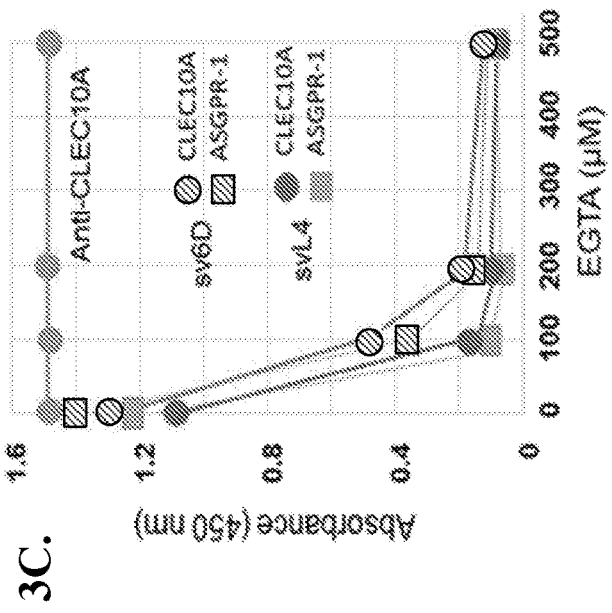
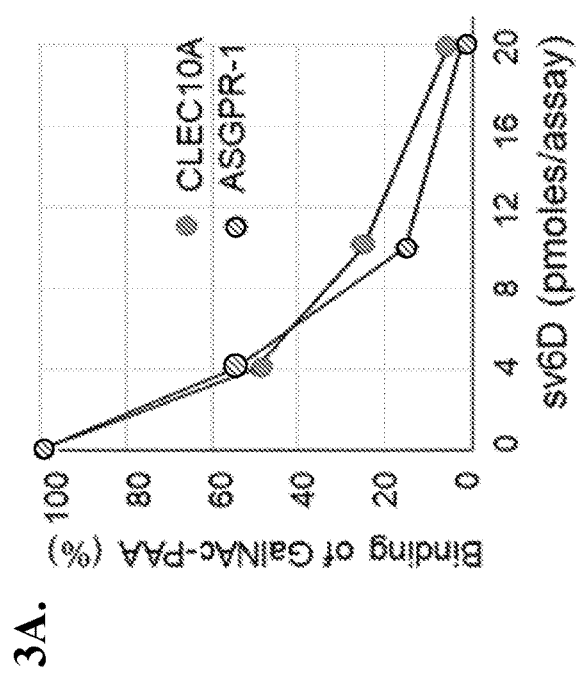
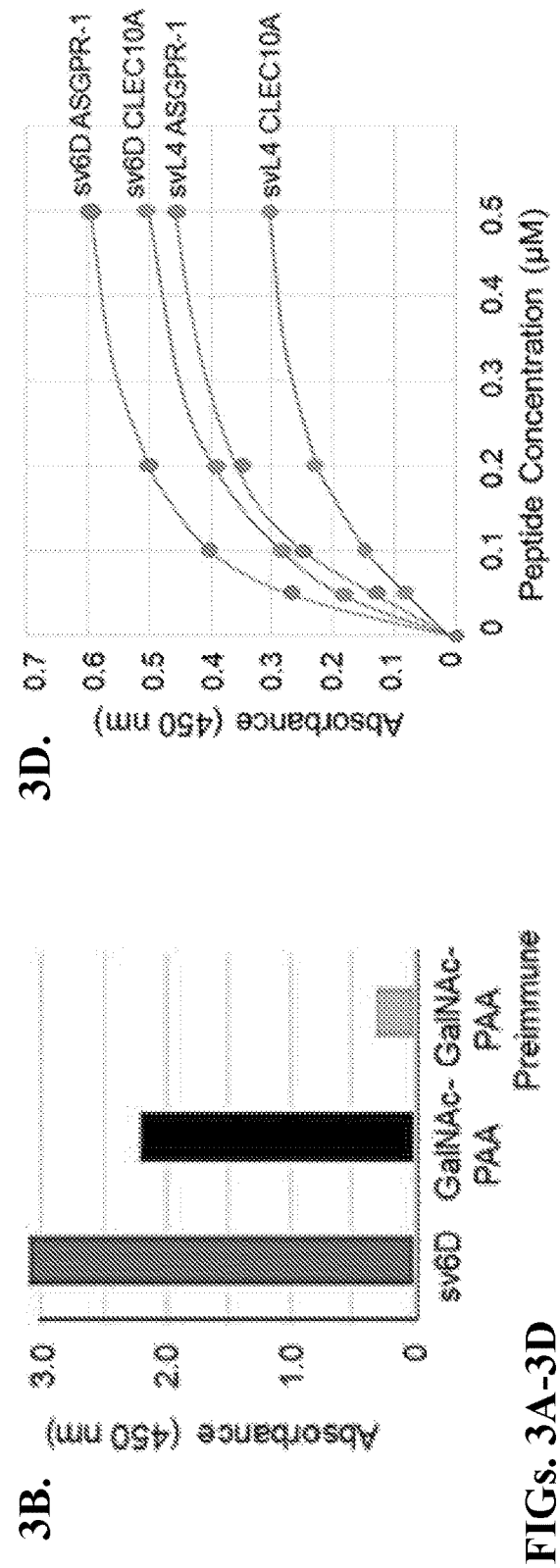
FIGs. 3A-3D

SEQUENCE LISTING

<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 1

Asn Gln His Thr Pro Arg
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 2

Val Gln Ala Thr Gln Ser Asn Gln His Thr Pro Arg
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 3

Gly Gly Gly Ser
1

<210> SEQ ID NO 4
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 4

Gly Gly Gly Ser Gly Gly Gly Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Synthethic Sequence

<400> SEQUENCE: 5

Ser Ser Ser Ser
1

<210> SEQ ID NO 6
<211> LENGTH: 8
<212> TYPE: PRT
<213> ORGANISM: Artificial Sequence

```
<220> FEATURE:
<223> OTHER INFORMATION: Synthetic Sequence

<400> SEQUENCE: 6

Ser Ser Ser Ser Ser Ser Ser Ser
1               5
```

COMPOSITIONS AND METHODS OF TREATING CANCER WITH GLYCOMIMETIC PEPTIDES

CROSS-REFERENCE TO RELATED APPLICATIONS

This application is the U.S. National Stage of International Application No. PCT/US2019/012228, filed on Jan. 3, 2019, which claims the benefit of U.S. Provisional Application No. 62/614,956, filed on Jan. 8, 2018, and 62/699,345, filed on Jul. 17, 2018. The contents of each of which are hereby incorporated herein by reference in their entireties.

INCORPORATION-BY-REFERENCE OF MATERIAL ELECTRONICALLY FILED

Incorporated by reference in its entirety herein is a computer-readable amino acid sequence listing submitted concurrently herewith and identified as follows: One 1,376 byte ASCII (text) file named "Seq_List" created on Feb. 19, 2019.

FIELD OF THE INVENTION

The present invention relates to the fields of compositions comprising therapeutic peptides and their uses in combination with chemo- or immunotherapeutic drugs in a subject for the treatment of cancers.

BACKGROUND

Cancer remains one of the leading causes of death globally. Treatment with therapeutic agents against cancer is often accompanied by a significant level of toxicity because the drugs are administered generally (oral, subcutaneous or intravenous) and exert negative effects on healthy cells. Attempts to diminish toxicity involve injecting drugs directly into tumors, at least when the tumors are palpable. Some cancers do not generate discrete tumors, are more disseminated, or at later stages have metastasized to other sites. Thus, there is a need to selectively target cancer cells, wherever they occur in the body. Additionally, there is a need to enhance endocytosis so that anti-cancer agents can be delivered at much lower concentrations to reduce toxicity, cost, and accumulate efficiently in tumors.

Another major drawback in cancer therapeutics is drug resistance. For example, Paclitaxel is currently used as a chemotherapeutic drug that acts by stabilizing microtubules and arresting cells in the cell cycle at the G2/M boundary [95, 96]. Inhibition of cell division prevents growth of the tumor, but effectiveness of the drug gradually dissipates as it is excreted from the body. Paclitaxel is often combined with a platinum-based drug that binds to DNA and blocks replication [97, 98]. Patients treated with these drugs experience a significant level of toxicity. Repeated dosing leads often to resistance to the drugs. Most, if not all, cancer therapies benefit from use of a combination of two or more drugs, usually with different modalities (e.g., [139]). Thus, there is a need to combine paclitaxel or other anti-cancer agents with drugs that do not add toxicity.

SUMMARY OF THE INVENTION

According to the present invention, the foregoing and other objects and advantages are attained by therapeutic peptides that are mimetics of the sugar and are effective anticancer agents. The therapeutic peptides are effective as a monotherapy but unexpectedly provide greater efficacy to other anticancer agents such as chemotherapeutic or immunotherapeutic drugs when administered as a combination either separately or together (as a single composition). Further, covalently linking an anti-cancer agent (e.g., a cytotoxic drug) to the peptide and administer the conjugate as a single molecule confers the particular benefit of targeting the anti-cancer agent to specific tumor cells.

In accordance with an aspect of the invention, the present invention provides a pharmaceutical composition comprising a therapeutic peptide, an anti-cancer agent, and a pharmaceutically acceptable carrier, wherein the peptide and the anti-cancer agent are conjugated, for example via a linker. In accordance with another aspect of the invention, the present invention provides a pharmaceutical composition comprising a therapeutic peptide, an anti-cancer agent, and a pharmaceutically acceptable carrier, wherein the peptide and the anti-cancer agent are not conjugated.

In accordance with another aspect of the invention, the present invention provides a method of reducing cancer cell proliferation. In a first embodiment, the method comprises contacting the cancer cell with the pharmaceutical composition in an amount sufficient to reduce cancer cell proliferation. In one particular implementation, the peptide and the anti-cancer agent are conjugated, e.g., via a linker. In another implementation, the peptide and the anti-cancer agent are not conjugated. In a second embodiment, the method comprises contacting the cancer cell with an anti-cancer agent, and contacting the cell with a therapeutic peptide, wherein the anti-cancer agent and the therapeutic peptide are in amounts sufficient to reduce cancer cell proliferation.

In accordance with another aspect of the invention, the present invention provides a method of treating cancer in a subject in need thereof. In a first embodiment, the method comprises administering to the subject the pharmaceutical composition in an amount sufficient to slow cancer progression in the subject. In one implementation, the peptide and the anti-cancer agent are conjugated. In another implementation, the peptide and the anti-cancer agent are not conjugated. In a second embodiment, the method comprises administering to the subject an anti-cancer agent and administering to the subject a therapeutic peptide, wherein the anti-cancer agent and the therapeutic peptide are in amounts sufficient to slow cancer progression in the subject.

In one embodiment, the therapeutic peptide comprises a sequence of $X_1$-$X_2$-$X_3$-$X_4$-$X_5$-$X_6$-$X_7$-$X_8$, wherein $X_1$ is H or N; $X_2$ is P or Q; $X_3$ is S or H; $X_4$ is H, T, or L; $X_5$ is P, K, or is absent; $X_6$ is R, L, S, or is absent; $X_7$ is S, L, or is absent, and $X_8$ is G or is absent. In another embodiment, the therapeutic peptide comprises a construct having a central framework, a linker sequence, and at least two arms, wherein each arm consists of a core sequence of $X_1$-$X_2$-$X_3$-$X_4$-$X_5$-$X_6$-$X_7$-$X_8$, and each arm is linked to the central framework via the linker sequence, wherein $X_1$ is H or N; $X_2$ is P or Q; $X_3$ is S or H; $X_4$ is H, T, or L; $X_5$ is P, K, or is absent; $X_6$ is R, L, S, or is absent; $X_7$ is S, L, or is absent, and $X_8$ is G or is absent. In a further embodiment, $X_1$ is N, $X_2$ is Q, $X_3$ is H, $X_4$ is T, $X_5$ is P, $X_6$ is R, or combinations thereof. In one embodiment, $X_1$-$X_2$-$X_3$-$X_4$-$X_5$-$X_6$-$X_7$-$X_8$ is NQHTPR (SEQ ID NO: 1). In another embodiment, the sequence or the core sequence is VQATQSNQHTPR (SEQ ID NO: 2).

In one aspect, the therapeutic peptide comprises a sequence of VQATQSNQHTPR (SEQ ID NO: 2) or a construct having a central framework, a linker sequence, and at least two arms, wherein at least arm comprises VQATQSNQHTPR (SEQ ID NO: 2), and each arm is linked to the central framework via the linker sequence, and the peptide and the anti-cancer agent are conjugated. In a particular embodiment the peptide and anti-cancer agent are conjugated via a linker.

In another aspect, the construct comprises a tri-lysine central framework and four arms, and at least one linker sequence is selected from the group consisting of: GGGS (SEQ ID NO: 3), GGGSGGGS (SEQ ID NO: 4), SSSS (SEQ ID NO: 5), and SSSSSSSS (SEQ ID NO: 6).

Preferred peptide has a binding energy (AG') of higher than −35 kJ/mol to CLEC10A, an equilibrium dissociation constant ($K_D$) of 0.01-0.2 µM to CLEC10A, is not antigenic in the subject, or combinations thereof. Preferably, the peptide is in an amount sufficient to trigger endocytosis of CLEC10A into a cell, increase an immune cell population, increase a peritoneal immune cell population, induce release of IFN-γ, or combinations thereof. In another aspect, the amount of the peptide is within the range of 1 nmol to 1,000 nmol per kg of body weight of the subject. In preferred embodiments, the subject is a human.

In one embodiment, the anti-cancer agent is a chemotherapy drug selected from the group consisting of: an alkylating agent, an antimetabolite, an anti-tumor antibiotic, an antiviral drug, a mitotic inhibitor, a topoisomerase inhibitor, and combinations thereof. In a first implementation, the anti-cancer agent is an alkylating agent selected from the group consisting of: busulfan, carboplatin, cisplatin, cyclophosphamide, mitomycin C (MTC), and temozolamide. In a second implementation, the anti-cancer agent is an antimetabolite selected from the group consisting of: 5-Fluorouracil (5-FU, FU), 6-mercaptopurine (6-MP), capecitabine (Xeloda), cytosine arabinoside (AraC), gemcitabine (dFdC), hydroxyurea (HU), and methotrexate (MTX). In a third implementation, the anti-cancer agent is an anti-tumor antibiotic selected from the group consisting of: Bleomycin, dactinomycin (cosmegen), and daunorubicin (cerubidine, rubidomycin). In a fourth implementation, the anti-cancer agent is an antiviral drug selected from the group consisting of: acyclovir (Acy), foscarnet (FOS), and ganciclovir (gan). In a fifth implementation, the anti-cancer agent is a mitotic inhibitor selected from the group consisting of: demecolcine, docetaxel (taxotere), eribulin (halaven), ixabepilone (ixempra), paclitaxel (taxol), and vinblastine. In a sixth implementation, the anti-cancer agent is a topoisomerase inhibitor selected from the group consisting of: camptothecin (CPT), etoposide (VP-16), irinotecan (camptosar), and topotecan (hycamtin).

In yet another embodiment, the anti-cancer agent is a cancer immunotherapy drug selected from the group consisting of: a cellular immunotherapy drug, an antibody therapy drug, a cytokine therapy drug, polysaccharide K, and combinations thereof. In a first implementation, the anti-cancer agent is a cellular immunotherapy drug is selected from the group consisting of: sipuleucel-T (provenge), tisagenlecleucel (kymriah), and axicabtagene ciloleucel (yescarta). In a second implementation, the anti-cancer agent is an antibody therapy drug selected from the group consisting of: an anti-CD20 antibody, an anti-CD52 antibody, an anti-CTLA-4 antibody, an anti-PD-1 antibody, an anti-PD-L1 antibody, and an anti-PD-L2 antibody. In a third implementation, the anti-cancer agent is a cytokine therapy drug selected from the group consisting of: IFNα, IFNβ, IFNγ, IFNλ, and IL-2.

Exemplary anti-cancer agents conjugated to the therapeutic peptide include cyclic dinucleotide (CDN), 5,6-dimethylxanthenone-acetic acid (DMXAA)), doxorubicin, chlorin p6.

The peptide and the anti-cancer agent, in certain embodiments, are conjugated by a chemical conjugation. In a first implementation, the peptide and the anti-cancer agent are conjugated via Lysine amide coupling. In a second implementation, the peptide and the anti-cancer agent are conjugated via Cysteine-based conjugation. In another embodiment, the peptide and the anti-cancer agent are conjugated by an enzymatic conjugation. In a first implementation, the peptide and the anti-cancer agent are conjugated via transpeptidation using sortase. In a second implementation, the peptide and the anti-cancer agent are conjugated via transpeptidation using microbial transglutaminase. In a third implementation, the peptide and the anti-cancer agent are conjugated via N-Glycan engineering. In another embodiment, the linker contains an activated carboxylic acid ester.

In another aspect, the therapeutic peptide further comprises a C-terminal cysteine, the anti-cancer agent comprises a sulfhydryl (—SH) group or an iodo-group, and the cysteine is conjugated to the —SH group or the iodo-group. In another aspect, the therapeutic peptide further comprises a C-terminal carboxyl group, the anti-cancer agent comprises an amino group, and the peptide and the anti-cancer agent are conjugated with a carbodiimide derivative. In another aspect, the therapeutic peptide and the anti-cancer agent are linked with biotin-avidin.

In yet another aspect, the anti-cancer agent and the peptide have an average molar ratio of between 10:1 and 12:1.

In a preferred exemplary embodiment the anti-cancer agent comprises cyclic dinucleotide (CDN), the therapeutic peptide comprises a construct having a central framework, a linker sequence, and four arms, each arm consisting of a core sequence of NQHTPR (SEQ ID NO: 1) and is linked to the central framework via the linker sequence, and the therapeutic peptide and CDN are conjugated via a linker.

In a particular embodiment, the cancer is peritoneal cancer. In additional exemplary embodiments, the cancer is bladder cancer, breast cancer, cervical cancer, hepatocellular carcinoma, Kaposi sarcoma, lung cancer, lymphoma, malignant melanoma, melanoma, mesothelioma, metastatic melanoma lung cancer, non-small cell lung cancer, ovarian cancer, pancreatic cancer, prostate cancer, renal cell cancer, small-cell lung cancer, or squamous lung cancer.

More particularly, in certain embodiments the cancer cells express CLEC10A, ASGPR-1, CLEC4F, or combinations thereof and administration of the anti-cancer agent proceeds the administration of the peptide by at least 1 day, or at least 30 days.

BRIEF DESCRIPTION OF THE DRAWINGS

FIGS. 1A-1C. (FIG. 1A) Structure of tetravalent peptides svL4. (FIG. 1B) Peptides synthesized as subsets of svL4. (FIG. 1C) Structure of tetravalent peptides sv6D.

FIGS. 3A-3D. sv6D as a mimetic of GalNAc. (FIG. 3A) Inhibition by sv6D of binding of multivalent GalNAc-PAA (GlycoTech Corp., Frederick, Md.) to recombinant rat CLEC10A and human ASGPR-1. The reaction mixture included approximately 200 pmoles of biotinylated GalNc-PAA and increasing concentrations of peptide. The figure includes average values from 3 independent experiments. (FIG. 3B) Biotinylated sv6D or GalNAc-PAA were incubated with rabbit antiserum raised against the 6D sequence (NQHTPR) (SEQ ID NO:1) conjugated to keyhole limpet hemocyanin (KLH). Binding was detected with streptavidin-peroxidase conjugate. Similar data were obtained in 2 experiments. (FIG. 3C) Inhibition by EGTA of binding of sv6D (pattern) or svL4 (solid) to CLEC10A and ASGPR-1, respectively. EGTA (1 mM) was added to the final concentrations indicated to assays. Retention of bound CLEC10A was determined by incubation with biotinylated anti-CLEC10A (goat IgG, R&D Systems) and detection with streptavidin-peroxidase conjugate (light grey circle). Similar data were obtained in 3 experiments. (FIG. 3D) Binding of svL4 and sv6D to human recombinant CLEC10A and ASGPR-1 as a function of concentration of peptide in the assay. The figure is representative of 4 separate assays. $K_D$ values±S.D. from reciprocal plots of these data are provided in the text.

(FIG. 4A) In silico docking of an arm comprising sv6D to the carbohydrate-recognition domain of ASGPR-1 (accession number 1DV8) with CABS-dock (RMSD=0.7611 Å) [105]. The peptide is enclosed in shading that delineates the space-filling molecular structure. (FIG. 4B) The structure in (FIG. 4A) as rendered in ArgusLab 4.0.1 (predicted binding energy, ΔG'=−40 kJ/mol). Amino acids in the binding site that interact with the peptide are shown as space-filling structures. The location of the QPD sequence that determines specificity for GalNAc is indicated. (FIG. 4C) The structure of CLEC10A was generated with SWISS-MODEL Deep View [106,107] from the structure of ASPGR-1. Docking was modeled with CABS-dock (RMSD=1.421 Å) and downloaded into ArgusLab 4.0.1 (predicted binding energy, ΔG'=−38 kJ/mol). The binding site and peptide are presented as in (FIG. 4B). Helical and beta-strand secondary structures of the protein are shown as ribbons.

(FIG. 5A) Effect of concentration of sv6D in the medium on release of IFN-γ after 5 days of culture. The figure shows results from an experiment with 3 replicates analyzed by one-way ANOVA, which at 10 nM sv6D, ρ=0.0064. (FIG. 5B) The time course of the appearance of IFN-γ in the medium of cultures incubated with 10 nM sv6D in (FIG. 5A) as compared with control incubations with PBS.

(FIG. 8A) Female C57BL/6 mice were implanted with ID8 ovarian cancer cell line. In this experiment, progression of disease was aggressive, with a median survival of 65 days. Body weights of mice are shown as measured on day 58, after two weeks of alternate-day subcutaneous treatment with sv6D (0.1 nmol/g) or 3 intraperitoneal doses (days 45, 47 and 49) of 18 µg/g paclitaxel in cremophor. Analysis of these data by t test with Welch's correction for unequal variance when applicable indicates ρ=<0.05 for sv6D vs. PBS or no treatment and ρ=<0.05 for paclitaxel vs PBS or no treatment. There was no statistical difference between the effects of paclitaxel and sv6D. (FIG. 8B) Alternate-day injections of sv6D were initiated on day 50 with peptide alone or on day 100 to mice that were previously treated with paclitaxel between day 45 and 49. The figure shows weights of mice on day 121. Analysis of the data set by t test indicated that paclitaxel vs. PBS ρ=<0.05; paclitaxel vs. sv6D was not different, and paclitaxel vs. paclitaxel plus sv6D ρ=<0.05. (FIG. 8C) Kaplan-Meier survival curves for mice treated with paclitaxel, sv6D or a combination of the two in which alternate-day subcutaneous injections of sv6D was started 50 days after paclitaxel treatment. Mantel-Cox log-rank test, $p_{(sv6D/paclitaxel\ vs.\ PBS)}$=<0.0001.

(FIG. 9A) The design of the experiment and extension of survival of C57BL/6 female mice implanted with ovarian cancer cell line ID8 and treatments with anti-PD-1 and sv6D. Anti-PD-1 (rat anti-mouse, clone 29F.1A12) was administered intraperitoneally every other day, 200 µg protein per dose, between day 41 and 49 (white bars). sv6D was administered subcutaneously every other day at 0.1 nmol/g, starting on day 36, 51 or 87 (grey bars). Survival data were analyzed by the Mantel-Cox log-rank test to determine ρ values. (FIG. 9B) Kaplan-Meier survival curves of mice treated with anti-PD-1 and/or sv6D. The figure shows survival of groups 1, 3, 6 and 8. For group 3, the Mantel-Cox log-rank test p=0.003 indicates the significance between treatment with the combination and antibody alone. Anti-PD-1, square; sv6D, dark triangle; anti-PD-1 followed by sv6D (Group 3 in FIG. 9A), light triangle; PBS, circle.

(FIG. 12A) The cyclic dinucleotide, c[G(2',5')p-2'-AHC-A (3',5')p] (CDN, AHC=6-aminohexylcarbamoyl), was conjugated to N-acetylated-sv6D by a carbodiimide reaction. (FIG. 12B) The conjugate delivers the activation factor at much lower concentrations. Human THP1 monocytes, engineered to detect activation of the type 1 IFN pathway (THP1-Dual™ Cells, InvivoGen, San Diego, Calif.), were incubated 20 hours with sv6D in RPMI 1640 medium containing 10% fetal bovine serum after adding the peptide CDN conjugate. The medium was recovered and then incubated with the luciferase detection reagent (Quanti-Luc™, InvivoGen) to assay for luciferase secreted in response to activation of the STING pathway. Photons were detected with a spectrofluorometer. The conjugate was over two orders-of-magnitude more effective than the cyclic dinucleotide alone. The conjugate targets M2 macrophages and tumor cells that express CLEC10A and thus would produce IFN-β within the tumor microenvironment. The STING protein binds CDN with a $K_D$ of about 5 µM [108,109] and thus the conjugate delivers the activation factor at much lower concentrations.

(FIG. 14A) The C-terminal amine group of the N-acetylated derivative of sv6D reacts with the anhydride group of purpurin-18 to link chlorin $p_6$. (FIG. 14B) Fluorescence spectrum of (left) the product of conjugation in ethanol and (right) the spectrum of the original purpurin-18 sample in ethanol. The conjugate will selectively kill tumor cells when injected into a tumor and exposed to red light.

DETAILED DESCRIPTION

Figure 2:
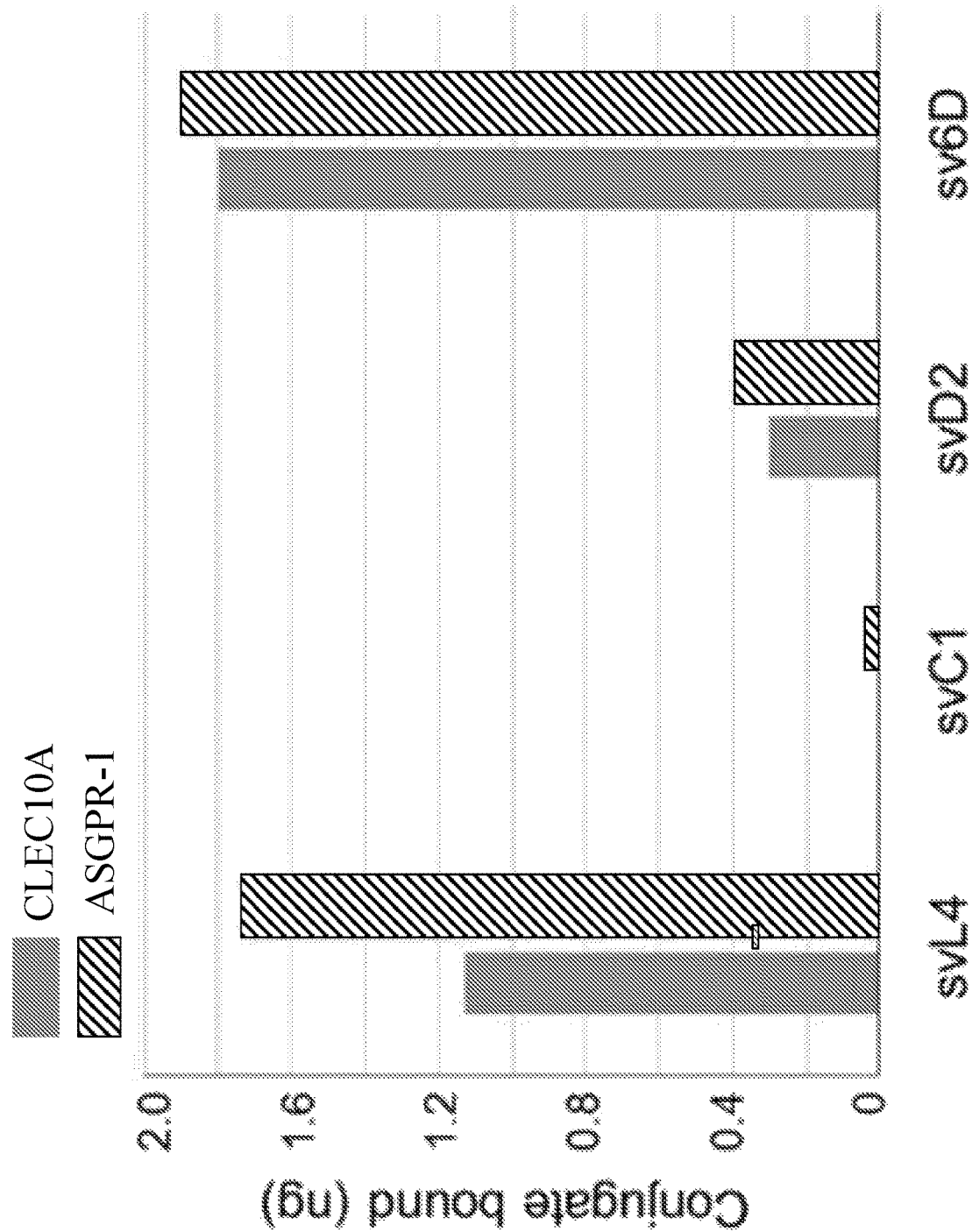
FIG. 2 Binding activity of svL4 and sv6D to $Ca^{2+}$-dependent lectin-type receptor family member 10A (CLEC10A) and Asialoglycoprotein receptor 1 (ASGPR1). Solid-phase binding assays of subsets of svL4 were performed with recombinant human ASGPR-1 (pattern) or CLEC10A (solid). The figure shows representative data from 4 independent experiments.

The technology described herein provides stimulation of the immune system and also allows targeting of cancer cells directly by their expression of the receptor CLEC10A.

Dendritic cells (DCs) and macrophages are powerful antigen presenting cells (APCs) and achieve activation of CD4+ and CD8+ T cells. T cell activation involves presentation of antigens from MEW class I complexes on DCs to antigen-specific receptors (TCR) on CD8+ T cells and/or from MEW class II complexes to antigen-specific TCRs on CD4+ T cells [1]. Sustainable activation of T cells requires two signals presented by DCs, one being the antigen itself that activates the complementary, antigen-specific T cells, and a second, co-stimulatory signal that ensures antigen is non-self and should be destroyed. The second signal is required to sustain viability and activity of T cells and can be provided by a number of factors, such as co-stimulatory receptors on DCs (i.e., CD40, CD80/86) or antibodies against a co-inhibitory factor (i.e., anti-PD-1 or anti-CTLA-4) [2,3]. Factors arising from a diseased state may also provide the necessary signals, which results from phagocytosis and recognition by internal receptors within the late endosome/lysosome compartment. In particular, phagocytosis and degradation of viruses generates oligonucleotide fragments that are rich in CpG sequences that are recognized by TLR9, which initiates a signal that culminates in release of type 1 interferons such as IFNα and IFNβ [4,5]. In addition, appearance of foreign nucleic acids in the cytosol of cells, as would occur with viral infections, triggers the STING pathway, which also results in type I interferon production (see below). But cancer cells can also release suppressive signals and escape the immune system.

CLEC10A as an Immunotherapeutic Target

Peptides are uniquely suited to immunotherapy. Peptides are flexible in design, easily synthesized on a large scale, water soluble, and relatively stable. Although their use as vaccines has a long and successful history, peptides have also been designed that bind selectively to lectin-type receptors with high avidity [1-3 and references therein]. Their use in receptor-mediated immunotherapy is based on their ability to mimic carbohydrate ligands and bind to regulatory, lectin-type, cell-surface receptors expressed by cells of the immune system, with avidities that are orders-of-magnitude greater than endogenous ligands. The interaction of multivalent ligands with multimeric receptors leads to dramatic increases in binding avidity, which decrease the concentration for half-maximal binding to the low nanomolar range.

Some effective anticancer therapies combine complementary drugs that act on different cell types. For example, the currently popular immunotherapeutic drugs are antibodies that block interaction of the inhibitory receptor on T cells, such as cytotoxic T-lymphocyte-associated protein 4 (CTLA-4), the programmed death-1 (PD-1) receptor, or the ligand of PD-1 receptor, PD-L1, which is expressed on many cancer cells. A strategic complement to the antibodies is the ability to activate dendritic cells (DCs) and macrophages with glycomimetic peptides. The potential for C-type ($Ca^{2+}$-dependent) lectins (CLECs) as targets for these peptides rests on the expression of these receptors on cells at strategic points in the immune system and their ability to promote expansion of the innate and adaptive immune systems [4, 5].

CLEC10A (CD301) is a strategic endocytic receptor for immunotherapy of cancer [6-8]. CLEC10A is expressed by DCs, which function at the headwaters of the immune system. C-Type lectin receptors require $Ca^{2+}$ for binding the sugar ligand, both to achieve correct structure of the binding site and coordination with sugar hydroxyl groups [9-12]. CLEC10A (also designated the macrophage galactose-type lectin, MGL) is expressed on dermal DCs, immature peripheral DCs, alternatively-activated M2a macrophages, and other tissues [6, 7, 13-16]. CLEC10A is an endocytic receptor and initiates a primary intracellular $Ca^{2+}$ signal while delivering the ligand to MEW class I and MEW class II antigen processing and presentation pathways [17]. $Ca^{2+}$ and the ligand dissociate from the receptor in early endosomes. The ligand is processed through the MHC class I and II pathways for presentation to T cells; $Ca^{2+}$ is transferred to the cytosol; and the receptor is recycled [17, 18]. An elevation of cytosolic $Ca^{2+}$ is the ubiquitous second messenger [19, 20] involved in stimulation of maturation, migration to lymph nodes, and stimulation of T cells [21, 22].

CLEC10A is a pathogen-recognition receptor that is highly specific for structures that contain terminal N-acetylgalactosamine (GalNAc). The first step in O-glycosylation of cell membrane-bound and secreted glycoproteins occurs in the Golgi by a family of up to 20 distinct UDP-N-acetyl-α-D-galactosamine:polypeptide N-acetylgalactosaminyl-transferases (GALNTs), which attach GalNAc to the hydroxyl group of serine (Ser) or threonine (Thr) [23]. This reaction is essential for the synthesis of larger 0-glycans and the production of mucins, which are major glycoproteins engaged in maintenance of epithelial tissues [24]. An almost universal feature of carcinoma cells is the expression of an aborted 0-glycan, in which only GalNAc is attached to Ser/Thr, a structure known as the Tn antigen [25]. A total of 96 glycoproteins bearing one or more Tn antigens was identified on human T lymphoblastoid cells (Jurkat cell line) and 33 glycoproteins were identified on human breast adenocarcinoma cells (MCF7 cell line) [26]. Antigenicity of the Tn structure was demonstrated in the mouse, and the induced antibodies provided protection against an implanted tumor cell line [27, 28]. Addition of multiple Tn antigens to mucin-derived peptides enhanced immunogenicity and promoted the use of these glycopeptides as vaccines [28-32]. Tumor cells also express the TF antigen (Gal($\beta$1-3Gal-NAc$\alpha$1-O-Ser/Thr) [25, 33]. Whereas the appearance of Tn and TF antigens have been considered the result of incomplete assembly of the typical tri- or tetra-saccharide O-linked glycans, recent evidence suggests that a shift in regulatory pathways driven by membrane trafficking events leads to the shorter glycans on cancer cells [34]. Every person carries antibodies against these antigens, which are present on intestinal microflora, and patients with carcinomas have Tn/TF-sensitive T cells as shown by a delayed hypersensitization reaction [35, 36].

Efficient engagement of CLEC10A requires multivalent ligands such as a fragment of the MUC1 protein bearing 9 Tn moieties [7, 32, 37] or multimeric Tn-peptide structures [28, 38] that provide orders of magnitude greater avidity to the receptor than a single GalNAc residue. An immune response is initiated by internalization of the ligand by trimers of CLEC10A on DCs [39], antigen processing, migration over several days to draining lymph nodes, and subsequent presentation of the antigen to naïve, antigen-specific T cells [40-42]. The structure of the ligand influences the cellular response, with large Tn-bearing glycoproteins trapped in an endolysosomal compartment [32] whereas smaller glycopeptides are further processed in HLAI/HLAII compartments [7, 32].

The type II C-type lectin asialoglycoprotein receptor-1 (ASGPR-1, Ashwell-Morell receptor, CLEC4H1) on hepatic cells also binds GalNAc-containing structures [43, 44]. ASGPR-1 has a 60-fold greater preference for GalNAc over Gal [45]. Each healthy rat hepatocyte expresses 4 to $5\times10^5$ molecules of ASGPR-1 as binding sites for asialo-orosomucoid [46] or $1.8\times10^6$ molecules as determined by an ASGPR-1-targeted antibody [47], which provides a surface concentration for the receptor of 0.8 to 1 µM. Although Gal is the terminal sugar on the multivalent glycans of asialo-orosomucoid [48], the protein binds ASGPR-1 with a $K_D$ of 2 to $7\times10^{-9}$ M [46, 49]. Blood proteins and cells whose bound glycans have lost terminal sialic acid bind ASGPR-1, which internalizes the ligand for degradation [44]. Other major GalNAc/Gal-specific receptors include the type II C-type lectin CLEC4F, which is expressed by Kupffer cells in liver [50]; and the scavenger C-type lectin receptor, with a preference for Gal [51]. The mouse expresses two forms of MGL, MGL1 specific for Gal and MGL2 specific for GalNAc [13]. Human CLEC10A is similar to mouse MGL2, preferentially binds GalNAc, and recognizes terminal GalNAc-containing residues such as the Tn antigen [14].

The highly glycosylated, cell membrane protein CD45, which bears the Tn structure at positions 137 and 140 in exon B of the sequence [26], was identified as an endogenous ligand of CLEC10A/MGL [52]. Although the Tn antigen binds to the receptor with much lower avidity than the mimetic peptides svL4 and sv6D [38], and the affinity of an intact glycoprotein bearing a single sugar ($K_1 \approx 23$ µM [53]) is several orders of magnitude less than that of the peptides, these structures are conceivably competitive inhibitors. CD45 is expressed as several isoforms, with the full-length protein containing exons A, B and C at the extracellular, variable region [54,55]. Binding of CLEC10A to exon B-containing isoforms causes attenuation of T cell activity, apoptosis and immunosuppression [52]. However, activation of T cells leads to expression of shorter isoforms of CD45 such as CD45RO and CD45RA that lack exon B [56-59]. Maturation of DCs leads to down-regulation of CLEC10A [52], which would minimize inhibition by CD45 of T cell activation by activated DCs.

Design of the Invention

Given that natural ligands of CLEC10A that contain GalNAc bind with low affinity and are antigenic, a multivalent peptide mimetic of GalNAc that would bind to CLEC10A was designed. A tetravalent, 12-amino acid peptide sequence, svL4, which emerged from a screen of a phage display library, was previously characterized [60]. svL4 was further refined as a tetravalent structure with the C-terminal 6-mer sequence of svL4, designated sv6D (FIGS. 1B-1C). sv6D retains the binding activity of svL4 and is a more potent stimulator of immune cells. sv6D and svL4 bind to lectins specific for GalNAc with high avidity. Analysis of the sequences of the peptides with MHC binding databases [61,62] predicted that the peptides would not likely be presented by MHC class I or MHC class II molecules in humans or induce production of antibodies. Indeed, no antibodies were detected in mouse sera after alternate-day subcutaneous injections over 3 months. Of importance, subcutaneous injection of the peptides stimulated proliferation and maturation of immune cells in the peritoneal cavity.

CLEC10A expression is upregulated during differentiation of myeloid committed progenitor cells [63]. Possibly, peptide binding to these cells induces proliferation of cells that differentiate into mature, activated immune cells in the peritoneal cavity. Without wishing to be bound by theory, our data support the hypothesis that sv6D and svL4 engage CLEC10A on dermal DCs and immature peripheral DCs and promote cellular maturation. Interaction of T cells with mature DCs within lymphoid tissues leads to their activation. DCs are integral to regulation of the immune system through multi-directional and reciprocal cross-talk, which leads to activation of other types of cells such as NK cells to support innate immunity [64,65]. Effectiveness as an anti-cancer approach is demonstrated by the inhibition of accumulation of ascites in a murine model of ovarian cancer. For example, sv6D dramatically enhanced the efficacy of the chemotherapeutic drug paclitaxel and also the immunotherapeutic drug, anti-PD-1 (FIGS. 8A-8C, 9A-9B).

Figure 5A:
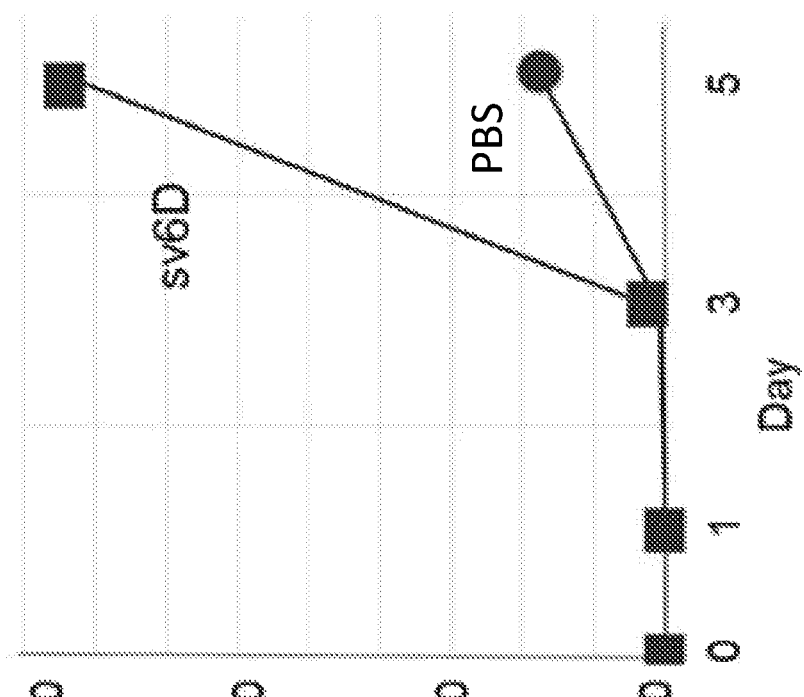
FIGS. 5A-5B. Mixed leukocyte reaction. An allogenic mixture of $5\times10^3$ human monocyte-derived immature dendritic cells and $1\times10^5$ negatively selected CD3$^+$ T cells were incubated with various concentrations of sv6D.
Figure 5B:
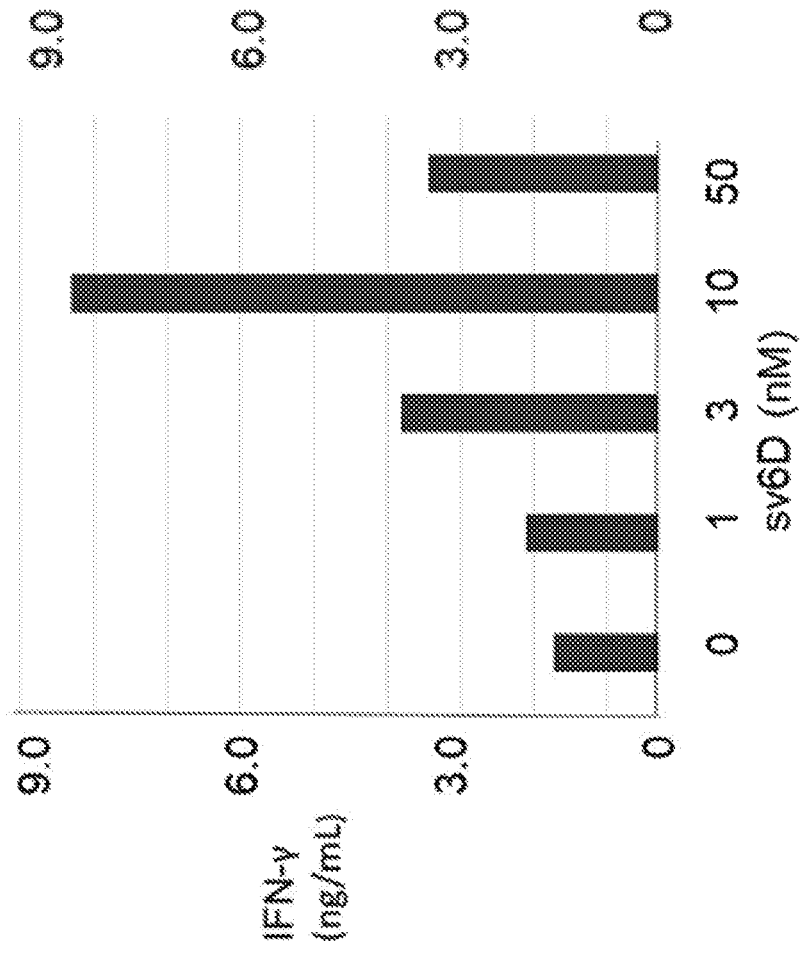

An analysis of lectin-type receptors on human blood DCs and the extent of binding of an array of glycans revealed that prominent among the glycans that bound were those with terminal GalNAc residues [66]. Rapoport et al. evaluated optimal vectors for delivering vaccines to DCs and concluded that MGL (CLEC10A) was a promising target. $IC_{50}$ for binding glycan-PAA conjugates was about 20 µM [66]. Multivalent peptides such as sv6D, however, achieve an optimal cellular response with concentrations near 10 nM (FIG. 5B). Moreover, preliminary data show that sv6D effectively activates T cells against an antigen in vivo.

An endogenous ligand for CLEC10A is the Tn antigen (GalNAc-Ser/Thr), which is rarely found on healthy cells with the exception of the structure on exon B-containing isoforms of CD45, as described above. The Tn antigen, however, is expressed at high levels on carcinoma cells [35,36,67]. Moreover, a large number of cancer cell types have been identified to express CLEC10A [68,69]. Among them are cancer cells of malignant melanoma, bladder, breast, renal, lung squamous, non-small cell lung, small-cell lung, ovarian, hepatocellular carcinoma, pancreatic, and prostate. Expression of the receptor has been detected at the RNA level, and the protein generally appears on the cell surface when expressed. It is expected that the presence of the receptor and the ligand would lead to adhesion of tumor cells and serves a protective function. High-avidity synthetic ligands such as sv6D (FIGS. 1B-1C) may bind the CLEC10A receptor, in turn reduce cell-to-cell adhesion, sensitize the immune system to the Tn antigen, and make the tumor cells more available for destruction. Tumor-associated macrophages (TAM, M2) produce immunosuppressive signals within the tumor microenvironment [15]. High-avidity synthetic ligands can also be used to modify tumor-associated macrophages (M2), either repolarize the macrophages towards a M1 phenotype or eliminate the suppressive cells. The invention herein on targeting of drugs to tumor-associated cells is based on first establishing the specificity of binding of sv6D to receptors, Therefore, the ability to specifically target drugs to the tumor cells, as this invention describes, is an advance in the treatment of cancer.

Interferon-Beta, an Essential Anticancer Cytokine

Interferon-β (IFN-β) is the primary anti-viral and anti-cancer cytokine produced by the endogenous defense mechanism against disease. The first discovery leading to elucidation of the role of IFN-β occurred in 1976 with the observation that interferon treatment of mammalian cells causes inhibition of protein synthesis in the presence of double-stranded RNA (dsRNA) [70]. This finding was followed rapidly by discoveries of 2'-5' oligoadenylate (2-5A), 2-5A synthetases (OAS) and a latent ribonuclease, RNase L [70-72]. These players became recognized as the primary cellular anti-viral response to an infection [73,74]. When an RNA-containing virus is uncoated in the cytosol, the dsRNA activates OAS, which converts ATP to 2-5A. RNase L is activated by dimerization, which occurs upon 2-5A binding. The activated nuclease cleaves dsRNA, which blocks replication of the virus. In addition, cellular RNAs are also degraded, which inhibits protein synthesis and eventually causes apoptosis [75]. However, in the process, short RNA fragments induce expression of IFN-β through the RNA helicases RIG-1 and MDA5, the adapter IPS-1 and transcription factors IRF-3 and NF-κB [76,77]. IFN-β is secreted by the infected cell and binds to its receptor on adjacent cells, which leads to upregulation of expression of OAS and enhances sensitivity of neighboring cells to a viral replication. The enhanced sensitivity to infection results in more rapid apoptosis, thereby blocking spread of the infection.

Whereas the RNase L/OAS pathway protects cells from foreign RNAs, in particular viral dsRNAs, protection against dsDNA is provided by cyclic GMP-AMP (cGAMP) synthase (cGAS) and Stimulator of INterferon Genes (STING) [78-80]. STING is a 379 amino acid protein associated with the endoplasmic reticulum. The first report of STING as an essential innate immune regulator appeared in 2008 [81], and the role of cGAS was established in 2011 [82]. dsDNA binds to cGAS in the cytosol, which in the presence of GTP and ATP, synthesizes cGAMP. A molecule of cGAMP binds to a dimer of STING on the ER [83], which initiates relocation to the perinuclear region in a complex with TANK-binding kinase 1 (TBK1). Phosphorylated TBK1 subsequently phosphorylates IRF3 and NF-κB, which translocate into the nucleus and activate transcription of immune genes including genes for type 1 IFNs and inflammatory cytokines [79]. An innate immune response by cGAS is likely triggered by DNA damage, either through radiation [84] or chemotherapy drugs. The resulting activation of STING and release of type 1 interferons promote maturation and antigen presentation by DCs [80]. Phagocytosis of tumor cells can also trigger STING-dependent cytokine production, which facilitates activation of $CD8^+$ CTLs and other adaptive immune cell responses [79,85]. The STING-dependent antitumor immunity was dependent on type 1 IFNs produced in the tumor microenvironment [83,86].

Both the 2-5A/RNase L and STING/cGAS pathways require type 1 IFN induced through the action of the interferon regulatory factor IRF3 [77,85,86]. The primary mediator of the therapeutic effects of these pathways is IFN-β. The IFNs block proliferation and induce apoptosis of tumor cells [87]. Side-effects of IFN treatment include flu-like symptoms and, because of the action of IFN, tissue damage may occur at the site of injection. Whereas death of infected or cancerous cells is the ultimate goal of these pathways, it can be costly to the organism. Sustained activation of IFN-β production can cause cells to spiral into a stress response that culminates in apoptosis of the host's immune cells [73].

Photodynamic Therapy

Since the mid-1980's, photodynamic therapy has been developed as a promising anti-cancer approach [88,89]. A derivative of hematoporphyrin was found to be taken up selectively by cancer cells, which caused them to become photosensitive. A limitation of this technology was that hematoporphyrin derivative absorbs light weakly at wavelengths longer than 600 nm. As a result, only tumors that occur on or near the surface of the body is accessible because of the strong absorbance of tissues. Hoober et al. [90] prepared purpurin-18 from chlorophyll and showed that the anhydride form of the compound had a strong absorbance maximum at 695 nm. When the anhydride group was opened by hydrolysis to produce chlorin-$p_6$, the absorbance maximum shifted to 662 nm, a wavelength that would still support photodynamic therapy. These products had an $IC_{50}$ concentration for cell killing at about $10^{-8}$M [90].

More recent developments have explored a variety of long-wavelength dyes with absorbance maxima near 700 nm [91,92]. These dyes effectively photosensitize the killing of cancer cells in red light that can penetrate deeply into the body. Further developments involved conjugation of the dyes to monoclonal antibodies that target tumor cell markers such as HER2 and EGFR.

The invention described herein relates to the use of ligands for CLEC receptors to target specific tumor-associated cells and modulate the immune system. As an example, photosensitizer dyes or cytotoxic drugs can be conjugated with peptides such as sv6D to target tumor cells. With different ligands or frequency/dose of administration, this invention provides the means to achieve an appropriate immune response against diseases.

In the Description, and for the purposes of explanation, numerous specific details are set forth in order to provide a thorough understanding of the various aspects of the invention. It will be understood, however, by those skilled in the art, that the structures, compositions, and methods are sometimes shown or discussed generally in order to avoid obscuring the invention. In many cases, a description of the material and operation is sufficient to enable one to implement the various forms of the invention. It should be noted that there are many different and alternative technologies and treatments to which the disclosed inventions may be applied, and the full scope of the inventions is not limited to the examples that are described below. Unless otherwise defined, all technical and scientific terms used herein have the same meaning as commonly understood by one of ordinary skill in the art to which this invention belongs.

The disclosure relates to pharmaceutical compositions, methods of reducing cancer cell proliferation, and methods of treating cancer in a subject in need thereof. The pharmaceutical composition comprises a therapeutic peptides, an anti-cancer agent, and a pharmaceutically acceptable carrier. The method of reducing cancer cell proliferation, comprises contacting the cell with a therapeutic peptide and contacting the cancer cell with an anti-cancer agent. The method of treating cancer in a subject in need thereof, comprises administering a therapeutic peptide and an anti-cancer agent to the subject.

The verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

In one embodiments, the therapeutic peptide comprises a 5- to 8-amino-acid sequence $X_1$-$X_2$-$X_3$-$X_4$-$X_5$-$X_6$-$X_7$-$X_8$, wherein $X_1$ is H or N; $X_2$ is P or Q; $X_3$ is S or H; $X_4$ is H, T, or L; $X_5$ is P, K, or is absent; $X_6$ is R, L, S, or is absent; $X_7$ is S, L, or is absent; and $X_8$ is G or is absent. In some implementations, $X_1$ is H, $X_2$ is Q, $X_3$ is H, $X_4$ is T, $X_5$ is P, $X_6$ is R, $X_7$ is absent, $X_8$ is absent, or combinations thereof. In non-limiting, preferred implementations, $X_1$ is H, $X_2$ is Q, $X_3$ is H, $X_4$ is T, $X_5$ is P, $X_6$ is R, and $X_7$ and $X_8$ are absent, i.e., the therapeutic peptide comprises NQHTPR (SEQ ID NO: 1). In other implementations, the therapeutic peptide comprises VQATQSNQHTPR (SEQ ID NO: 2).

In preferred embodiments, the peptide is a multivalent structured polypeptide comprising: a construct having a central framework, a linker sequence, and at least two arms, wherein each arm consists of a core sequence of $X_1$-$X_2$-$X_3$-$X_4$-$X_5$-$X_6$-$X_7$-$X_8$, and each arm is linked to the central framework via the linker sequence, wherein $X_1$ is H or N; $X_2$ is P or Q; $X_3$ is S or H; $X_4$ is H, T, or L; $X_5$ is P, K, or is absent; $X_6$ is R, L, S, or is absent; $X_7$ is S, L, or is absent; and $X_8$ is G or is absent. In some implementations, $X_1$ is H, $X_2$ is Q, $X_3$ is H, $X_4$ is T, $X_5$ is P, $X_6$ is R, $X_7$ is absent, $X_8$ is absent, or combinations thereof. In non-limiting, preferred implementations, $X_1$ is H, $X_2$ is Q, $X_3$ is H, $X_4$ is T, $X_5$ is P, $X_6$ is R, and $X_7$ and $X_8$ are absent, i.e., the therapeutic peptide comprises NQHTPR (SEQ ID NO: 1). In other implementations, the therapeutic peptide comprises VQATQSNQHTPR (SEQ ID NO: 2).

As used herein, "construct" is defined as the entire molecule and comprises the central framework linked with the arms. In non-limiting embodiments, the construct comprises the central framework linked to, for example, 2, 3, 4, 5, 6, 7, 8, 9, 10, 11, or 12 arms, preferably 2 to 8 arms. In a preferred embodiment, the construct comprises the central framework linked to 4 arms. Each arm within the construct may consist of the same or different therapeutic sequence and/or linker. Typically, at least one of the multiple arms comprises the peptide sequence $X_1$-$X_2$-$X_3$-$X_4$-$X_5$-$X_6$-$X_7$-$X_8$ as described in the previous paragraph. In one preferred embodiment, the therapeutic sequences are the same between arms. In another preferred embodiment, the therapeutic sequences of each of the arms comprise NQHTPR (SEQ ID NO: 1).

The "central framework" provides a structure for attaching the arms. The central framework is based on a core molecule, which has at least two functional groups to which molecular branches having terminal functional groups are bonded, e.g., a tri-lysine to which the peptide arms are added. Such molecules may be developed or created to present a varying number of branches, depending on the number of monomers branched from the core molecule. Each terminal functional group on each branch provides a means of attachment to an arm. Non-limiting examples of preferred central framework include: ethylenediamine (1,2-ethanediamine), ethylene glycol (1,2-dihydroxyethane), polyols such as glycerol, 3,5-diaminobenzoic acid, 1,3,5-triaminobenzene, and monocarboxylic-diamino compounds of intermediate length. Preferably, the monocarboxylic-diamino compounds are within the range of 2 to 10 carbons in length. Non-limiting examples of such compounds are 2,3-diaminopropionic acid and 2,6-diaminocaproic acid. In a more preferred embodiment, the monocarboxylic-diamino compound is 6 carbons in length. Compounds that provide an aromatic central framework which absorbs light may be beneficial for determining peptide concentration as well. The carboxyl group of the monocarboxylic-diamino compounds allows the addition of C-terminal tags including biotin derivatives. In a preferred embodiment, the central framework comprises a tri-lysine core (a lysine residue as the central molecule bonded to two lysine residues, each through its carboxyl group, to one of the amino groups of the central lysine residue), providing a central framework (tri-lysine central framework) for the arms.

The "arm" comprises the therapeutic sequence, plus the linker sequence. The "linker sequence" comprises a peptide chain or other molecule that connects the central framework to the core sequence. In a preferred embodiment, the linker sequence comprises, but is not limited to, certain linker peptide sequences, polyethylene glycol, 6-aminocaproic acid (6-aminohexanoic acid), 8-aminooctanoic acid, and dextran. In a most preferred embodiment, the linker sequence is GGGS (SEQ ID NO: 3), GGGSGGGS (SEQ ID NO: 4), SSSS (SEQ ID NO: 5), SSSSSSSS (SEQ ID NO: 6), or variations thereof. The length of the linker sequence can be adjusted, for example, the linker sequence GGGS (SEQ ID NO: 3) can be repeated to provide variable lengths, e.g., repeated twice GGGSGGGS (SEQ ID NO: 4), or even three or more times; additional serine residues could be added to SSSS to also produce varying lengths of the linker sequence. In some embodiments, the N-terminal amino group of the "arms" is acetylated to prevent interference in the conjugation reaction.

In some aspects, the peptide and CLEC10A have a binding energy ($\Delta G'$) of higher than −30 kJ/mol, higher than −35 kJ/mol, or higher than −40 kJ/mol. In other aspects, the peptide and CLEC10A have a binding energy (ΔG') of between −20 and −50 kJ/mol, or any other number range in between, e.g., between −20 and −45 kJ/mol, between −25 and −45 kJ/mol, between −25 and −40 kJ/mol, between −30 and −40 kJ/mol, or between −30 and −35 kJ/mol, etc. As is known in the art, the higher the binding energy (ΔG') (the greater the strength of binding), the more negative the binding energy.

In some embodiments, the peptide and CLEC10A have an equilibrium dissociation constant ($K_D$) of 0.001-0.35 μM, or any other number range in between, e.g., 0.001-0.3 μM, 0.002-0.3 μM, 0.002-0.25 μM, 0.005-0.25 μM, 0.005-0.2 μM, 0.01-0.2 μM, or 0.01-0.15 μM, etc. In other embodiments, the peptide and CLEC10A have an equilibrium dissociation constant ($K_D$) of 0.001-0.35 μM, or any other number range in between, e.g., 0.001-0.3 μM, 0.002-0.3 μM, 0.002-0.25 μM, 0.005-0.25 μM, 0.005-0.2 μM, 0.01-0.2 μM, or 0.01-0.15 μM, etc.

In some aspects, the peptide is in an amount sufficient to trigger endocytosis of CLEC10A into a cell. In some embodiments, the peptide is in an amount sufficient to increase immune cell population, for example, peritoneal immune cell population. Non-limiting examples of peritoneal immune cells include: T cells expressing CD3; activated natural killer T (NKT) cells expressing CD3, NK1.1, and CD69; activated natural killer (NK) cells expressing CD3, NK1.1, and CD69; T cells expressing CD4; activated T cells expressing CD4 and CD69; cytotoxic T cells expressing CD8; activated cytotoxic T cells expressing CD8 and CD69; mature, active macrophages expressing CD11b, F4/80, and CD86; dendritic cells (DCs) expressing CD11c; activated DCs expressing CD11c and CD86; B cells expressing CD19; or memory B cells expressing CD19, CD73, CD80, and CD273, etc. In preferred embodiments, the peptide is in an amount sufficient to increase peritoneal immune cells selected from the group consisting of: T cells expressing CD3; activated natural killer T (NKT) cells expressing CD3, NK1.1, and CD69; T cells expressing CD4; cytotoxic T cells expressing CD8; DCs expressing CD11c; activated DCs expressing CD11c and CD86; and combinations thereof.

In some embodiments, the peptide is in an amount sufficient to increase immune cell population by 10-500%, or any percent number in between, e.g., 10-450%, 20-450%, 20-400%, 40-400%, 40-350%, 80-350%, 80-300%, 100-300%, 100-250%, or 150-200%, etc. In other embodiments, the peptide is in an amount sufficient to increase immune cell population by at least 10%, at least 30%, at least 100%, at least 150%, at least 200%, at least 300%, at least 400%, or at least 500%, etc.

In some aspects, the peptide is in an amount sufficient to release IFN-γ. In other aspects, the peptide is in an amount sufficient to repolarize macrophages towards a M1 phenotype, eliminate myeloid-derived suppressor cells (MDSCs), modify tumor-associated macrophages (TAM), or combinations thereof. In further aspects, the peptide is in an amount sufficient to decrease Treg cells, and/or promote maturation of immune cells selected from the group consisting of: macrophages, dendritic cells, CD8$^+$ cytotoxic T cells, and natural killer cells. In yet further aspects, the peptide or the polypeptide is not antigenic in the subject.

In some aspects, the peptide and anti-cancer drug are in amounts sufficient to reduce cancer cell proliferation by at least 5%, at least 10%, at least 15%, at least 20%, at least 25%, at least 30%, at least 50%, at least 75%, or at least 90%, etc. In other aspects, the peptide and anti-cancer drug are in amounts sufficient to reduce cancer cell proliferation by 5-95%, or any percent number in between, e.g., 10-90%, 10-80%, 20-80%, 20-70%, 30-70%, 30-60%, or 40-60%, etc.

In some aspects, the peptide and anti-cancer drug are in amounts sufficient to slow tumor growth by at least 5%, 10%, 15%, 20%, 25%, 30%, 50%, at least 75%, or at least 90%, etc. In other aspects, the peptide and anti-cancer drug are in amounts sufficient to slow tumor growth by 5-95%, or any percent number in between, e.g., 5-90%, 10-90%, 10-80%, 20-80%, 20-70%, 30-70%, 30-60%, or 40-60%, etc.

The term "regulatory T cell" or "Treg cell" as used herein refers to T cells that inhibit T cell responses, particularly by the suppression or down-regulation of effector T cell induction or proliferation. Thus, these cells can induce immunological tolerance. Expression of at least one of CD25, CD39, CD73, and Foxp3 is indicative of regulatory T cells. While the majority of regulatory T cells are CD4$^+$, they may also be CD8$^+$. Another indication of regulatory T cells is high expression of cytotoxic T-lymphocyte associated molecule-4 (CTLA-4) or glucocorticoid induced TNF receptor (GITR).

As used herein, "anti-cancer agent" refers to any drug that is effective in the treatment of malignant, or cancerous, disease. Non-limiting examples of major classes of anti-cancer agents include: alkylating agents, antimetabolites, natural products, or hormones, etc. Non-limiting examples of anti-cancer agents include: a chemotherapy drug, a cancer immunotherapy drug, or a photosensitizer, etc.

As used herein, the term "chemotherapy" refers to the treatment of disease by the use of chemical substances, especially the treatment of cancer by cytotoxic and other drugs. Non-limiting examples of chemotherapy drugs include: an alkylating agent, an antimetabolite, an anti-tumor antibiotic, an antiviral drug, a mitotic inhibitor, or a topoisomerase inhibitor, etc. Non-limiting examples of the alkylating agent include: busulfan, carboplatin, cisplatin, cyclophosphamide, mitomycin C (MTC), or temozolamide, etc. Non-limiting examples of the antimetabolite include: 5-Fluorouracil (5-FU, FU), 6-mercaptopurine (6-MP), capecitabine (Xeloda), cytosine arabinoside (AraC), gemcitabine (dFdC), hydroxyurea (HU), or methotrexate (MTX), etc. Non-limiting examples of the anti-tumor antibiotic include: Bleomycin, dactinomycin (cosmegen), or daunorubicin (cerubidine, rubidomycin), etc. Non-limiting examples of the antiviral drug include: acyclovir (Acy), foscarnet (FOS), or ganciclovir (gan), etc. Non-limiting examples of the mitotic inhibitor include: demecolcine, docetaxel (taxotere), eribulin (halaven), ixabepilone (ixempra), paclitaxel (taxol), or vinblastine, etc. Non-limiting examples of the topoisomerase inhibitor include: camptothecin (CPT), etoposide (VP-16), irinotecan (camptosar), or topotecan (hycamtin), etc.

The term "immunotherapy" as used herein refers the treatment of a disease or condition by inducing, enhancing, or suppressing an immune response. Non-limiting examples of the cancer immunotherapy drug include: a cellular immunotherapy drug, an antibody therapy drug, a cytokine therapy drug, or polysaccharide K, etc. Non-limiting examples of the cellular immunotherapy drug include: sipuleucel-T (provenge), tisagenlecleucel (kymriah), or axicabtagene ciloleucel (yescarta), etc. The term "immune checkpoint" as used herein refers to an inhibitory pathway in the immune system that is crucial for maintaining self-tolerance and modulating the duration and amplitude of physiological immune responses in peripheral tissues in order to minimize collateral tissue damage.

Non-limiting examples of antibody therapy drugs include: an anti-CD20 antibody, an anti-CD52 antibody, an anti-CTLA-4 antibody, an anti-PD-1 antibody, an anti-PD-L1 antibody, or an anti-PD-L2 antibody, etc. Non-limiting examples of cytokine therapy drugs include: IFNα, IFNβ, IFNγ, IFNλ, or IL-2, etc. Non-limiting examples of anti-CD20 antibodies include: ofatumumab (arzerra), or rituximab (rituxan, mabthera), etc. A non-limiting example of the anti-CD52 antibody is alemtuzumab (campath-1H). Non-limiting examples of the anti-PD-1 antibody include: nivolumab (opdivo), or pembrolizumab (keytruda), etc. Non-limiting examples of anti-PD-L1 antibodies include: atezolizumab (tecentriq), avelumab (bavencio), or durvalumab (imfinzi), etc. A non-limiting example of the anti-CTLA-4 antibody is ipilimumab (yervoy).

The term "pharmaceutically acceptable" as used herein means approved by a regulatory agency of the Federal or a state government or listed in the U.S. Pharmacopeia or other generally recognized pharmacopeia for use in animals, and more particularly in humans The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. Non-limiting examples of the pharmaceutical carriers include: saline, gum acacia, gelatin, starch paste, talc, keratin, colloidal silica, urea, nanoparticle, liposome, cationic liposome, or micelle etc. In addition, other excipients can be used.

"Effective amount" or "therapeutically effective amount" is meant to describe an amount of therapeutic peptide or composition of the present invention effective to modulate the innate and adaptive immune systems and/or treat or prevent a disease in a subject and thus produce the desired therapeutic effect in the subject. Typical compositions and dosage forms may comprise one or more excipients. Suitable excipients are well known to those skilled in the art of pharmacy, and nonlimiting examples of suitable excipients are provided herein. See, e.g., Remington's Pharmaceutical Sciences, 18th ed., Mack Publishing, Easton Pa. (1990).

Non-limiting examples of cancers include: bladder cancer, breast cancer, cervical cancer, hepatocellular carcinoma, Kaposi sarcoma, lung cancer, lymphoma, malignant melanoma, melanoma, mesothelioma, metastatic melanoma lung cancer, non-small cell lung cancer, ovarian cancer, pancreatic cancer, prostate cancer, renal cell cancer, small-cell lung cancer, or squamous lung cancer, etc. Preferably the cancer is peritoneal cancer, such as ovarian cancer.

In some aspects, the unit dosage of the peptide is administered on alternate days, every 3, 4, 5, or 6 days, or on a weekly basis. Single unit dosage forms of the peptide of the invention are suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Non-limiting examples of dosage forms include: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. The peptide is preferably administered via a parenteral route, most preferably, the subcutaneous route. In some aspects, the peptide is administered intravenously.

In certain aspects, the peptide is administered in unit dosage amounts of about 0.1-1,500 nmol per kg body weight of the subject, or any dosage amounts in between, e.g., about 0.2-1,500 nmol/kg, about 0.2-1,400 nmol/kg, about 0.4-1,400 nmol/kg, about 0.4-1,300 nmol/kg, about 0.6-1,300 nmol/kg, about 0.6-1,200 nmol/kg, about 0.8-1,200 nmol/kg, about 0.8-1,000 nmol/kg, or about 1 nmol to 1,000 nmol per kg body weight of the subject. In other aspects, the peptide is administered in unit dosage amounts of about 3 nmol/kg body weight to about 1500 nmol/kg body weight, about 3 nmol/kg body weight to about 1000 nmol/kg body weight, about 3 nmol/kg body weight to about 10 nmol/kg body weight, about 1 nmol/kg body weight to about 1000 nmol/kg body weight, or about 0.1 nmol kg body weight to about 1 nmol/kg body weight. In further aspects, the peptide is administered in a unit dosage amount of less than about 1500 nmol/kg body weight, for example, about 1000 nmol/kg body weight, about 500 nmol/kg, about 100 nmol/kg, about 10 nmol/kg, about 1 nmol/kg, or about 0.1 nmol/kg. In one aspect, the peptide may be administered in unit dosage amounts of about 5 nmol/kg, about 10 nmol/kg, about 15 nmol/kg, about 25 nmol/kg, about 30 nmol/kg, about 50 nmol/kg, about 75 nmol/kg, about 100 nmol/kg, about 225 nmol/kg, about 250 nmol/kg, about 500 nmol/kg, about 750 nmol/kg, about 1 μmol/kg, about 10 μmol/kg, or about 50 μmol/kg.

The unit dosage amount depends on the subject. A routinely-used conversion from the mouse to larger animals and humans is the equivalent surface area. In one preferred embodiment, the subject is a mouse, and sv6D is administered by subcutaneous injection of about 100 nmol/kg (e.g., 90-110 nmol/kg) body weight of the mouse. In a second preferred embodiment, the subject is a rat, and sv6D is administered by subcutaneous injection of about 50 nmol/kg (e.g., 45-55 nmol/kg) body weight of the rat. In a third preferred embodiment, the subject is a dog, and sv6D is administered by subcutaneous injection of about 15 nmol/kg (e.g., 13.5-16.5 nmol/kg) body weight of the dog. In a fourth preferred embodiment, the subject is a human, and sv6D is administered by subcutaneous injection of about 8 nmol/kg (e.g., 7.2-8.8 nmol/kg) body weight of the human.

In some embodiments, the combination therapy of the peptide and the anti-cancer agent are administered separately. In some aspects, the peptide is administered first to prime the immune system before administering the anti-cancer agent. For example, the peptide is administered at least two weeks, at least ten days, at least one week, at least five days, at least three days, or at least one day before the administration of the anti-cancer agent. In other aspects, administration of the peptide is continued after the administration of the anti-cancer agent. In further aspects, administration of the peptide is concurrent to the course of administering the anti-cancer agent. In non-limiting embodiments, the administration of the peptide lasts between about 1 day to 1 year, or any time period in between, e.g., about 1 day to 10 months, about 1 week to 10 months, about 1 week to 8 months, about 1 month to 8 months, about 1 month to 6 months, about 2 months to 6 months, about 2 months to 4 months, or about 3 months, etc.

In some embodiments, the peptide and the anti-cancer agent are administered in a formulation in which the combined drugs can be administered as a single application.

In some aspects, the peptide and the anticancer agent, for example, a photosensitizer dye or a cytotoxic drug are conjugated via a linker. In some embodiments, the peptide and the anti-cancer agent are conjugated by a chemical conjugation. Non-limiting examples of the chemical conjugation include Lysine amide coupling, or Cysteine-based conjugation, etc. As used herein, "Lysine amide coupling" or "Amide coupling" refers to conjugation methods connecting the anti-cancer agent and a solvent accessible epsilon-amino group of lysine residues on the peptide using a linker containing activated carboxylic acid ester. As used herein, "Cysteine-based conjugation" refers to conjugation methods relying on a specific reaction between the sidechain sulfhydryl (—SH) group of a cysteine residues of the peptide and a thiol-reactive functional group installed on the anti-cancer agent. In other embodiments, the peptide and the anti-cancer agent are conjugated by an enzymatic conjugation. Non-limiting examples of the enzymatic conjugation include transpeptidation using sortase, transpeptidation using microbial transglutaminase, or N-Glycan engineering, etc.

In some aspects, the peptide and the anti-cancer agent, for example, a STING ligand (e.g., cyclic dinucleotide (CDN or c[G(2',5')p-2'-AHC-A(3',5')p] AHC=6-aminohexylcarbamoyl, or 5,6-dimethylxanthenone-acetic acid (DMXAA)), a chemotherapy drug (e.g., doxorubicin), or a photodynamic therapy drug (e.g., chlorin p6), etc. are conjugated. In some embodiments, the peptide further comprises a C-terminal cysteine, the anti-cancer agent comprises a sulfhydryl (—SH) group or an iodo-group, and the cysteine is conjugated to the —SH group or the iodo-group. In other embodiments, the peptide further comprises a C-terminal carboxyl group, the anti-cancer agent comprises an amino group, and the peptide and the anti-cancer agent are conjugated with a carbodiimide derivative. In other embodiments, the peptide further comprises a C-terminal amino group, the anti-cancer agent comprises an anhydride or carboxyl group, and the peptide and the anti-cancer agent are conjugated with a carbodiimide derivative. In further embodiments, the peptide and the anti-cancer agent are linked via biotin-avidin interaction. In yet further embodiments, the peptide further comprises a C-terminal lysine attached to a biotin and the anti-cancer agent is a biotin-containing compound, for example, biotin-tagged oligonucleotides that are ligands for TLR9.

As used herein, a "photodynamic therapy drug" refers to a photosensitizer or photosensitizing agent, when exposed to a specific wavelength of light, produces a form of oxygen that kills nearby cells.

In some embodiments, conjugation of the peptide increases the transport of the anti-cancer agent into the cancer cell by at least 100%, 2-fold, 5-fold, 10-fold, 20-fold, 50-fold, 100-fold, 200-fold, or 500-fold. In other embodiments, conjugation of the peptide increases the transport of the anti-cancer agent into the cancer cell by 1-2,000 folds, or any number in between, e.g., 10-2,000 folds, 20-2,000 folds, 20-1,800 folds, 50-1,800 folds, 50-1,500 folds, 100-1,500 folds, 100-1,200 folds, 300-1,200 folds, 300-1,000 folds, or 400-800 folds, etc.

In further embodiments, conjugation of the peptide increases IFN-β production of the STING ligand by at least 100%, 2-fold, 5-fold, 10-fold, 20-fold, 50-fold, 100-fold, 200-fold, or 500-fold. In other embodiments, conjugation of the peptide increases IFN-β production of the STING ligand by 1-2,000 folds, or any number in between, e.g., 10-2,000 folds, 20-2,000 folds, 20-1,800 folds, 50-1,800 folds, 50-1,500 folds, 100-1,500 folds, 100-1,200 folds, 300-1,200 folds, 300-1,000 folds, or 400-800 folds, etc.

In some aspects, conjugation of the peptide reduces the amount of the anti-cancer agent sufficient to reduce cancer cell proliferation or slow cancer progression by at least 30%, at least 50%, at least 70%, at least 80%, at least 90%, at least 95%, at least 98%, at least 99%, at least 99.5%, at least 99.8%, or at least 99.9%, etc. relative to the amount required for an equivalent dose of the anti-cancer agent when not conjugated to the peptide. In other aspects, conjugation of the peptide reduces the amount of the anti-cancer agent sufficient to reduce cancer cell proliferation or slow cancer progression by 20-99.9%, or any percent number in between, e.g., 25-99.9%, 25-99.8%, 30-99.8%, 30-99.7%, 35-99.7%, 35-99.6%, 40-99.6%, 40-99.5%, 50-99.5%, or 50-99%, etc. relative to the amount required for an equivalent dose of the anti-cancer agent when not conjugated to the peptide.

In some embodiments, the anti-cancer agent and the peptide have an average molar ratio of about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, or about 12:1, etc. In other embodiments, the anti-cancer agent and the peptide have an average molar ratio of between 1:10 to 12:1, or any number in between, e.g., between 1:8 to 12:1, between 1:8 to 10:1, between 1:6 to 10:1, between 1:6 to 8:1, between 1:4 to 8:1, between 1:4 to 6:1, between 1:2 to 6:1, between 1:2 to 4:1, or between 1:2 to 2:1, etc.

Preferably, the subject being treated by the methods described herein is a mammal, e.g., mouse, rat, monkey, dog, cat, horse, cow, sheep, pig, and more preferably the subject is human. Preferably, the cancer cells described herein is a mammalian cancer cell, e.g., a mouse cancer cell, a rat cancer cell, a cat cancer cell, a dog cancer cell, a monkey cancer cell, a horse cancer cell, a cow cancer cell, a sheep cancer cell, a pig cancer cell, and more preferably the cancer is a human cancer cell.

In some aspects, the tumor cells express CLEC10A, ASGPR-1, CLEC4F, or combinations thereof.

In most preferred implementations of the compositions or methods, the anti-cancer agent comprises cyclic dinucleotide (CDN), the therapeutic peptide comprises a construct having a central framework, a linker sequence, and four arms, each arm consisting of a core sequence of NQHTPR (SEQ ID NO: 1) and is linked to the central framework via the linker sequence, and the therapeutic peptide and CDN are conjugated, e.g., via a linker.

Example 1. Methods

Synthesis of peptides Functional sequence of svL4 was identified through a screen of a 12-mer phage display library (New England BioLabs, Ipswich, Mass.) with the GalNAc-specific lectin from the snail *Helix pomatia* [60, 111]. The consensus sequence was incorporated into a tetravalent structure based on the concept of avidity of binding to receptors as a function of ligand density and entropic factors [44, 49, 112-114]. Multivalent peptides were synthesized by standard solid-phase chemistry utilizing Fmoc (9-fluorenyl-methoxycarbonyl)-protected amino acids by CBL Biopharma LLC (Patras, Greece). The tri-lysine 'core' was synthesized on the solid-phase resin and extended with the sequence GGS. The 'arms' with C-terminal G were synthesized separately by standard chemistry and condensed in solution with the core [115]. Modifications at the C-terminus consisted of an amide group (no tag) or extensions with ε-biotinyl-lysinyl-amide. The sequence GGGS (SEQ ID NO: 3) was included in the structure as a linker sequence between the mimetic sequence and the tri-lysine core. Derivatives of svL4 were also synthesized to determine whether subsets of the sequence have differing activities. The peptides were purified to greater than 95% by HPLC on an XDB-C8 column using a gradient of 5% to 25% acetonitrile in 0.1% trifluoroacetic acid in water at a column temperature of 60° C. Quality of the synthetic product, including correct synthesis and purity, was assessed by MALDI and ESI mass spectroscopy. Lyophilized peptides were dissolved in 100 mM NaCl, neutralized to pH 5, and adsorbed onto a CM-Sephadex C-25 column (2.5×10 cm). The column was washed with 200 mM NaCl to ensure removal of lipopolysaccharide (LPS) prior to elution of svL4 with 500 mM NaCl. LPS was not detected in the peptide solution eluted from the CM-Sephadex column (<0.01 EU/10 mg peptide). Concentration of the peptide was determined with an experimentally determined extinction coefficient at 210 nm of 22 OD units/mg/ml.

Binding Assays Solid-phase binding assays were performed with streptavidin-, protein A/G-, or Nickel-coated microtiter plates (Pierce). His-tagged and Fc-fusion recombinant receptors (R&D Systems, Minneapolis, Minn.) were reconstituted in PBS. Sufficient receptors were added to wells to saturate the coating. His-tagged receptors were added to each well at a 5-fold excess over the stated capacity of the Ni coating to minimize non-specific binding of the peptide. Wells were washed three times with binding buffer (25 mM Tris HCl, pH 7.4, 150 mM NaCl, 0.05% Tween-20) to remove unbound receptor and 50 µL of 2 µM biotinylated peptide in binding buffer were added and allowed to incubate for 1 h. The wells were washed four times with binding buffer and then incubated with 50 µL of 1 µg/mL streptavidin conjugated with peroxidase (Sigma-Aldrich) for 1 h. The wells were washed five times with binding buffer and 50 µL of peroxidase substrate (1-Step™ Ultra TMB, Pierce) were added. After several minutes to allow color development, the reaction was stopped with 50 µL 1 M $H_3PO_4$ and absorbance was measured at 450 nm. Bound streptavidin was quantitated by the specific activity of peroxidase (absorbance/ng protein conjugate/min) under the conditions of the assay.

Flow Cytometry Healthy C57BL/6 male mice, 10 weeks old, were injected subcutaneously with peptides on alternate days. Peritoneal cells were isolated from mice 24 h after dosing by injecting ice cold PBS (containing 3% FBS) into the peritoneal cavity, gently massaging the abdomen, and then collecting the fluid, which was transferred into $K_2$EDTA-treated tubes for evaluation of specific biomarkers. Cells from three mice in each group were pooled, counted and divided among FACS tubes ($1 \times 10^6$ cells per tube). Cells were washed once in PBS containing 3% FBS, then stained with 0.25 to 1 µg of fluorescently conjugated antibody per $10^6$ cells in 100 µL of buffer as recommended by the manufacturer (Table 1).

Cells were incubated with the antibodies for 30 min at 4° C. in the dark. Following staining, the cells were washed two times with PBS/3% FBS and immediately analyzed with a MACSQuant flow cytometer (Miltenyi Biotech, Inc., San Diego, Calif.). Compensation was performed using single stain tubes for each color present in the analysis as well as an unstained control sample. Collection of flow cytometric data and analysis with FlowJo software, version 10.0.6 (FlowJo, LLC, Ashland, Oreg.) were performed by Biomodels LLC (Watertown, Mass.).

TABLE 1

List of cell surface markers used in this study.

| Antibody | Source | Catalog No. | Cell Type Marker |
|---|---|---|---|
| CD11b-APC | BioLegend | 101212 | Macrophage |
| CD11c-Pacific Blue | BioLegend | 117322 | Myeloid Cell, DC |
| CD11c-VioBlue | Miltenyi | 130-102-797 | Myeloid Cell, DC |
| CD3ε-VioBlue | Miltenyi | 130-102-203 | T Cell |
| CD4-APC | BioLegend | 100412 | $T_H$ Cell |
| CD8α-PE | BioLegend | 100708 | Cytotoxic T Cell |
| CD19-FITC | BioLegend | 115506 | B Cell |
| CD69-FITC | BioLegend | 104505 | Cell Activation |
| CD73-Brilliant Violet | BioLegend | 127215 | B Memory Cell |
| CD80-APC | BioLegend | 104713 | B Cell Activation |
| CD86-APC | BioLegend | 105011 | Cell Activation |
| CD273-PE | BioLegend | 107205 | B Memory Cell |
| F4/80-PE | BioLegend | 123110 | Macrophage |
| Ly6C-FITC | Miltenyi | 130-093-134 | Monocyte |
| NK1.1-APC | Miltenyi | 130-095-869 | NK Cell |

Cytokine assays An allogenic mixed leukocyte reaction was performed with $5 \times 10^3$ human monocyte-derived DCs co-cultured with $1 \times 10^5$ CD3+ T cells in X-VIVO 20 medium (Lonza, Allendale, N.J.) by Astarte Biologics, Inc. (Bothell, Wash.). IFN-γ in the medium was assayed over a period of 5 days with a Meso Scale Discovery assay kit (Meso Scale Discovery, Rockville, Md.). For analysis of a cytokine response in vivo to subcutaneous injection of peptide, 6 to 8-week-old female Balb/c mice were anesthetized with isoflurane and inoculated with $5 \times 10^5$ 4T1 breast cancer cells in the $4^{th}$ mammary fat pad. When tumors reached a volume of at least 500 $mm^3$, animals were randomized into groups of 3 and dosed with either 0.1 or 1.0 nmol/g of svL4. At 4 h post dose, terminal blood was collected from 3 animals per group and prepared for serum. Sera were also collected from healthy Balb/c mice by the same procedure. Changes in the levels of cytokines/chemokines in sera from breast cancer-bearing and healthy mice were analyzed with the mouse L-308 membrane array by RayBiotech, Inc. (Norcross, Ga.) (Table 2).

Markers of lymphocyte and monocyte activation in response to 0.1 nmol/g svL4 in Balb/c mice bearing breast tumors are compared with healthy mice. Sera from three animals were pooled for analysis with an array of 308 soluble factors. (When the control value was negligible or low, the fold increase for treated samples appears high).

TABLE 2

Ratios of the levels of selected cytokines in sera (treated vs. untreated animals)

| Cytokine | Breast Cancer | Expression | Healthy |
|---|---|---|---|
| sHVEM | 2 | Activated monocytes, lymphocytes | 10 |
| IL-2 | 56 | Activated CD4 T cells | no change |
| IL-12p70 | 3 | Dendritic cells and macrophages | no change |
| IL-17 | High | T helper cells | no change |

TABLE 2-continued

Ratios of the levels of selected cytokines in sera (treated vs. untreated animals)

| Cytokine | Breast Cancer | Expression | Healthy |
|---|---|---|---|
| IL-21 | High | Activated CD4 T cells | no change |
| IL-23 | High | Dendritic cells and macrophages | no change |
| IL-28 | 4.3 | Augments cytotoxic CD8 T cells | no change |
| IL-31 | 3.5 | Activated Th2 T cells | no change |
| IFN-γ | High | Activated lymphocytes | no change |
| IL-27 | 4.5 | Antigen-presenting cells | 0.55 |
| Lymphotoxin-α | 12.5 | Th1 T cells | 0.74 |
| IL-1α | 3 | Activated Macrophages | 0.86 |
| TNFα | 45 | Activated monocytes, macrophages | 0.21 |

Antigenicity Assay The sequence of one arm of svL4 or sv6D was conjugated to keyhole limpet hemocyanin (KLH) and injected into rabbits at two-week intervals (total of 3 injections) (New England Peptide, Inc., Gardner, Mass.). Two weeks after the final injection, sera were prepared. Mice were injected with a peptide every other day over a period of 3 months (total ~45 injections), blood was then collected by cardiac puncture and sera were prepared. Rabbit serum was diluted 1:10, whereas mouse serum was diluted 1:1 or 1:5 with PBS containing 0.05% Tween-20 (PBST). Sera were incubated in microtiter wells coated with protein A/G (Pierce) for 90 min. The wells were washed three times with PBST, and then incubated with 50 μL of 1 μM biotinylated svL4 or sv6D for 1 h. The wells were washed four times with PBST, incubated 1 h with 1 μg/mL streptavidin-peroxidase conjugate, and washed four times with PBST. Peroxidase activity was assayed as above under Binding Assays.

Animals C57BL/6 and BALB/c mice were obtained from Charles River Laboratories (Wilmington, Mass.). Studies of the effects of subcutaneous injection of peptides on populations of peritoneal cells were performed in AAALAC-accredited facilities at Biomodels LLC, Watertown, Mass. Studies with the murine model of ovarian cancer were conducted at the University of Kansas Medical Center, Kansas City, Kans. Cells of an ovarian epithelial cancer line, ID8 [110], were implanted into the peritoneal cavity of female C57BL/6 mice at a dose of $6 \times 10^6$ cells. All animals were weighed at least weekly throughout these studies. Accumulation of ascites was monitored by increase in body weight, and animals were euthanized when end-stage behavior was expressed. No animals were euthanized for any reason unrelated to the cancer prior to termination of the experiment. Kaplan-Meier survival curves were analyzed by the Mantel-Cox log-rank test.

Example 2. Binding to Recombinant Receptors

Solid-phase binding assays were performed with recombinant human receptors. Three variations of the binding assay were used in this study, all of which allowed the arms of the tetravalent peptide to have full flexibility. (i) Biotinylated peptide was bound in microtiter wells coated with streptavidin and incubated with recombinant human receptors. After extensive washing, the bound receptor was measured by peroxidase conjugated to a receptor-specific antibody. (ii) The extracellular domains of receptors, which were fused with the Fc domain of immunoglobulin IgG, were bound in wells coated with protein A/G. Biotinylated peptide was incubated with the receptors and, after extensive washing, bound peptide was measured with streptavidin conjugated with peroxidase. Or (iii), recombinant receptors with a poly-His tag were bound to Nickel-coated wells and incubated with biotinylated peptide. svL4 and sv6D contain His residues (FIGS. 1A, 1C) and can bind to the Ni coating, which was minimized by adding sufficient poly-His-tagged receptor to saturate the Ni coating.

In these assays, svL4 bound to CLEC10A and, as confirmation of GalNAc mimicry, also to ASGPR-1 (FIG. 2A). Although a significant consensus was found for the 12-mer sequence of svL4 in the screen of a phage display library with the GalNAc-specific lectin [60], subsets of the sequence were synthesized to test the activity of the N-terminal and C-terminal halves in comparison with the full-length svL4 (FIG. 1B). As shown in FIG. 2A, the C-terminal half (sv6D) bound as strongly as the full-length sequence to CLEC10A and to ASGPR-1. Retention of the N-terminal half (svC1) was near the level of blank wells. The mid-section of the svL4 sequence (svD2) bound weakly to these receptors.

A survey of other receptors showed that svL4 or sv6D did not bind significantly to CLEC9A, a lectin-type receptor expressed on monocytes and DCs [123]; DC-SIGN, a mannose-specific lectin-type receptor [122,124,125]; or Siglec-1, which is specific for terminal Neu5Ac-Gal/GalNAc-sequences on complex glycans [126,127]. Binding was not detected with CD44, a receptor for hyaluronic acid [128], or IL-4R, a receptor for IL-4 (FIG. 2B). Of the receptors we have assayed thus far, the peptides bound to those specific for GalNAc, which included CLEC4F, a GalNAc-binding receptor expressed by Kupffer cells that is also homologous to ASGPR-1 [50].

To further determine whether sv6D interacts with the actual sugar binding site, the ability of sv6D to compete with GalNAc-PAA for binding was assayed. As shown in FIG. 3A, sv6D inhibited binding of GalNAc-PAA to CLEC10A from rat as well as human ASGPR-1. This experiment suggests that the peptide has an avidity over an order of magnitude greater than that of the multivalent GalNAc-PAA. Further support for the mimicry of sv6D was the finding that an antiserum that was raised in rabbits against the sv6D sequence (NQHTPR) (SEQ ID NO: 1) conjugated to KLH also bound GalNAc-PAA (FIG. 3B).

Binding of sugar ligands to C-type lectins requires $Ca^{2+}$ bound at three or four sites in the protein [10-12,122]. Removal of $Ca^{2+}$ from these sites relaxes the structure of the binding site and causes loss of sugar-binding activity without significant change in the remainder of the protein. Thus, we reasoned that whether the peptides bind to these receptors at the sugar-binding site could be ascertained by chelation of $Ca^{2+}$. Indeed, binding of the peptides was completely inhibited by chelation of $Ca^{2+}$ with low concentrations of EGTA (FIG. 3C).

Double-reciprocal plots of binding curves with CLEC10A or ASGPR-1 vs. concentration provided $K_D$ values of 0.15±0.02 µM and 0.12±0.01 respectively, for sv6D (FIG. 3D). Corresponding values for binding of svL4 to CLEC10A and ASGPR-1 of 0.24±0.04 µM and 0.21±0.03 respectively, were obtained (FIG. 3D). Although multivalency dramatically increases avidity by decreasing the $k_{off}$ rate of binding to receptors [129,130], it has a finite value, which suggests that the equilibrium $K_D$ may be slightly elevated because of the extensive wash steps in the assay. Asialofetuin, a multi-glycosylated protein with an $IC_{50}$=45.6±2.7 µM for ASGPR-1 [49], at 75 µM inhibited binding of svL4 (0.2 µM) to ASGPR-1 by 53%, which is consistent with the determined $K_D$ value.

Example 3. In Silico Modeling of Peptides as Mimetics of GalNAc

Extensive characterization studies demonstrated that the peptide sv6D is a bona fide mimetic of GalNAc. Moreover, sv6D bound strongly to the GalNAc-specific receptors CLEC10A and ASGPR-1 (FIGS. 3A-3D). To investigate further its ability to bind to human GalNAc-specific lectins, in silico molecular modeling was performed. Whereas the crystal structure of CLEC10A has not been reported, that of ASGPR-1 (CLEC4H1) was determined [12]. The extensive homology between CLEC10A and ASGPR-1 allowed generation of a likely structure for CLEC10A with SWISS-MODEL Deep View [106,107]. The CABS-dock modeling program [105] was used to predict whether the peptide would bind to ASGPR-1 and CLEC10A. This method searches for a binding site on the protein without prior assignment and defines the most probable peptide conformation. The docking program accommodated svL4 in the carbohydrate-recognition domain (CRD) in a hair-pin conformation (RMSD=0.868 Å).

Figures 4A, 4B, 4C:
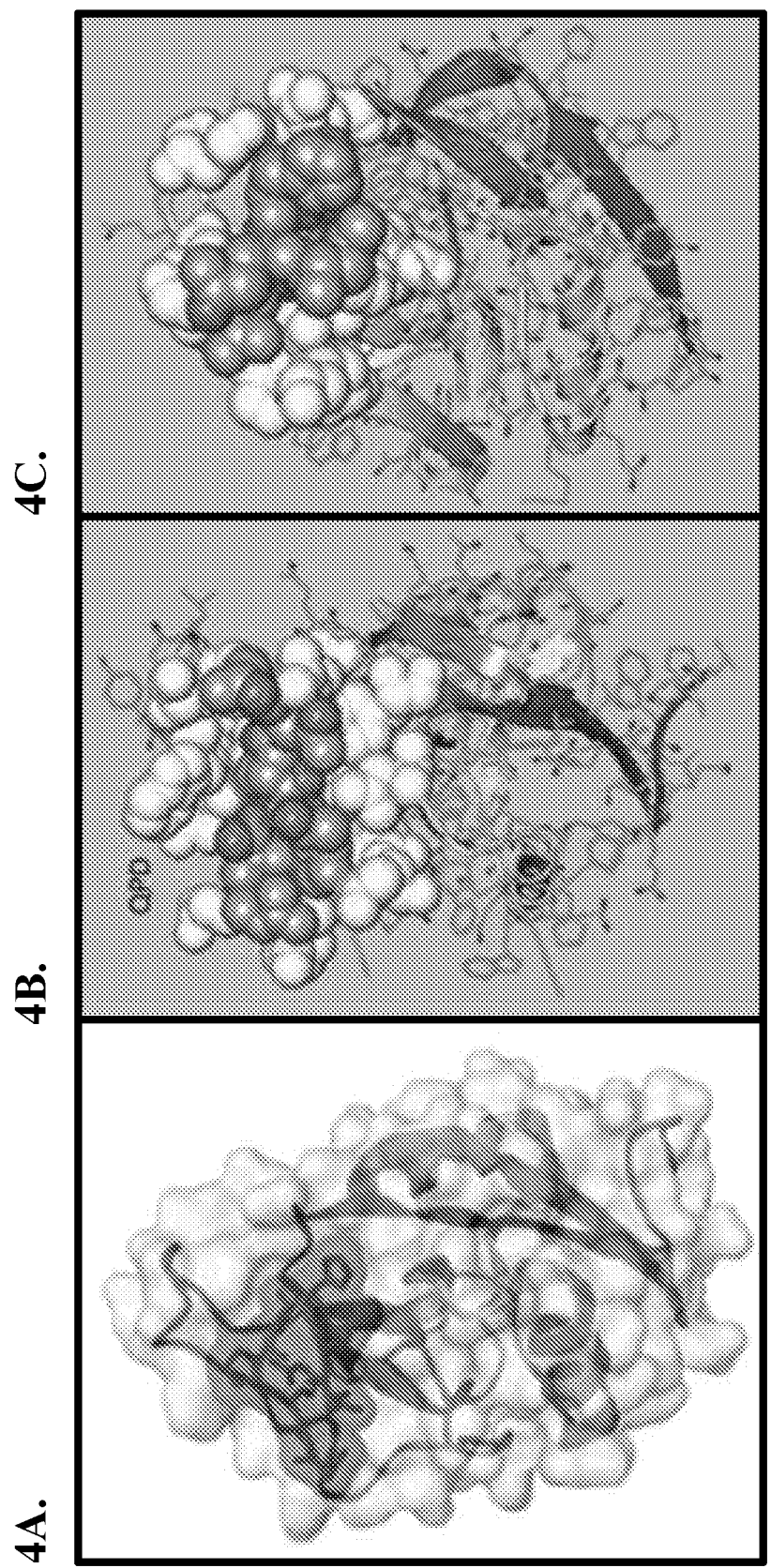
FIGS. 4A-4C. Docking of sv6D to receptors.

As shown in FIG. 4A, the shorter sv6D, with a length dimension approximately two-times that of a sugar residue, was accommodated within the CRD of ASGPR-1. Similar binding predictions were obtained with pepATTRACT [116] and MDockPeP [117], which are blind docking programs that allow the fully flexible peptide to adapt to surface properties of the proteins [118,119].

ASGPR-1, and by homology CLEC10A, has an acidic GalNAc binding site, which may contribute through electrostatic interaction to binding avidity of the positively-charged peptide. The docking programs orient the peptide with the Arg (R) residue near the sequence Gln-Pro-Asp (QPD) that specifies binding of C-type lectins to GalNAc residues (indicated in FIG. 4B) [120,121]. In silico replacement of QPD with Glu-Pro-Asn (EPN), the sequence that has been described as a determinant for binding of mannose, as occurs in the mannose receptor and DC-SIGN (dendritic cell-specific intercellular adhesion molecule (ICAM)-3 grabbing non-integrin, CD209) [122], did not significantly alter the predicted binding of sv6D to CLEC10A. The flexibility of the peptide likely allows interaction of the Arg residue with negatively-charged Asp or the nearby Glu.

The CABS-dock program predicted much weaker binding of sv6D to DC-SIGN (RMSD=4.477 to 7.405 Å compared with 0.7611 to 1.421 Å for ASGPR-1 and CLEC10A) and with significantly lower predicted binding energy. The lack of binding to DC-SIGN, as described below, apparently results from the low homology of the amino acid sequences of the receptors within the CRD. These results suggest that specificity of peptide binding in the CRD is largely provided by the properties of the protein surface, as is typical for most peptide-protein interactions [118]. Although the conformation of the CRD of the GalNAc-specific lectin from *Helix pomatia* is similar to that of C-type lectins [111], the snail lectin lacks a QPD sequence or significant homology to CLEC10A. However, the CABS-dock program indicated an RMSD=1.604 Å for binding of sv6D, with predicted binding energy of $\Delta G'$=−38 kJ/mol.

Example 4. Activation of DCs and T Cells with Peptide

Binding of a peptide to CLEC10A expressed by DCs is expected to stimulate maturation and potential activation of T cells [17]. This hypothesis was tested by an experiment in which human monocyte-derived DCs were co-cultured with T cells. Expression of CLEC10A (CD301) by the DCs was established by flow cytometry. sv6D was added to the medium at various concentrations, and IFN-γ production by T cells was assayed. As shown in FIG. 5A, the maximal amount of IFN-γ was produced with 10 nM sv6D. Significant release of IFN-γ occurred after 3 days of incubation (FIG. 5B), a time required for DC maturation. These results suggest that the optimal concentration of sv6D for an effect on cellular activity is an order of magnitude lower than the $K_D$ obtained from chemical binding assays as in FIG. 3D.

Figure 6:
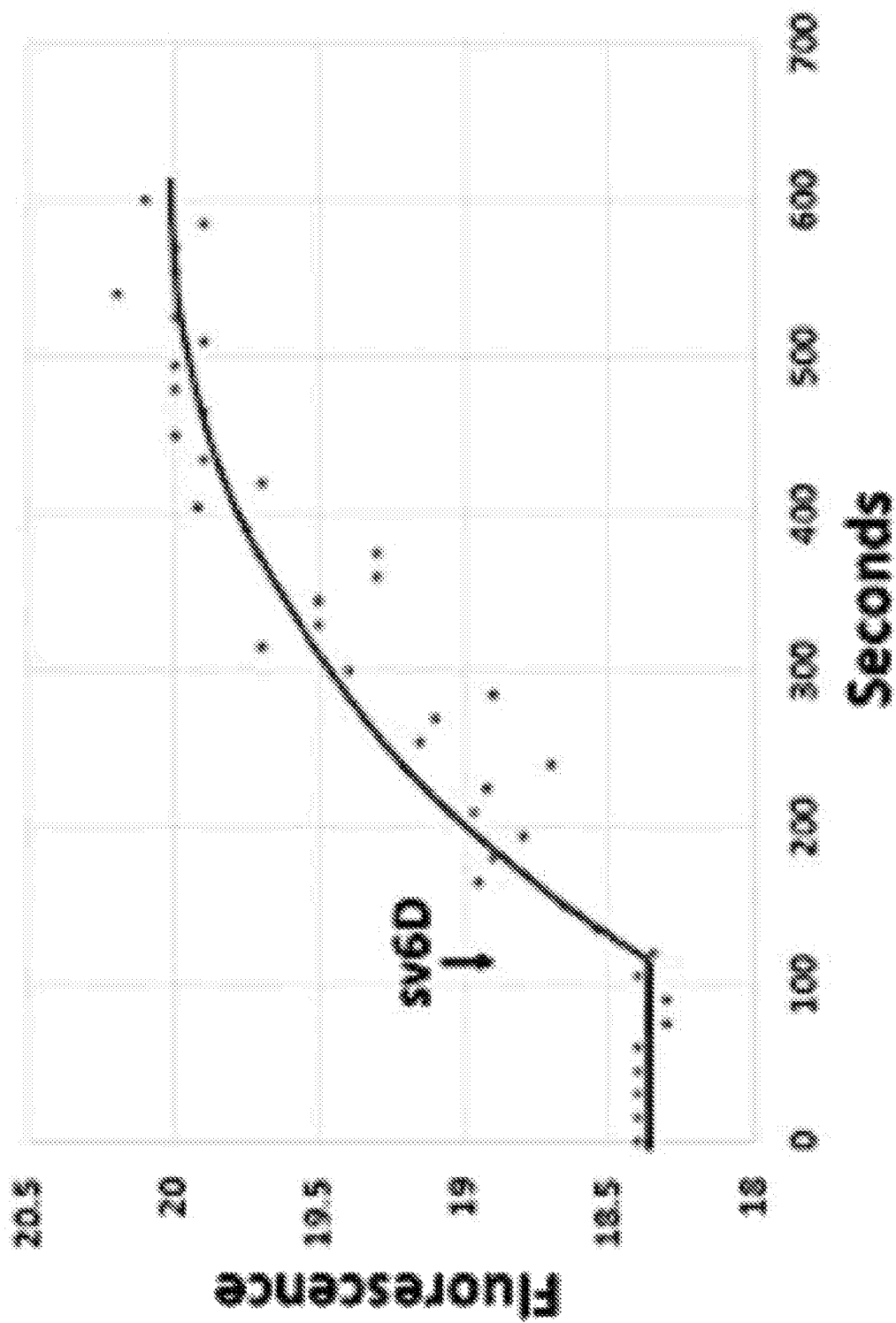
FIG. 6. Peptide-mediated internalization of CLEC10A. Endocytosis of CLEC10A is a mechanism for transporting $Ca^{2+}$ into the cytosol, which activates calcium-dependent phosphatases and kinases through $Ca^{2+}$-calmodulin. Peripheral blood mononuclear cells were incubated at room temperature for 30 min with Fluo-4 AM in the dark. The cells were then irradiated with light of 480 nm for 2 min before adding sv6D to 10 nM. Fluorescence was monitored at 510 nm. The esterified Fluo-4 AM is hydrolyzed in the cytosol and forms a fluorescent chelate with $Ca^{2+}$.
Figure 7A:
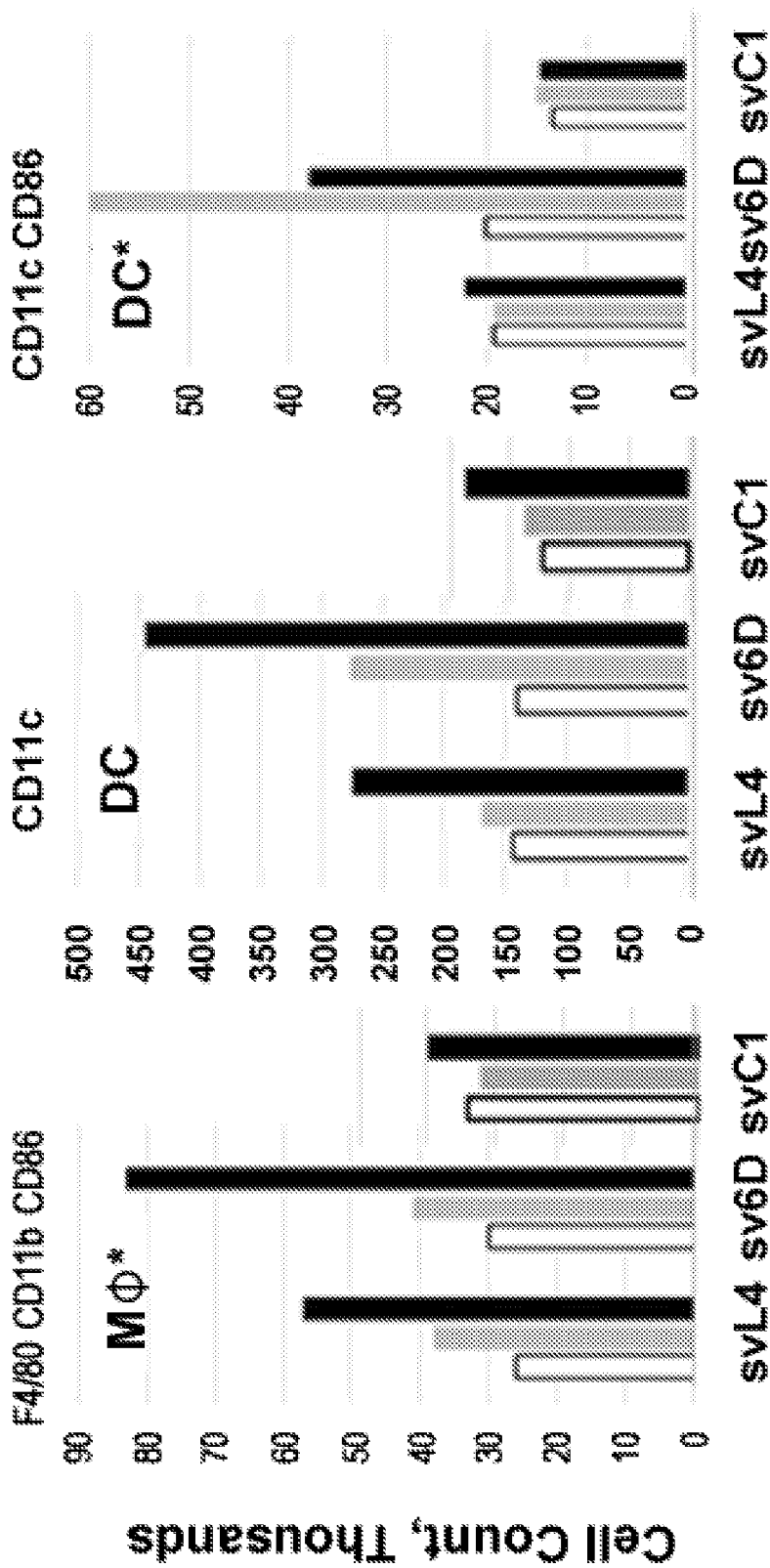
FIGS. 7A-7D. Expansion of peritoneal cells in C57BL/6 mice. Mice were injected subcutaneously at a dose of 1 nmol/g body weight of svL4, sv6D or svC1. Cells in each population recovered in a peritoneal lavage are expressed as cell counts (in thousands). Cells from three mice in each treatment group were pooled for analysis. The number of cells in each population was normalized to the average recovery of total cells from all groups. For each cell type, the left-hand, middle and right-hand set of bars represent samples from mice treated with svL4, sv6D or svC1, respectively. Mice were injected on days 0, 2 and 4, and cells were collected 24 h after each injection. Day 1, open bar; day 3, grey bar; day 5, black bar. Populations that express activation markers are indicated by an asterisk.
Figure 7B:
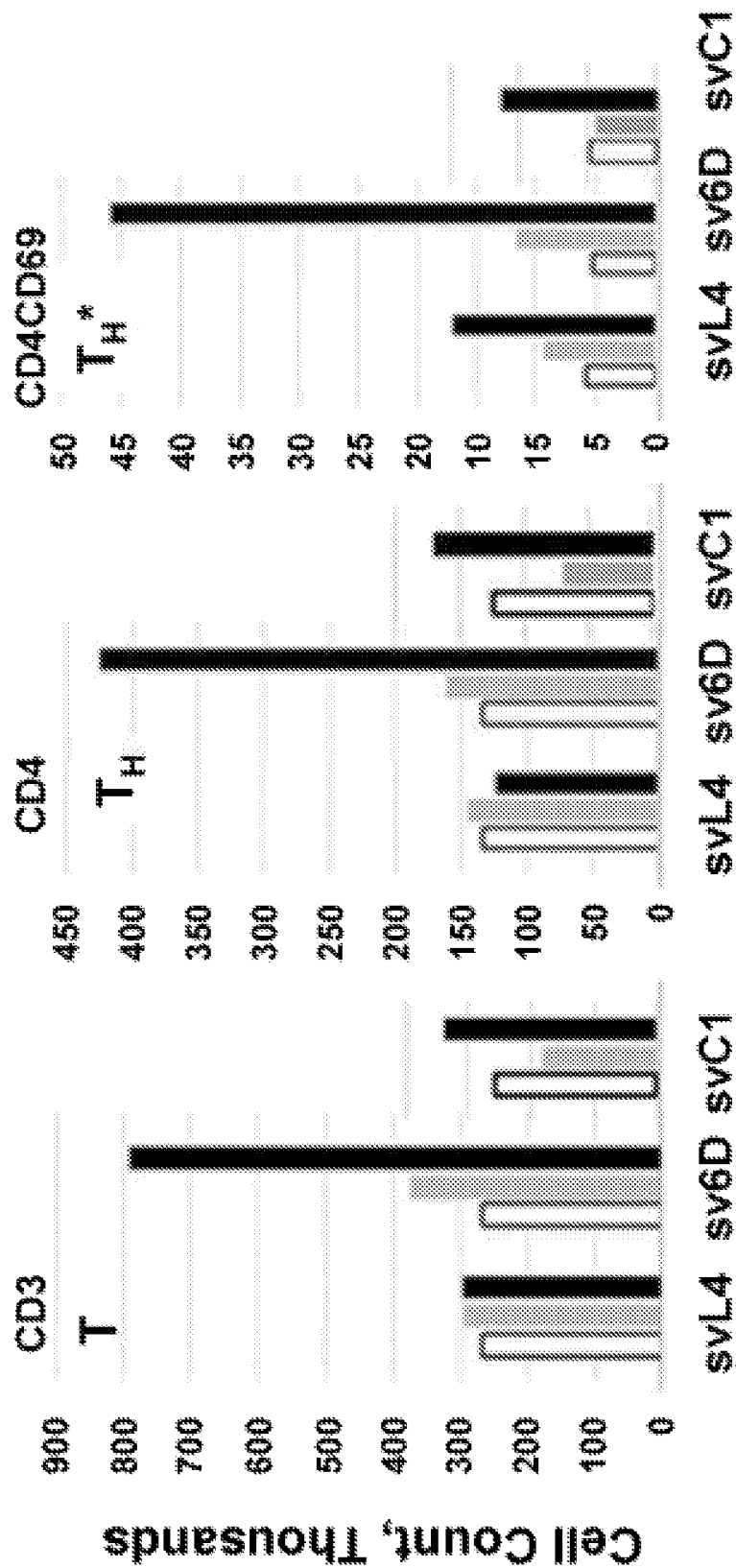
Figure 7C:
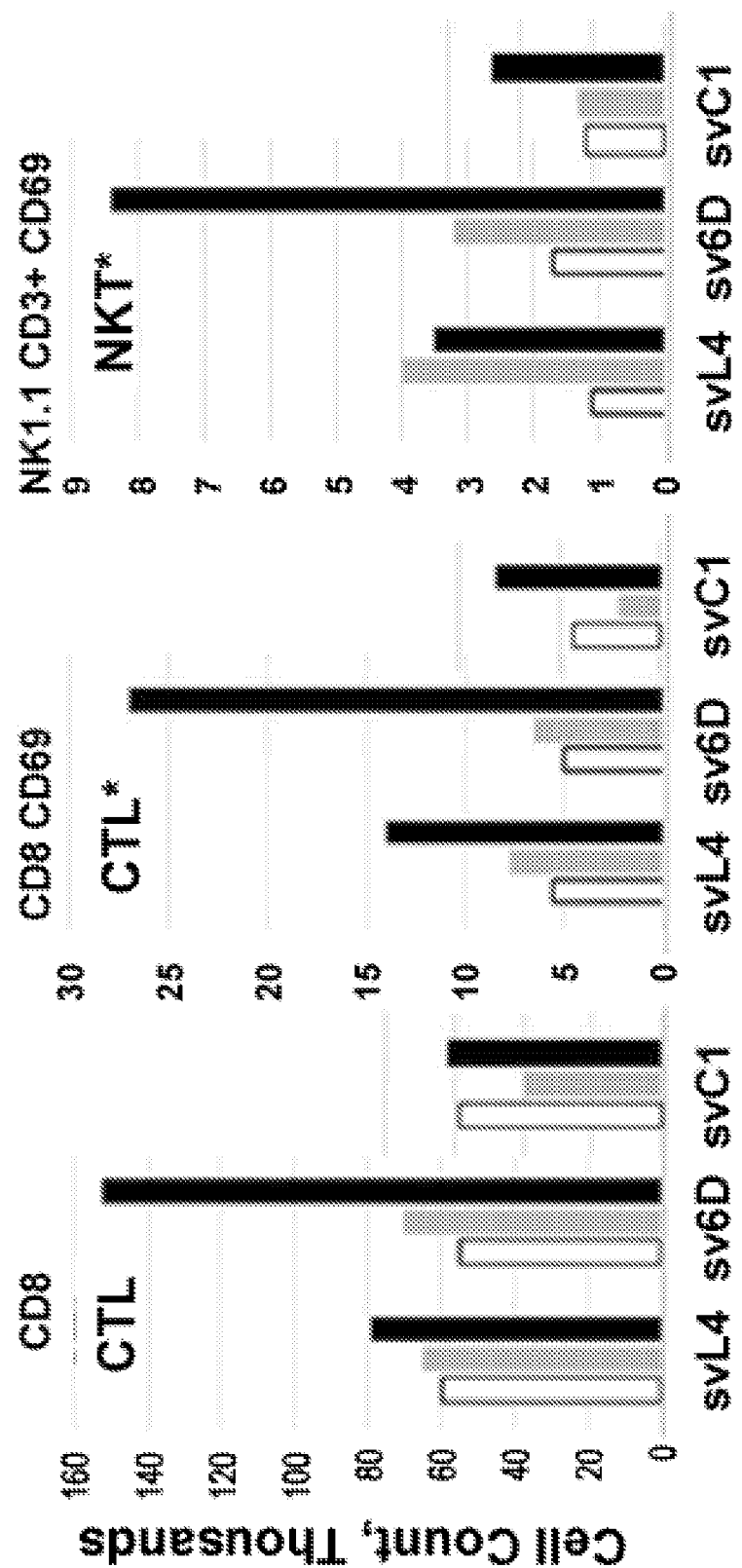
Figure 7D:
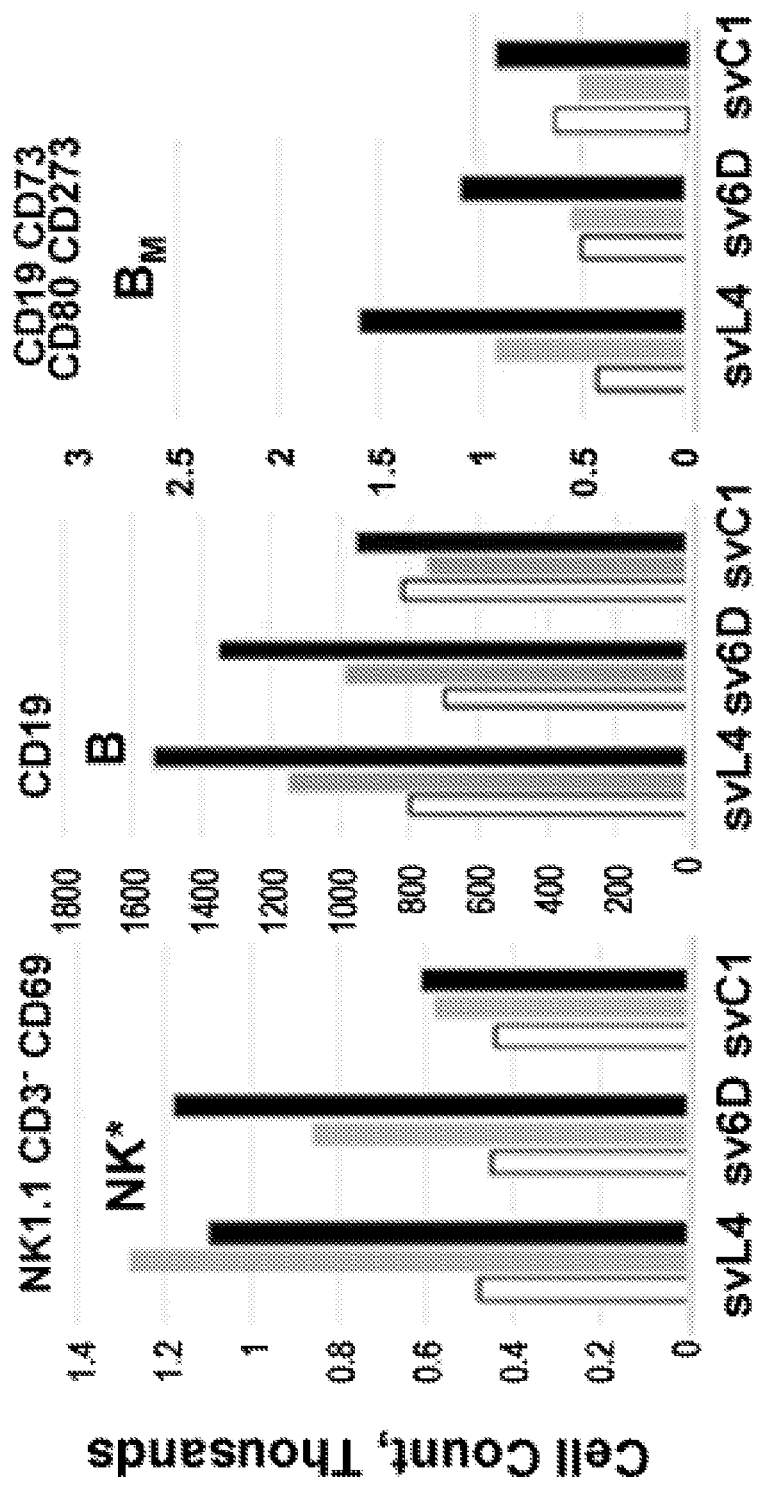

The direct action of sv6D derives from ligand-induced endocytosis of CLEC10A. As shown in FIG. 3C, binding of sv6D to CLEC10A requires $Ca^{2+}$. Internalization of the receptor, which normally exists as a homotrimer, when bound by the multivalent peptide brings the complex into early endosomes (FIG. 6). Extrusion of $Ca^{2+}$ from the endosome and subsequent acidification of the vesicle causes dissociation of the $Ca^{2+}$ ions in the CRD, which are transported into the cytosol and become available for binding by calmodulin [17]. Consequently, $Ca^{2+}$-dependent enzyme activities are activated, including activation of phosphatases such as calcineurin, proteases such as calpain and $Ca^{2+}$/calmodulin-dependent protein kinase kinase β.

Binding of ligands to CLEC10A triggers endocytosis of the receptor and transfer of $Ca^{2+}$ into the cell. Signal transduction pathways are activated by the increase in $Ca^{2+}$ concentration, which leads to activation of phosphatases and kinases [17]. Calcineurin is a phosphatase with broad substrate specificity and requires $Ca^{2+}$ for activity, which offers a facile mechanism for induction of the rapid dephosphorylation of downstream intermediates. Conversely, the $Ca^{2+}$/calmodulin-dependent protein kinase kinase β activates AMP-activated kinase by phosphorylation, which enhances the activity of the protein Stimulator of Interferon Genes (STING) [131,132] Activation of STING leads to expression and release of IFN-β and the anti-infection, anti-cancer, innate immune response. Thus, an influx of $Ca^{2+}$ mediated by a ligand of CLEC10A may support an increase in the production of IFN-β.

Figure 12A:
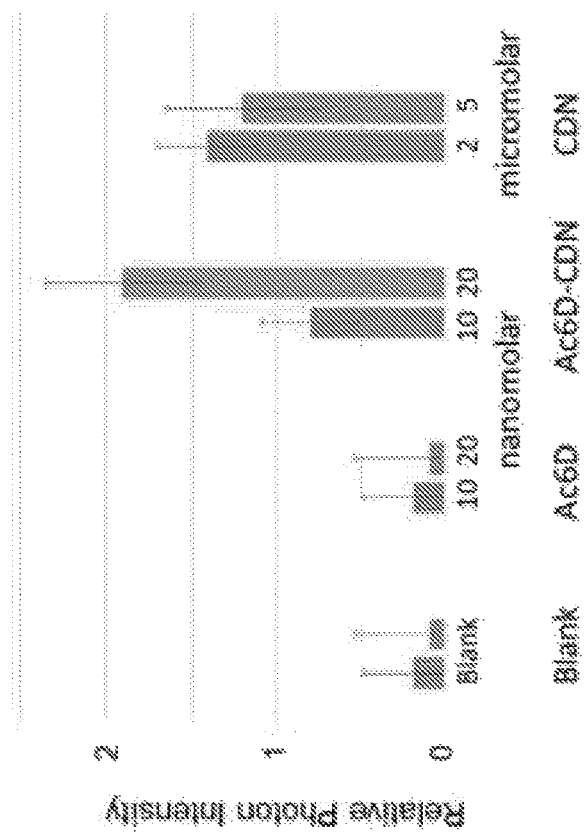
FIGS. 12A-12B. Conjugation with cyclic dinucleotide.
Figure 12B:
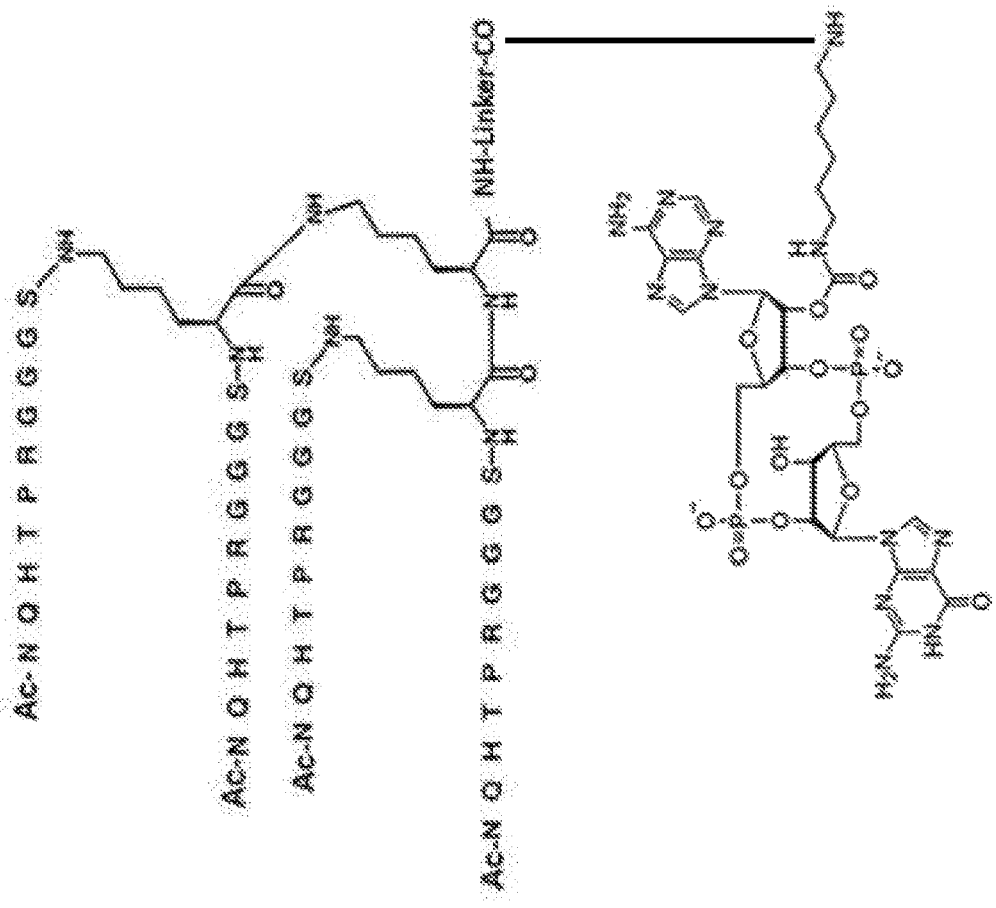
Figure 13:
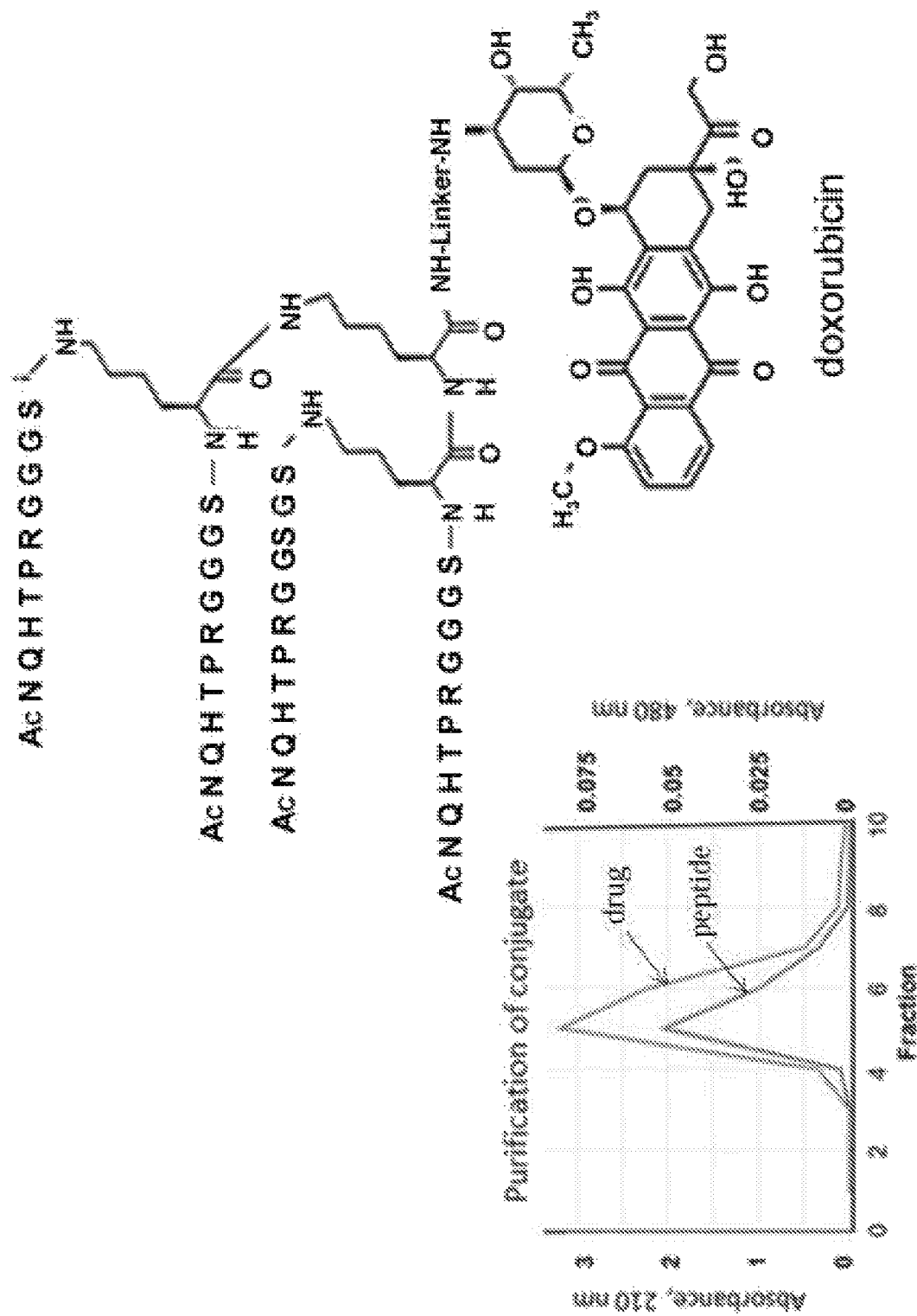
FIG. 13. Conjugation with doxorubicin. N-Acetylated sv6D and doxorubicin were coupled by reaction with glutaraldehyde. The reaction was passed through a Sephadex G-15 gel filtration column, which retained free doxorubicin but allowed the conjugate to pass through as shown by co-elution of peptide and the drug.

The anti-cancer activity of IFN-β has been the subject of intense research [78,79,86]. To determine whether sv6D is capable of activating the STING pathway, human THP1 monocytes that were genetically engineered as reporter cells (InvivoGen, San Diego, Calif.) to express the reporter gene for luciferase under the control of ISG54 (interferon-stimulated gene) promoter were incubated with sv6D and a cyclic dinucleotide (CDN) that is known to bind STING. These cells secrete luciferase into the medium, which can be assayed by a luminescent reaction. As shown in FIG. 12B, micromolar concentrations of the CDN was required to achieve detectable production of light by the reaction.

The ability of sv6D-CDN conjugates to induce activation of the STING pathway for production of type 1 interferons (IFN-α/β) was tested by incubating human THP1 monocytes that were genetically engineered as reporter cells (Invivo-Gen, San Diego, Calif.), with the conjugate. Activation of the STING pathway causes secretion of the enzyme luciferase, which can be assayed in the medium as described by the supplier's instructions. Because the initial steps in this pathway are in the cytoplasm of the cells, access of the cytosol to sv6D is essential, which was demonstrated by the activation of CD8$^+$ T cells illustrated in FIGS. 11A-11B. Luciferase activity was detected in the medium of cultures that were incubated with sv6D-cyclic dinucleotide conjugates at concentrations in the nanomolar range, whereas treatment of cells with cyclic dinucleotides required concentrations in the micromolar range to detect luciferase activity (FIG. 12B). Without wishing to be bound by theory, the primary factor in induction of the pathway at the lower concentrations by the conjugate was likely the receptor-mediated entrance into the cells, whereas the cyclic dinucleotides pass through the cell membrane poorly. The $K_D$ of the STING protein for cyclic dinucleotides is approximately 5 µM [108,109]. However, luciferase was detected in the medium of cells incubated with nanomolar concentrations of sv6D-CDN conjugate. The data suggests that the peptide sv6D is orders-of-magnitude more effective in delivering the activating factor than the natural ligand itself.

Example 5. Responses of Immune Cells in the Peritoneal Cavity of Healthy Mice

To explore their physiological activity in vivo, the peptides were injected subcutaneously into mice. Minimal changes in cell populations were observed in the blood of healthy animals. In contrast, an analysis of total cells in a peritoneal lavage revealed that Balb/c mice contained a large population of small cells (low FSc) with minimal intracellular complexity (low SSc), whereas this population of cells was minimal in C57BL/6 mice. These observations confirm the results of Festing et al., [133] that peritoneal cells in Balb/c mice expressed a high 'lymphocyte' to 'macrophage' ratio whereas the reverse occurs in C57BL strains. Within 24 h after injection of peptide, the population of small cells largely disappeared in Balb/c mice but increased in C57BL/6 mice. Attempts to identify these cells suggested that they comprise a myeloid progenitor population whose proliferation is highly responsive to treatment with the peptide.

To examine whether increases occurred in mature immune cells, peritoneal cells from Balb/c and C57BL/6 mice were analyzed by flow cytometry after cells were stained with the markers listed in Table 1. Several-fold increases in macrophages, DCs, T cells and natural killer (NK) cells were found 24 h after a single injection of svL4 (1 nmol/g) into Balb/c mice but a significant increase occurred only after the second injection into C57BL/6 mice. To explore this observation more extensively, svL4 or sv6D was injected into C57BL/6 mice on day 0, 2 or 4. Peritoneal cells were examined by flow cytometry 24 h after each injection. Shown in FIGS. 7A-7D are results expressed as cell counts for F4/80 CD11b CD86 (mature, active macrophages); CD11c (DCs); CD11c CD86 (activated DCs); CD4 CD69 (activated T cells); CD8 CD69 (activated cytotoxic T cells); NK1.1 CD3$^+$ CD69 (activated NKT cells); NK1.1 CD3$^-$ CD69 (activated NK cells); CD19 (B cells); and CD19 CD73 CD80 CD273 (memory B cells). The numbers of these mature, activated cells continued to increase with each injection. Overall, the responses to sv6D were greater than those to svL4, with large increases in DCs (CD11c$^+$ and CD11c$^+$ CD86$^+$), T cells (CD3$^+$, CD4$^+$ and CD8$^+$) and NKT cells (NK1.1, CD3$^+$), although CD19$^+$ B cells responded more strongly to svL4. The mean fluorescence intensity did not change significantly, which suggested that the peptides promoted an expansion of mature cell populations. As a control, the expansion of peritoneal cell populations induced by svL4 and sv6D was compared with that of svC1, which as shown in FIG. 2A does not bind to CLEC10A. Populations of specific cell types from animals treated with svC1 did not increase significantly over the 5-day period. These data demonstrate that in the mouse, low doses of svL4 and sv6D induced several-fold increases in mature, active immune cells in the peritoneal cavity.

To determine whether the target(s) for svL4 is located on lymphocytes, with subsequent cross-talk signaling to achieve activation of monocytes, an experiment was performed in which svL4 was injected into RAG$^{-/-}$ mice, which lack activity of rag, the recombination activation gene. The ability to perform recombination to generate antigen-specific antibodies by V(D)J recombination is required for B and T cell precursors to produce functional antigen receptors on their surface, and without a functional rag gene these cells undergo apoptosis [132]. The response of monocytes in the peritoneal cavity of RAG$^{-/-}$ mice to treatment with svL4 was essentially the same as that in C57BL/6 mice. The deficiency of B and T cells did not reduce the maturation of monocytes, which suggested that svL4 acts on targets within the myeloid lineage.

Example 6. Efficacy of Peptides in Murine Model of Ovarian Cancer

The strong responses of the peritoneal immune cells to the peptides led us to test whether they would be effective in treating cancers of peritoneal organs. A murine ovarian cancer cell line (ID8) was implanted into the peritoneal cavity of C57BL/6 female mice on day 0. In this system, tumor progression in the peritoneal cavity is initially slow but then progresses rapidly, with ultimate accumulation of ascites [110]. Treatment with sv6D routinely began 45 days after implantation when macroscopic tumor seeds were present, which is analogous to the stage at which most women are diagnosed [134,135]. Progression of the cancer was monitored by body weight of animals as an indication of ascites accumulation.

Efficacy of sv6D was compared with that of paclitaxel, a standard-of-care chemotherapeutic drug that stabilizes microtubules, interferes with the function of kinetochores, and arrests cells at the G2/M boundary of mitosis [95,96]. In the experiment illustrated in FIGS. 8A-8C, progression of disease was aggressive and evidence of ascites accumulation was observed already at day 45, the time treatment was initiated. After two weeks of treatment, when disease in several control mice had already progressed to end stage, weights of mice treated with sv6D at a dose of 0.1 nmol/g body weight or paclitaxel had not significantly increased. This observation suggested that treatment with sv6D suppressed accumulation of ascites when first evident.

Figures 8A, 8B:
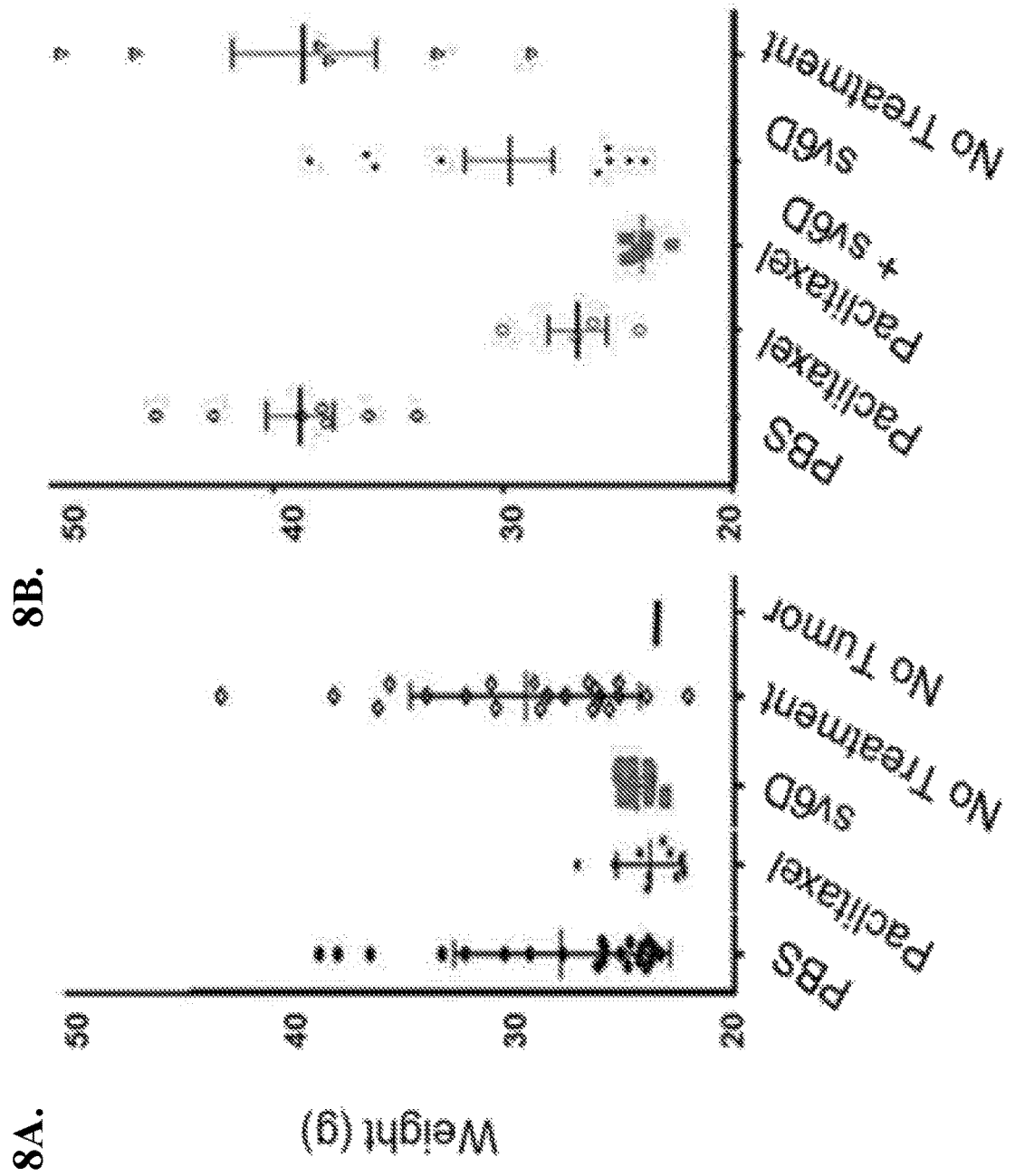
FIGS. 8A-8C. Combination study of sv6D and paclitaxel.
Figure 8C:
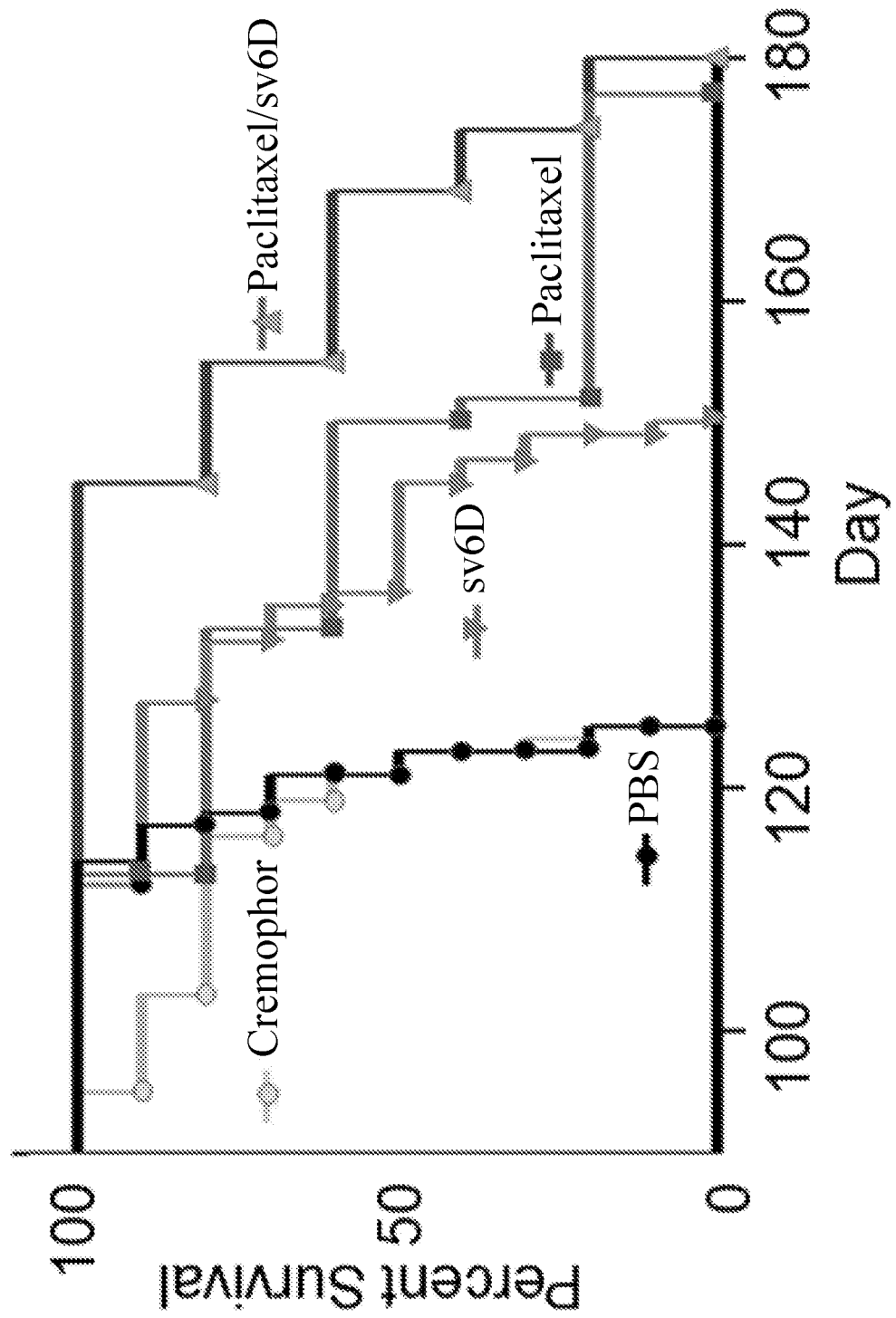

We then asked whether sv6D would be effective in combination with paclitaxel. In this study the disease progressed more slowly, with the median end-stage at day 122. sv6D again suppressed accumulation of ascites when treatment was initiated at day 45, with no significant weight gain for half the animals at day 120 (FIG. 8B). Efficacy of sv6D at a dose of 0.1 nmol/g was comparable to that of paclitaxel, with median survival of approximately 141 days (FIG. 8C). Because cancer cells eventually escape paclitaxel treatment, these results led to initiation of treatment with sv6D at day 100, 50 days after treatment with paclitaxel, when accumulation of ascites was first observed in this group. Over the next 3 weeks, alternate-day injections of sv6D completely suppressed further increases in weight of the animals (FIG. 8B). Continued treatment with sv6D resulted in dramatic extension of survival of the animals to a median of 169 days (FIG. 8C).

The peptide sv6D is highly effective in enhancing the efficacy of chemotherapeutic drugs for prolonging overall survival. Paclitaxel is currently used as a chemotherapeutic drug that acts by stabilizing microtubules and arresting cells in the cell cycle at the G2/M boundary [95,96]. Inhibition of cell division prevents growth of the tumor, but effectiveness of the drug gradually dissipates as it is excreted from the body. Paclitaxel is often combined with a platinum-based drug that binds to DNA and blocks replication [97,98]. Patients treated with these drugs experience a significant level of toxicity. Repeated dosing leads often to resistance to the drugs. Our data show that sv6D would serve as an effective combination drug without adding toxicity. Overall survival time is doubled when a treatment with paclitaxel is followed by treatment with sv6D. However, because sv6D induces proliferation of immune cells, initiation of treatment was delayed until the cell cycle inhibitory action of paclitaxel had dissipated [99].

Example 7. Efficacy of sv6D in Combination with Anti-PD-1

Figures 9A, 9B:
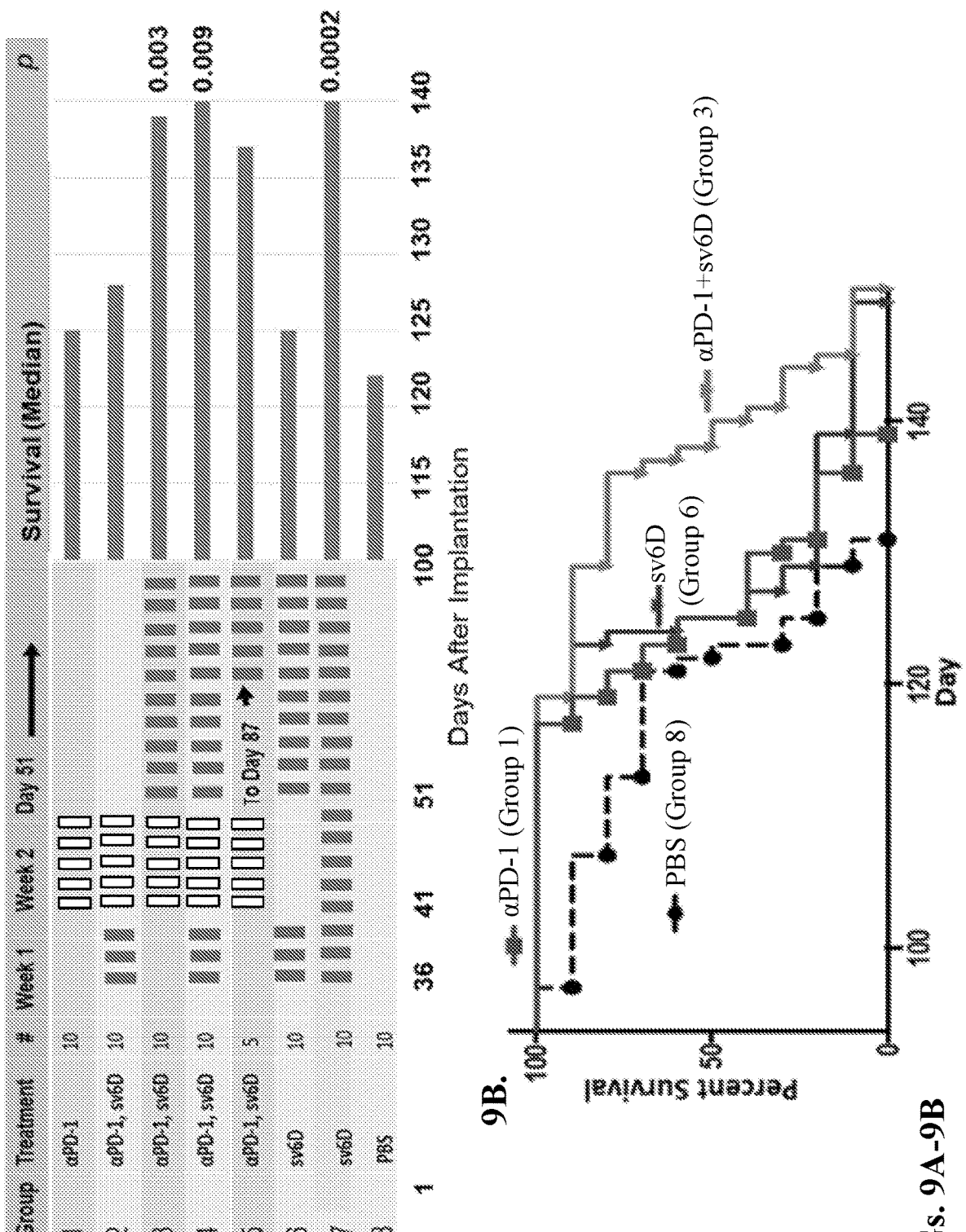
FIGS. 9A-9B. Combination study of sv6D and anti-PD-1.

The peptide sv6D is also highly effective in enhancing the efficacy of immunotherapeutic drugs for prolonging overall survival. Intraperitoneal injection of a monoclonal anti-mouse PD-1 is modestly effective in mice with ovarian cancer model [102,103]. We tested whether sv6D would extend effectiveness of anti-PD-1. Five doses of anti-PD-1 (200 μg in PBS) were injected intraperitoneally on alternate days between days 41 and 49. sv6D was injected subcutaneously immediately after the treatment with anti-PD-1 and continued on alternate days to the end of the study (FIG. 9A, Group 3). When administration of sv6D to a group that had been treated with anti-PD-1 was delayed until day 87, after weight of the animals began to increase (Group 5), essentially complete suppression of ascites formation was sustained for several weeks.

Specifically, in the study shown in FIG. 9A, injections of anti-PD-1 alone (Group 1) did not provide an extension of life significantly beyond injections of the vehicle PBS as a control (Group 8). In contrast, alternate-day injections of sv6D (Group 7) provided maximal survival. The combination of anti-PD-1 with sv6D (Group 4) also provided maximal survival, which demonstrated that sv6D can rescue individuals that do not respond to the immunotherapeutic drug, anti-PD-1. Group 6, with a hiatus of one week after a week of treatment with sv6D, survived only slightly longer than animals treated with PBS. This observation appears similar to the unresponsiveness of T cells that was observed in mice within a week after treatment with antibodies against C-type lectin receptors on DCs [17,136]. The treatment provided a highly significant extension of survival of the animals (FIG. 9B).

Patients with ovarian cancer have a 15% overall response rate during treatment with antibodies against the inhibitory receptor PD-1 (pembroliumab or nivolumab in human therapy) [100,101]. The antibodies exhibit very modest effectiveness in mouse models [102,103]. The peptide sv6D alone inhibited accumulation of ascites to a greater extent than anti-PD-1 and also was effective in combination with the antibody. Our peptide drugs satisfy the criteria described by Hamanishi et al., [104], who concluded that "particularly important in ovarian cancer, (which) is not associated with a high response rate, anti-cancer treatments are considered to be excellent if they are associated with low medical costs, low toxicity and high 'benefits' (anti-tumor response)."

Example 8. Toxicity of Peptide Treatment

Although weight gain is a good measure of disease progression in this model of disseminated ovarian cancer in the peritoneal cavity, consideration of mean group weight is complex. Because this is an intact biological model, inherent variation exists. As disease in individual animals within a treatment group progress, the variation in weight within the treatment group increases. When an individual animal reaches end-stage disease and is euthanized, the mean group weight may drop and the variation within the group decreases. Given this complexity, there remained several instances in which reduced progression of disease within a treatment group was reflected in differences in weight that reached statistical significance.

Figure 10:
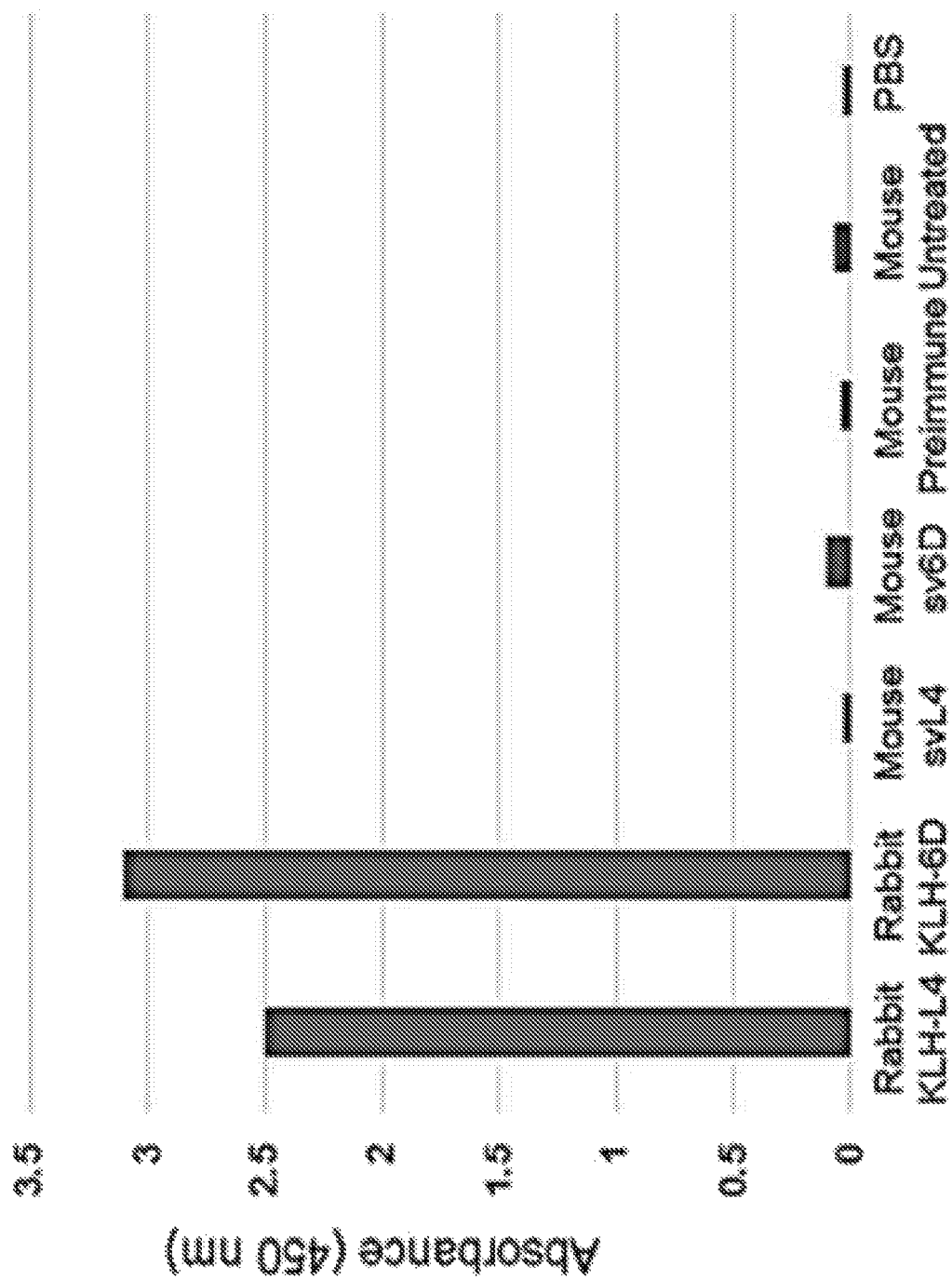
FIG. 10. Test for antigenicity of svL4 and sv6D. Anti-sera were generated in rabbits against KLH-conjugates of the sequences of svL4 or sv6D and diluted 1:10. Mouse sera were collected after alternate-day injections of svL4 over 3 months, diluted 1:1 with PBS and added to protein-A/G-coated wells. Biotinylated svL4 or sv6D was added to wells and bound peptide was detected with a streptavidin-peroxidase conjugate. The figure includes average values for sera from 8 treated mice in each group assayed separately.

It is important to note that during and after drug administration there was no change in mouse behavior, indicating no overt toxicity related to peptide treatment. Further, repeated injection of peptide in the same region resulted in no apparent irritation or formation of fibrous or granulomatous tissue. Attempts to detect antibodies that bind the peptides in sera from mice injected on alternate days for 3 months with 1 nmol/g svL4 or sv6D were negative (FIG. 10), which indicated that the peptides are not antigenic in mice.

Figure 11A:
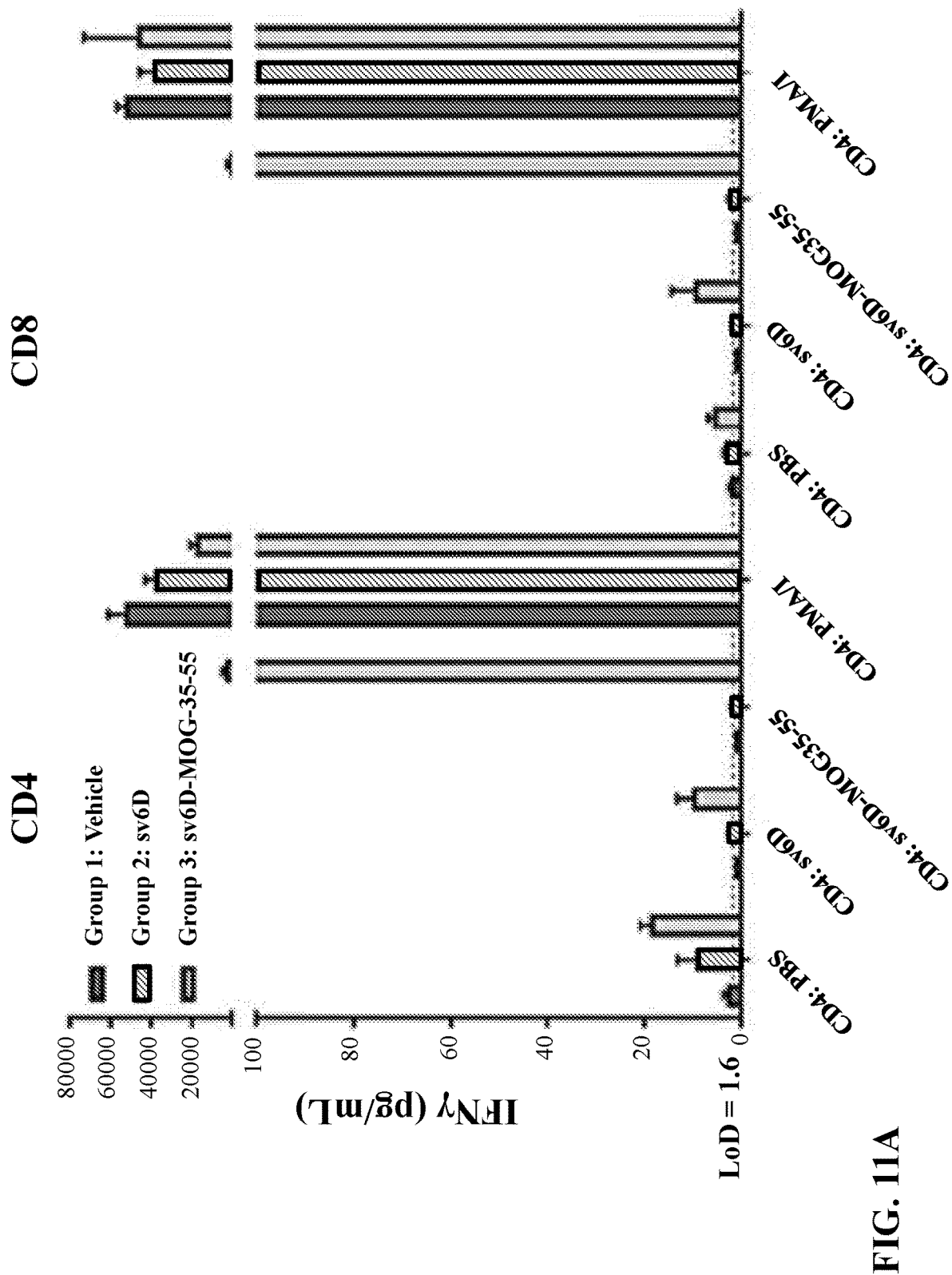
FIGS. 11A-11B. Activation of T cells by sv6D-antigen conjugate. IFN-γ (FIG. 11A) and IL-2 (FIG. 11B) production upon in vitro challenge of T cells after weekly injections of sv6D or sv6D-MOG (MOG=myelin oligodendrocyte glyco-protein$_{35-55}$) into C57BL/6 mice. One week after the second injection, spleen and right inguinal lymph node tissue were combined and homogenized to allow isolation of CD4 and CD8 T cells, which were mixed with non-T cell antigen presenting cells, and incubated 72 h with PBS, sv6D or sv6D-MOG. PMA (phorbol 12-myristate 13-acetate) and I (ionomycin) were added as positive controls. Activation of CD8+ T cells indicated cross-presentation of the antigen to the cytosol of dendritic cells, mediated by sv6D.
Figure 11B:
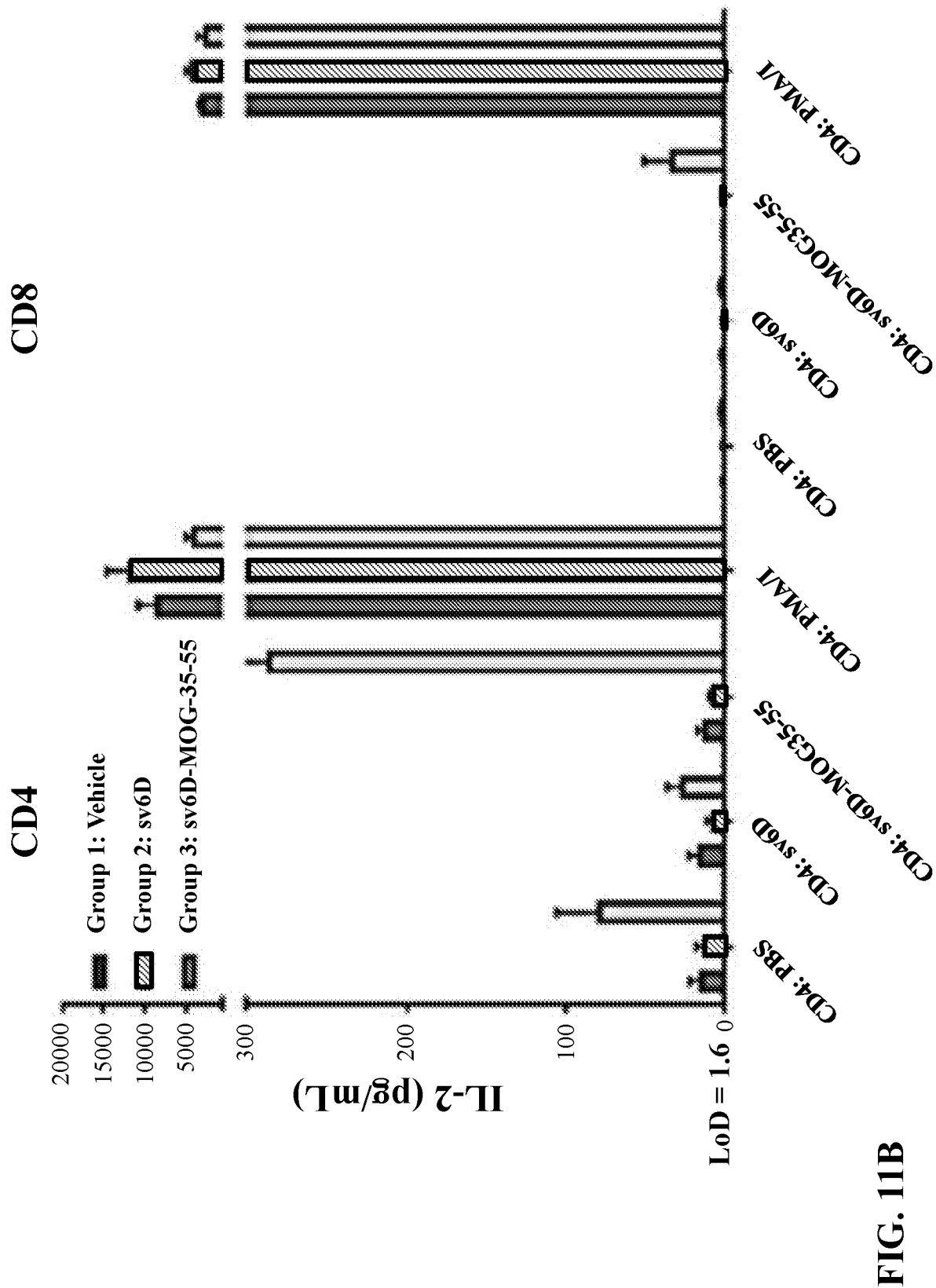

Whereas sv6D is not antigenic in the mouse (FIG. 10), it is important to determine whether the peptide gains access to the cytosol of DCs. To test whether sv6D could initiate a $T_H1$ response and activate $CD8^+$ T cells, a fragment of the myelin oligodendrocyte glycoprotein ($MOG_{35-55}$) was attached to the C-terminus of sv6D and injected into mice. One week after a second weekly injection of 0.1 nmol/g peptide, $CD4^+$ and $CD8^+$ T cells were challenged in vitro with the conjugate. As shown in FIG. 11A, a strong release of IFN-γ occurred with both types of T cells. A high level of IL-2 was also released by $CD4^+$ T cells (FIG. 11B). These observations are typical of a strong response to vaccination and stimulation of clonal T cell proliferation. The "vehicle" sv6D did not induce IFN-γ release, even from the cells from animals treated with sv6D-MOG, nor did the antigen $MOG_{35-55}$ when not attached to sv6D. The response of $CD8^+$ T cells suggested that the conjugate indeed gained access to the cytosol and the MHC class I pathway by cross-presentation [93]. Within the endosomal pathway, the conjugate was also loaded onto MHC class II complexes for activation of $CD4^+$ T cells [94].

To determine whether the peptides induced a significant release of cytotoxic cytokines, sera were collected from female Balb/c mice into which breast cancer 4T1 cells had been implanted. After the tumors had grown over a period of 10 to 12 days to a size of ~500 mm³, svL4 was injected subcutaneously at doses of 0.1 or 1.0 nmol/g. Sera were prepared 4 h after injection and analyzed with an array of 308 cytokines/chemokines. Ratios of the amounts of selected cytokines from treated vs. untreated mice are listed in Table 2.

Several cytokines had negligible values in untreated mice, and thus the ratio of treated (although low) vs. untreated animals had a high value. Ratios of treated vs. untreated samples obtained in a separate experiment with healthy Balb/c mice are shown in the right-hand column of Table 2 for comparison. The most significant increase in the serum of healthy mice treated with the peptide was in the amount of soluble HVEM (Herpes virus entry mediator, also designated TNFRSF14), which was a prominent protein in serum and increased approximately 10-fold within 4 h after treatment. In the tumor-bearing mice, the level of soluble HVEM in treated animals was similar to that in treated healthy mice, but the level in untreated animals was higher than that in healthy control mice. Interestingly, cytokines that were strongly elevated in mice bearing tumors were often reduced in healthy mice in response to svL4 or showed no change. The amounts of inflammatory cytokines in the sera did not appear to reach toxic levels.

Importantly, when challenged, the T cells that released IFN-γ and IL-2 did not release significant amounts of IL-4, IL-5, IL-10, IL-13 or TNF-α. These data show that sv6D can initiate a humoral response without generating the immunosuppressive cytokines such as IL-4, IL10 and IL-13. Activation of T cells by DCs is the initial step in generation of antibodies against the antigen.

Example 9. Targeting of Drugs to CLEC10A-Expressing Cells by sv6D

Scheme 1. sv6D as a Vehicle to Deliver Chemicals

During synthesis of the peptides, the C-terminus can be modified by several means. Firstly, the amino acid cysteine is added to provide a sulfhydryl group at the C-terminus. To this —SH group, another compound with a —SH group can be linked by oxidation to a —S—S— group. Further, a compound that contains an iodo-group can react with the —SH group of C-terminal cysteine to link a number of different types such as dyes, compounds containing a reactive group such as a methylacrylate, etc.

Scheme 2. Attachment of cyclic dinucleotides (CDN) for activation of STING pathway.

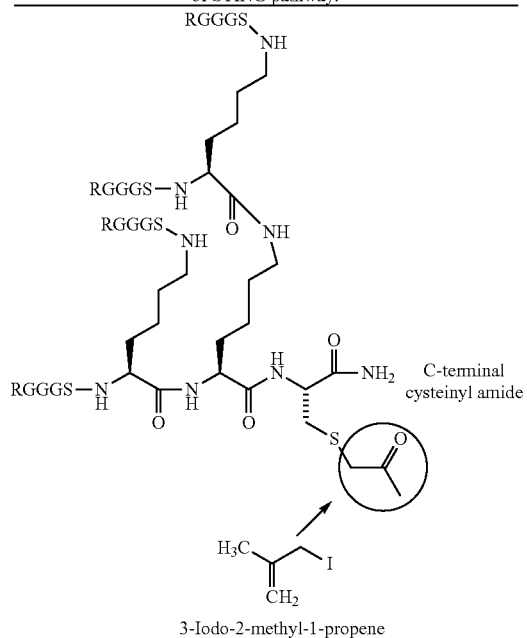

3-Iodo-2-methyl-1-propene
R = peptide

The N-acetylated-peptide, made with a C-terminal carboxyl group, can be linked to the N-terminal amino group of another molecule with a carbodiimide derivative. Thus, a CDN, a ligand for STING [79] that contains an amino group, was linked to the C-terminal carboxyl group of sv6D. This conjugate was tested with the reporter cell line THP1-Dual cells (InvivoGen) and found to be 500-fold more effective in activating the STING pathway that leads to IFN-β than the CDN itself.

The ability of sv6D-CDN conjugates to induce activation of the STING pathway for production of type 1 interferons (IFN-α/β) was tested by incubating human THP1 monocytes that were genetically engineered as reporter cells (InvivoGen, San Diego, Calif.), with the conjugate. Activation of the STING pathway causes secretion of the enzyme luciferase, which can be assayed in the medium as described by the supplier's instructions. Because the initial steps in this pathway are in the cytoplasm of the cells, access of the cytosol to sv6D is essential, which was demonstrated by the activation of CD8+ T cells illustrated in FIG. 11. Luciferase activity was detected in the medium of cultures that were incubated with sv6D-cyclic dinucleotide conjugates at concentrations in the nanomolar range, whereas treatment of cells with cyclic dinucleotides required concentrations in the micromolar range to detect luciferase activity (FIG. 12). The primary factor in induction of the pathway at the lower concentrations by the conjugate was likely the receptor-mediated entrance into the cells, whereas the cyclic dinucleotides pass through the cell membrane poorly. The $K_D$ of the STING protein for cyclic dinucleotides is approximately 5 μM [108,109], which suggests that the peptide sv6D is orders-of-magnitude more effective in delivering the activating factor than the natural ligand itself.

Figure 15:
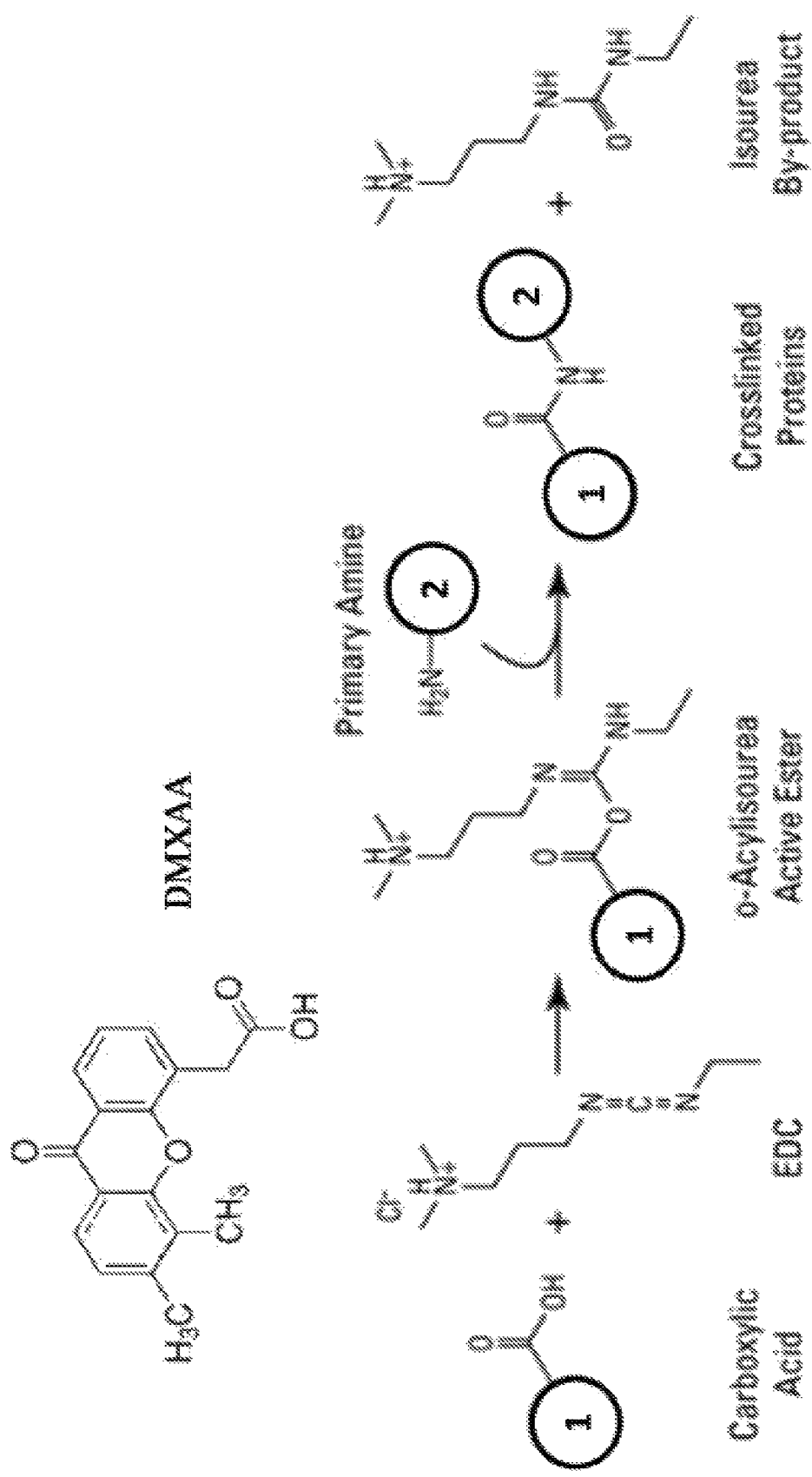
FIG. 15 depicts conjugation between svL4 and DMXAA (5,6-dimethylxanthenone-acetic acid), a ligand for murine STING. DMXAA is shown as an example of a compound that contains a free carboxylic acid group.

For svL4, because the active binding sequence is the C-terminal 6 amino acids, the N-terminal half can serve as a linker to a attach compounds that react with an amino group. For example, compounds with a carboxyl group can be linked to the N-terminal amino groups of the peptides with a carbodiimide derivative (FIG. 15). Thus, the molecule DMXAA (5,6-dimethylxanthenone-acetic acid), a ligand for murine STING [132] that contains a carboxyl group, was linked to the N-terminal amino groups of sv6D. This conjugate binds STING and activate the pathway that leads to IFN-β.

Scheme 3. Coupling of the Cytotoxic Drug Doxorubicin sv6D that was synthesized with acetylated N-termini and a C-terminal linker with an amino group was coupled with doxorubicin through its amino group by reaction with glutaraldehyde. The expression of CLEC10A on tumor cells and immunosuppressive macrophages provides the opportunity to reduce numbers of these cells by targeting a cytotoxic drug such as doxorubicin conjugated to sv6D. Doxorubicin is a potent, although toxic, anticancer drug, which when provided through a cell-specific delivery can increase efficacy while decreasing the side effects [137].

Figure 14A:
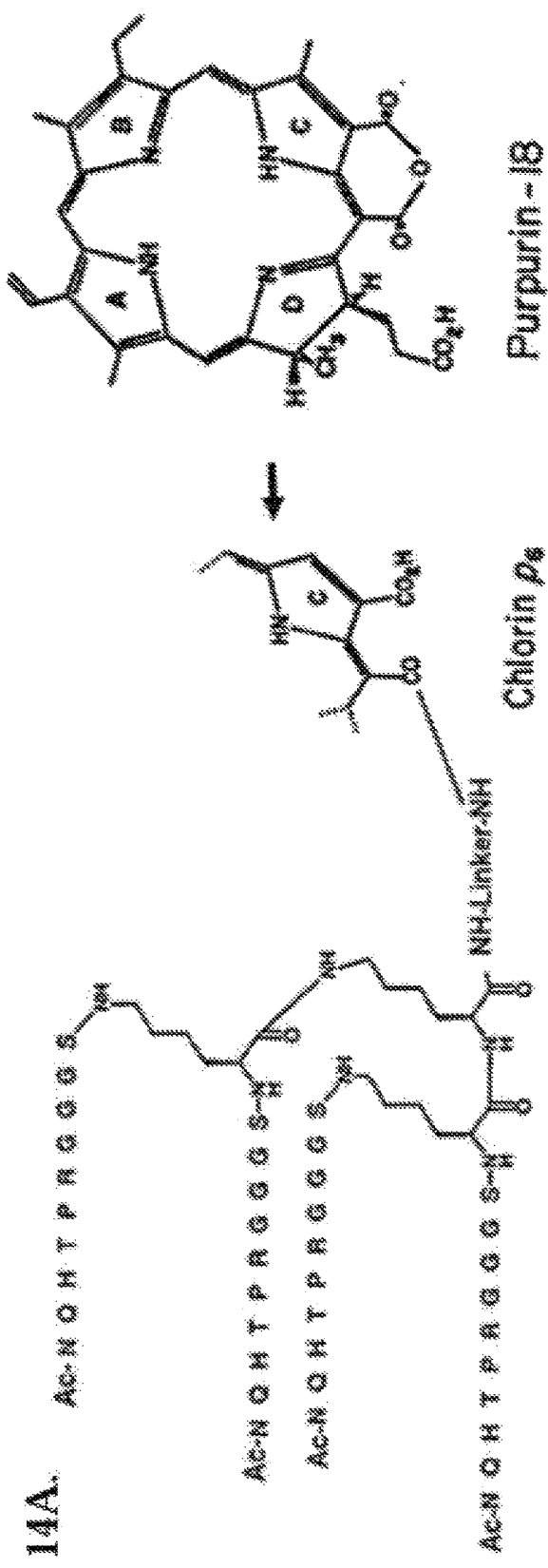
FIGS. 14A-14B. Conjugation with photosensitive chlorin.
Figure 14B:
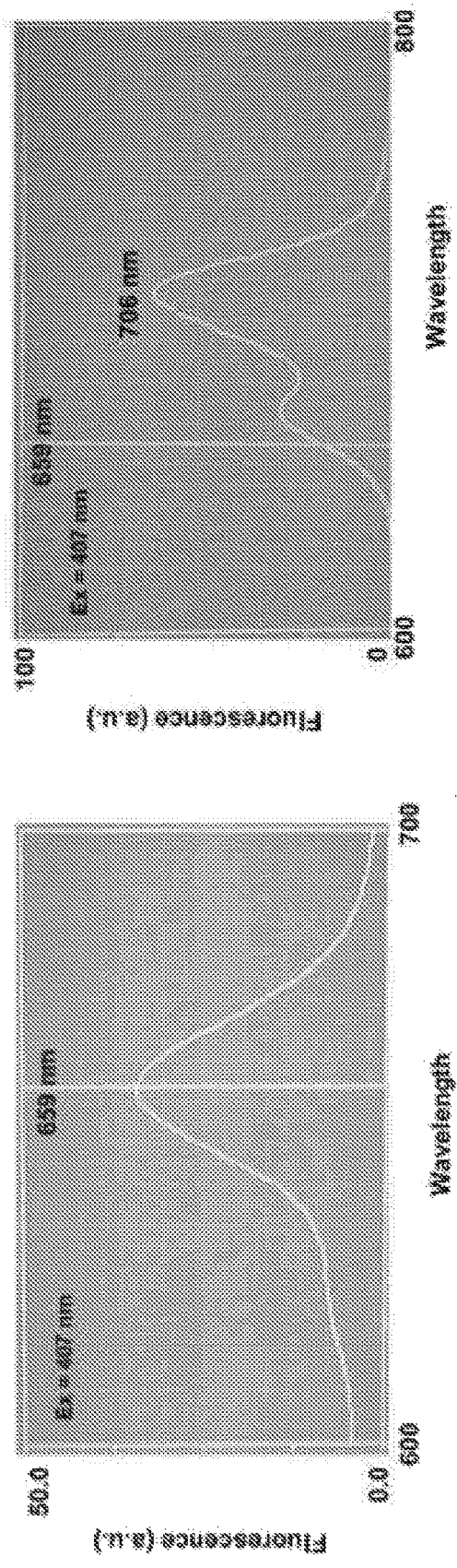

Scheme 4. Attachment of Photosensitizes Chlorin $p_6$ to sv6D.

sv6D was prepared with N-terminal acetyl groups and a free amino group at the C-terminus. Purpurin-18 contains an anhydride group that reacts readily with a nucleophilic amine group, which results in an amide linkage between the peptide and the derivative chlorin $p_6$ (FIGS. 14A-14B) The chlorophyll derivatives are potent photosensitizers of cell killing when exposed to red light, with $IC_{50}$ for chlorin $p_6$ of 30 nM [90]. The advantage of the conjugate is to target the photosensitizer to tumor cells that express CLC10A, which can be selectively exposed to red light. The chlorin is not toxic in the dark.

REFERENCES

1. Eggink L L, Salas M, Hanson C V, Hoober J K. Peptide sugar mimetics prevent HIV Type 1 replication in peripheral blood mononuclear cells in the presence of HIV-positive antiserum. AIDS Res Human Retrovir. 2010; 26:149-160.
2. Eggink L L, Spyroulias G A, Jones N G, Hanson C V, Hoober J K. A peptide mimetic of 5-acetylneuraminic acid-galactose binds with high avidity to siglecs and NKG2D. PLoS ONE 2015; 10: e0130532.
3. Matsubara T. Potential of peptides as inhibitors and mimotopes: selection of carbohydrate-mimetic peptides from phage display libraries. J Nucleic Acids. 2012, Article ID 740982.
4. Geijtenbeek T B H, Gringhuis S I. C-type lectin receptors in the control of T helper cell differentiation. Nat Rev Immunol. 2016; 16:433-448.
5. Brown G D, Willment J A, Whitehead L. C-type lectin in immunity and homeostatsis. Nat Rev Immunol. 2017; doi.org/10.1038/s41577-018-0004-8.
6. van Kooyk Y, Ilarregui J M, van Vliet S J. Novel insights into the immunomodulatory role of the dendritic cell and macrophage-expressed C-type lectin MGL. Immunobiology 2015; 220: 185-192.
7. Zizzari I G, Napoletano C, Battisti F, Rahimi H, Caponnetto S, Pierelli L, Nuti M, Rughetti A. MGL receptor and immunity: when the ligand can make the difference. J Immunol Res. 2015; article 450695:doi.org/10.1155/2015/450695.
8. Yan H, Kamiya T, Suabjakyong P, Tsuji N M. Targeting C-type lectin receptors for cancer immunity. Front Immunol. 2015; 6:408. doi.10.3389/fimmu.2015.00408.
9. Drickamer K, Taylor M E. Recent insights into structures and functions of C-type lectins in the immune system. Curr Opin Struct Biol. 2015; 34:26-34.
10. Ng K K-S, Park-Snyder S, Weis W I. $Ca^{2+}$-dependent structural changes in C-type mannose-binding proteins. Biochemistry 1998; 37:17965-17976.
11. Feinberg H, Park-Snyder S, Kolatkar A R, Heise C T, Taylor M E, Weis W I. Structure of a C-type carbohydrate recognition domain from the macrophage mannose receptor. J Biol Chem. 2000; 275:21539-21548.
12. Meier M, Bider M D, Malashkevich V N, Spiess M, Burkhard P. Crystal structure of the carbohydrate recognition domain of the H1 subunit of the asialoglycoprotein receptor. J Mol Biol. 2000; 300:857-865.
13. Higashi N, Fujioka K, Denda-Nagai, Hashimoto S, Nagai S, Sato T, et al. The macrophage C-type lectin specific for galactose/N-acetylgalactosamine is an endocytic receptor expressed on monocyte-derived immature dendritic cells. J Biol Chem. 2002; 277:20686-20693.
14. van Vliet S J, Saeland E, van Kooyk Y. Sweet preferences of MGL: carbohydrate specificity and function. Trends Immunol. 2008; 29:83-90.
15. Zhang W, Xu W, Xiong S. Macrophage differentiation and polarization via phosphatidylinositol 3-kinase/Akt-ERK signaling pathway conferred by serum amyloid P component. J Immunol. 2011; 187:1764-1777.
16. Wong K L, Yeap W H, Tai J J Y et al. The three human monocyte subsets: implications for health and disease. Immunol Res. 2012; 53:41-57.
17. Cote R, Eggink L L, Hoober J K. CLEC receptors, endocytosis and calcium signaling. AIMS Allerg Immunol. 2017; 1:207-231. doi: 10.3934/Allergy.2017.4.207
18. Morgan A J, Platt F M, Lloyd-Evans E, Galione A. Molecular mechanisms of endolysosomal $Ca^{2+}$ signaling in health and disease. Biochem J. 2011; 439:349-374.
19. Plattner H, Verkhratsky A. Inseparable tandem: evolution chooses ATP and $Ca^{2+}$ to control life, death and cellular signaling. Phil Trans R Soc B. 2016; 371: 20150419.
20. Carafoli E, Krebs J. Why calcium? How calcium became the best communicator. J Biol Chem. 2016; 291:20849-20857.
21. Faries M B, Bedrosian I, Xu S, Koski G, Roros J G, Moise M A, et al. Calcium signaling inhibits interleukin-12 production and activates $CD83^+$ dendritic cells that induce Th2 development. Blood 2001; 98:2489-2497.
22. Shumilina E, Huber S M, Lang F. $Ca^{2+}$ signaling in the regulation of dendritic cell functions. Am J Physiol Cell Physiol. 2011; 300:C1205-C1214.
23. Schjoldager KTBG, Clausen H. Site-specific protein O-glycosylation modulates preprotein processing—deciphering specific functions of the large polypeptide GalNAc-transferase gene family. Biochim Biophys Acta 2012; 1820:2079-2094.
24. Perez-Vilar J, Hill R L. The structure and assembly of secreted mucins. J Biol Chem. 1999; 274: 31751-31754.
25. Pinho S S, Reis C A. Glycosylation in cancer: mechanisms and clinical implications. Nat Rev Cancer 2015; 15:540-555.
26. Zheng J, Xiao H, Wu R. Specific identification of glycoproteins bearing the Tn antigen in human cells. Angew Chem Int Ed Engl. 2017; 56:7107-7111.
27. Singhal A, Fohn M, Hakomori S-I. Induction of α-N-acetylgalactosamine-O-serine/threonine (Tn) antigen-mediated cellular immune response for active immunotherapy in mice. Cancer Res. 1991; 51:1406-1411.
28. Freire T, Zhang X, Dériaud E, Ganneau C, Vichier-Guerre S, Azria E, et al. Glycosidic Tn-based vaccines targeting dermal dendritic cells favor germinal center B-cell development and potent antibody response in the absence of adjuvant. Blood 2010; 116:3526-3536.
29. Freire T, Lo-Man R, Bay S, Leclerc C. Tn glycosylation of the MUC6 protein modulates its immunogenicity and promotes the induction of Th17-biased T cell responses. J Biol Chem. 2011; 286:7797-7811.
30. Madsen C B, Petersen C, Lavrsen K, Harndahl M, Buus, Clausen H, Pedersen A E, Wandall H H. Cancer associated aberrant protein O-glycosylation can modify antigen processing and immune response. PLoS ONE 2012; 7(11): e50139. doi:10.1371/journal.pone.0050139.
31. Liu S-Y, Shun C-T, Hung K-Y, Juan H-F, Hsu C-L, Huang M-C, Lai I-Rue. Mucin glycosylating enzyme GALNT2 suppresses malignancy in gastric adenocarcinoma by reducing MET phosphorylation. Oncotarget 2016; 7:11251-11261.
32. Napoletano C, Rughetti A, Agervig Tarp M P, Coleman J, Bennett E P, Picco G, et al. Tumor-associated Tn-MUC1 glycoform is internalized through the macrophage galactose-type C-type lectin and delivered to the HLA class I and II compartments in dendritic cells. Cancer Res. 2007; 67:8358-8367.
33. Irazoqui F, Sendra V G, Lardone R D, Nores G A. Immune response to Thomsen-Friedenreich disaccharide and glycan engineering. Immunol Cell Biol. 2005; 83:405-412.

34. Chia J, Goh G, Bard F. Short 0-GalNAc glycans: regulation and role in tumor development and clinical perspectives. Biochim Biophys Acta 2016; 1860:1623-1639.
35. Springer G F. T and Tn, general carcinoma autoantigens. Science 1984; 224; 1198-1206.
36. Springer G F. Immunoreactive T and Tn epitopes in cancer diagnosis, prognosis, andimmunotherapy. J Mol Med. 1997; 75:594-602.
37. Napoletano C, Zizzari I G, Rughetti A, Rahimi H, Irimura T, Clausen H, et al. Targeting of macrophage galactose-type C-type lectin (MGL) induces DC signaling and activation. Eur J Immunol. 2012; 42:936-945.
38. Lo-Man R, Vichier-Guerre S, Bay S, Dériaud E, Cantacuzène D, Leclerc C. Anti-tumor immunity provided by a synthetic multiple antigenic glycopeptide displaying a Tri-Tn glycotope. J Immunol. 2001; 166:2849-2854.
39. Jégouzo S A F, Quintero-Martinez, Ouyang X, et al. Organization of the extracellular portion of the macrophage galactose receptor: A trimeric cluster of simple binding sites for N-acetylgalactosamine. Glycobiology 2013; 23:853-864.
40. Garg S, Oran A, Wajchman J, Sasaki S, Maris C H, Kapp J A, et al. Genetic tagging shows increased frequency and longevity of antigen-presenting, skin-derived dendritic cells in vivo. Nat Immunol. 2003; 4:907-912.
41. Tomura M, Hata A, Matsuoka S, Shand F H, Nakanishi Y, Ikebuchi R, et al. Tracking and quantification of dendritic cell migration and antigen trafficking between the skin and lymph nodes. Sci Rep. 2014; 4:6030.
42. Kitano M, Yamazaki C, Takumi A, Ikeno T, Hemmi H, Takahashi N, et al. Imaging of the cross-presenting dendritic cell subsets in the skin-draining lymph node. Proc Natl Acad Sci USA 2016; 113:1044-1049.
43. Grewal P K. The Ashwell-Morell receptor. Methods Enzymol. 2010; 479:223-241.
44. Weigel P H, Yik J H N. Glycans as endocytosis signals: the cases of the asialoprotein and hyaluronan/chrondroitin sulfate receptors. Biochim Biophys Acta 2002; 1572:341-363.
45. Feinberg H, Torgersen D, Drickamer K, Weiss W I. Mechanism of pH-dependent N-acetylgalactosamine binding by a functional mimic of the hepatic asialoglycoprotein receptor. J Biol Chem. 2000; 275:35176-35184.
46. Schwartz A L, Rup D, Lodish H F. Difficulties in the quantification of asialoglycoprotein receptors on the rat hepatocyte. J Biol Chem. 1980; 255:9033-9036.
47. Bon C, Hofer T, Bousquet-Mélou A, Davies M R, Krippendorff B F. Capacity limits of asialoglycoprotein receptor-mediated liver targeting. MAbs 2017; 9:1360-1369.
48. Yamamoto K, Ishida C, Shinohara Y, Hasegawa Y, Konami Y, Osawa T, Irimura T. Interaction of immobilized recombinant mouse C-type macrophage lectin with glycopeptides and oligosaccharides. Biochemistry 1994; 33:8159-8166.
49. Khorev O, Stokmaier D, Schwardt O, Cutting B, Ernst B. Trivalent, Gal/GalNAc-containing ligands designed for asialoglycoprotein receptor. Bioorg Med Chem. 2008; 16:5216-5231.
50. Dixon L J, Barnes M, Tang H, Pritchard M T, Nagy L E. Kupffer Cells in the Liver Compr Physiol. 2013; 3:785-797.
51. Coombs P J, Taylor M E, Drickamer K. Two categories of mammalian galactose-binding receptors distinguished by glycan array profiling. Glycobiology 2006; 16:1C-7C.
52. van Vliet S J, Gringhuis S I, Geijtenbeek T B H, van Kooyk Y. Regulation of effector T cells by antigen-presenting cells via interaction of the C-type lectin MGL with CD45. Nat Immunol. 2006; 7:1200-1208.
53. Coombs P J, Harrison R, Pemberton S, Quintero-Martinez A, Parry S, Hasiam S M, et al. Identification of novel contributions to high-affinity glycoprotein-receptor interactions using engineered ligands. J Mol Biol. 2010; 396:685-696.
54. Hermiston M L, Xu Z, Weiss A. CD45: a critical regulator of signaling thresholds in immune cells. Annu Rev Immunol. 2003; 21:107-137.
55. Tong A, Nguyen J, Lynch K W. Differential expression of CD45 isoforms is controlled by the combined activity of basal and inducible splicing-regulatory elements in each of the variable exons. J Biol Chem. 2005; 280: 38297-38304.
56. Xu Z, Weiss A. Negative regulation of CD45 by differential homodimerization of the alternatively spliced isoforms. Nat Immunol. 2002; 3:764-771.
57. Kumar V, Cheng P, Condamine T, Mony S, Languino L R, McCaffrey J C, et al. CD45 phosphatase inhibits STAT3 transcription factor activity in myeloid cells and promotes tumor-associated macrophage differentiation. Immunity 2016; 44:303-315.
58. McNeill L, Cassady R L, Sarkardei S, Cooper J C, Morgan G, Alexander D R. CD45 isoforms in T cell signaling and development. Immunol Lett. 2004; 92:125-134.
59. Seki I, Suzuki M, Miyasakaa N, Kohsakaa H. Expression of CD45 isoforms correlates with differential proliferative responses of peripheral $CD4^+$ and $CD8^+$ T cells. Immunol Lett. 2010; 129:39-46.
60. Eggink L L, Hoober J K. A biologically active peptide mimetic of N-acetylgalactosamine/galactose. BMC Res Notes 2009; 2:23.
61. Reche P A, Glutting J-P, Reinherz E L. Prediction of MEW class 1 binding peptides using profile motifs. Human Immunol. 2002; 63:701-709.
62. Escobar H, Crockett D K, Reyes-Vargas E, Baena A, Rockwood A L, Jensen P E, Delgado J C. Large scale mass spectrometric profiling of peptides eluted from HLA molecules reveals N-terminal-extended peptide motifs. J Immunol. 2008; 181:4874-4882.
63. Klimmeck D, Hansson J, Raffel S, Vakhrushev S Y, Trumpp A, Krijgsveld J. Proteomic cornerstones of hematopoietic stem cell differentiation: distinct signatures of multipotent progenitors and myeloid committed cells. Mol Cell Prot. 2012; 11:286-302.
64. Degli-Esposti, Smyth M J. Close encounters of different kinds: dendritic cells and N K cells take centre stage. Nat Rev Immunol. 2005; 5:112-124.
65. Reschner A, Hubert P, Delvenne P, Boniver J, Jacobs N. Innate lymphocyte and dendritic cell cross-talk: a key factor in the regulation of the immune response. Clin Exp Immunol. 2008; 152:219-226.
66. Rapoport E M, Khaidukov S V, Gaponov A M, Pazynina G V, Tsygankova S V, Ryzhov I M, et al. Glycan recognition by human blood mononuclear cells with an emphasis on dendritic cells. Glycoconjugate J. 2018; 35:doi.org/10.1007/s10719-017-9811-6.
67. Ohshio G, Imamura T, Imamura H, Yamabe H, Sakahara H, Nakada H, Yamashina I. Distribution of Tn antigen recognized by an anti-Tn monoclonal antibody (MLS128) in normal and malignant tissues of the digestive tract. J Cancer Res Clin Oncol. 1995; 121:247-252.

68. Ayers M, Loboda A, Lunceford J, McClanahan T K, Murphy E, Nebozhyn M, Pierce R H. P D-L1 gene signature biomarkers of tumor response to PD-1 antagonists. U S Patent Application 2016/0312297.
69. Ayers M, Lunceford J, Loboda A, Nebozhyn M, McClanahan T K, Hirsch H. Blood-based biomarkers of tumor sensitivity to PD-1 antagonists. U S Patent Application 2018/0148790.
70. Roberts W K, Hovanessian A, Brown R E, Clemens M J, Kerr I M. Interferon-mediated protein kinase and low-molecular-weight inhibitor of protein synthesis. Nature 1976; 264:477-480.
71. Kerr I M, Brown R E. pppA2'p5'A: an inhibitor of protein synthesis synthesized with an enzyme fraction from interferon-treated cells. Proc Natl Acad Sci USA 1978; 75:256-260.
72. Zhou A, Hassel B A, Silverman R H. Expression cloning of 2-5A-dependent RNAase: a uniquely regulated mediator of interferon action. Cell 1993; 72:753-765.
73. Silverman R H. (2007) Viral encounters with 2',5'-oligoadenylate synthetase and RNase L during the interferon antiviral response. J Virol 2007; 81:12720-12729.
74. Silverman R H. A scientific journey through the 2-5A/RNase L system. Cytokine & Growth Factor Rev 2007; 18:381-388.
75. Wreschner D H, James T C, Silverman R H, Kerr I M. Ribosomal RNA cleavage, nuclease activation and 2-5A (ppp(A2'p)nA) in interferon-treated cells. Nucleic Acids Res 1981; 9:1571-1581.
76. Malathi K, Dong M, Gale Jr M, Silverman R H. Small self-RNA generated by RNase L amplifies antiviral innate immunity. Nature 2007; 448:816-819.
77. Loo Y-M, Gale Jr M (2011) Immune signaling by RIG-1-like receptors. Immunity 2011; 34:680-692.
78. Woo S-R, Fuertes M B, Corrales L, et al. STING-dependent cytosolic DNA sensing mediates innate immune recognition of immunogenic tumors. Immunity 2014; 41:830-842.
79. Barber G N. STING: infection, inflammation and cancer. Nature Rev Immunol 2015; 15:760-770.
80. Chen Q, Sun L, Chen Z J (2016) Regulation and function of the cGAS-STING pathway of cytosolic DNA sensing. Nature Immunol 17: 1142-1149.
81. Ishikawa H, Barber G N. STING is an endoplasmic reticulum adaptor that facilitates innate immune signaling. Nature 2008; 455:674-678.
82. Burdette D L, Monroe K M, Sotelo-Troha K, et al. (2011) STING is a direct innate immune sensor of cyclic di-GMP. Nature 478: 515-519.
83. Zhang X, Shi H, Wu J, et al. Cyclic GMP-AMP containing mixed phosphodiester linkages is an endogenous high-affinity ligand for STING. Molec Cell 2013; 51:226-235.
84. Baird J R, Friedman D, Cottam B, et al. Radiation therapy combined with novel STING-targeting oligonucleotides results in regression of established tumors. Cancer Res 2016; 76:50-61.
85. Kato K, Omura H, Ishitani R, Nureki O. Cyclic GMP-AMP as an endogenous second messenge in innate immune signaling by cytosolic DNA. Annu Rev Biochem 2017; 86:541-66.
86. Fu J, David B, Kanne D B, et al. (2015) STING agonist formulated cancer vaccines can cure established tumors resistant to PD-1 blockade. Sci Transl Med 2015; 7:283ra52.
87. Demaria O, De Gassart A, Coso S, et al. STING activation of tumor endothelial cells initiates spontaneous and therapeutic antitumor immunity. Proc Natl Acad Sci USA 2015; 112:15408-15413.
88. Kessel D. Hematoporphyrin and HPD: photophysics, photochemistry and phototherapy. Photochem Photobiol 1984; 39:851-859.
89. Dougherty T J. Photosensitizers: therapy and detection of malignant tumors. Photochem Photobiol 1987; 45:879-889.
90. Hoober J K, Sery T W, Yamamoto N. Photodynamic sensitizers from chlorophyll: purpurin-18 and chlorin $p_6$. Photochem Photobiol 1988; 48:579-582.
91. Sato K, Hanaoka H, Watanabe R, et al. Near infrared photoimmunotherapy in the treatment of disseminated peritoneal ovarian cancer. Mol Cancer Ther 2014; 14:141-150.
92. Dou X, Nomoto T, Takemoto H, et al. (2018) Effect of multiple cyclic RGD peptides on tumor accumulation and intratumoral distribution of IRDye700D X-conjugated polymers. Sci Rep 2018; 8:8126.
93. Joffre O P, Segura E, Savina A, Amigorena S. Cross-presentation by dendritic cells. Nat Rev Immunol. 2012; 12:557-569.
94. Blum J S, Wearsch P A, Cresswell P. Pathways of antigen processing. Annu Rev Immunol. 2013; 31:443-473.
95. Jordan M A, Wilson L. Microtubules as a target for anticancer drugs. Microtubules as a target for anticancer drugs. Nat Rev Cancer 2004; 4:253-265.
96. Magidson V, He J, Ault J G, O'Connell C B, Yang N, Tikhonenko I, et al. Unattached kinetochores rather than intrakinetochore tension arrest mitosis in taxol-treated cells. J Cell Biol. 2016; 212:307-319.
97. Armstrong D K, Bundy B, Wenzel L, Huang H Q, Baergen R, Lele S, et al. Intraperitoneal cisplatin and paclitaxel in ovarian cancer. N Engl J Med. 2006; 354: 34-43.
98. Ansaloni L, Coccolini F, Morosi L, Ballerini A, Ceresoli M, Grosso G, et al. Pharmacokinetics of concomitant cisplatin and paclitaxel administered by hyperthermic intraperitoneal chemotherapy to patients with peritoneal carcinomatosis from epithelial ovarian cancer. Brit J Cancer 2015; 112:306-312.
99. Sparreboom A, van Tellingen, O, Nooijen W J, Beijnen J H. Tissue distribution, metabolism and excretion of paclitaxel in mice. Anti-Cancer Drugs 1996; 7:78-86. PMID: 8742102
100. Intlekofer A M, Thompson C B. At the bench: preclinical rationale for CTLA-4 and PD-1 blockade as cancer immunotherapy. J Leukoc Biol. 2013; 94:25-39.
101. Mittica G, Genta S, Aglietta M, Valabrega G. Immune checkpoint inhibitors: a new opportunity in the treatment of ovarian cancer? Int J Molec Sci. 2016; 17:1169; doi:10.3390/ijm517071169.
102. Duraiswamy J, Kaluza K M, Freeman G J, Coukos G. Dual blockade of PD-1 and CTLA-4 combined with tumor vaccine effectively restores T-cell rejection function in tumors. Cancer Res. 2013; 73:3591-3603.
103. Duraiswamy J, Freeman G J, Coukos G. Therapeutic PD-1 pathway blockade augments with other modalities of immunotherapy T-cell function to prevent immune decline in ovarian cancer. Cancer Res. 2013; 73 6900-6912.
104. Hamanishi J, Mandai M, Konishi I. Immune checkpoint inhibition in ovarian cancer. Internat Immunol. 2016; 28:339-348.
105. Blaszczyk M, Kurcinski M, Kouza M, Wieteska L, Debinski A, Kolinski A, Kmiecik S. Modeling of protein- 106. Biasini M, Bienert S, Waterhouse A, Arnold K, Studer G, Schmidt T, et al. SWISS-MODEL: modelling protein tertiary and quaternary structure using evolutionary information. Nucleic Acids Res. 2014; 42(W1):W252-W258; doi: 10.1093/nar/gku340.

107. Benkert P, Biasini M, Schwede T. Toward the estimation of the absolute quality of individual protein structure models. Bioinformatics 2011; 27:343-350.

108. Shu C, Yi G, Watts T, Kao C C, Li P. Structure of STING bound to cyclic di-GMP reveals the mechanism of cyclic dinucleotide recognition by the immune system. Nat Struct Mol Biol. 2012; 19:722-724.

109. Shang G, Zhu D, Li N, Zhang J, Zhu C, Lu D, et al. Crystal structures of STING protein reveals the basis for recognition of cyclic di-GMP. Nat Struct Mol Biol. 2012; 19:725-727.

110. Roby K F, Taylor C C, Sweetwood J P, Cheng Y, Pace J L, Tawfik O, et al. Development of a syngeneic mouse model for events related to ovarian cancer. Carcinogenesis 2000; 21:585-591.

111. Sanchez J F, Lescar J, Chazalet V, Audfray A, Gagnon J, Alvarez R, et al. Biochemical and structural analysis of *Helix pomatia* agglutinin: a hexameric lectin with a novel fold. J Biol Chem. 2006; 281:20171-20180.

112. Mammen M, Choi S-K, Whitesides G M. Polyvalent interactions in biological systems: implications for design and use of multivalent ligands and inhibitors. Angew Chem Int Ed. 1998; 37:2754-2794. DOI: 10.1002/(SICI) 1521-3773(19981102).

113. Cairo C W, Gestwicki J E, Kanai M, Kiessling L L. Control of multivalent interactions by binding epitope density. J Am Chem Soc. 2002; 124:1615-1619.

114. Dam T K, Gerken T A, Brewer C F. Thermodynamics of multivalent carbohydrate-lectin cross-linking interactions: importance of entropy in the bind and jump mechanism. Biochemistry 2009; 48:3822-3827.

115. Vasileiou Z, Barlos K, Gatos D. Convergent solid-phase and solution approaches in the synthesis of the cysteine-rich Mdm2 RING finger domain. J Pept Sci. 2009; 15:824-831.

116. de Vries S J, Rey J, Schindler C E M, Zacharias M, Tuffery P. The pepATTRACT web server for blind, large-scale peptide-protein docking. Nucleic Acids Res. 2017; 45:W361-W364.

117. Yan, C, Xu X, Zou X. Fully blind docking at the atomic level for protein-peptide complex structure prediction. Structure 2016; 24:1842-1853.

118. London N, Movshovitz-Attias D, Shueler-Furman O. The structural basis of peptide-protein binding strategies. Structure 2010; 18:188-199.

119. Trellet M, Melquiond A S J, Bonvin A M J J. A unified conformational selection and induced fit approach to protein-peptide docking. PLoS ONE 2013; 8:e58769.

120. Weis W I, Drickamer K, Hendrickson W A. Structure of a C-type mannose-binding protein complexed with an oligosaccharide. Nature 1992; 360:127-134.

121. Drickamer K. Engineering galactose-binding activity into a C-type mannose-binding protein. Nature 1992; 360:183-186.

122. Guo Y, Feinberg H, Conroy E, Mitchell D A, Alvarez R, Blixt O, et al. Structural basis for distinct ligand-binding and targeting properties of the receptors DC-SIGN and DC-SIGNR. Nat Struct Mol Biol. 2004; 11:591-598.

123. Huysamen C, Willment J A, Dennehy K M, Brown G D. CLEC9A is a novel activation C-type lectin-like receptor expressed on BDCA3$^+$ dendritic cells and a subset of monocytes. J Biol Chem. 2008; 283:16693-16701.

124. Geijtenbeek T B H, Gringhuis S I. Signalling through C-type lectin receptors: shaping immune responses. Nat Rev Immunol. 2009; 9:465-479.

125. Garcia-Vallejo J J, van Kooyk Y. Endogenous ligands for C-type lectin receptors: the true regulators of immune homeostasis. Immunol Rev. 2009; 230:22-37.

126. Pillai S, Netravali I A, Cariappa A, Mattoo H. Siglecs and immune regulation. Annu Rev Immunol. 2012; 30:357-392.

127. Macauley M S, Crocker P R, Paulson J C. Siglec-mediated regulation of immune cell function in disease. Nat Rev Immunol. 2014; 14:653-666.

128. Peach R J, Hollenbaugh D, Stamenkovic I, Aruffo A. Identification of hyaluronic acid binding sites in the extracellular domain of CD44. J Cell Biol. 1993; 122: 257-264.

129. Marcelo F, Garcia-Martin F, Matsushita T, Sardinha J, Coelho H, Oude-Vrielink A, et al. Delineating binding modes of Gal/GalNAc and structural elements of the molecular recognition of tumor-associated mucin glyco-peptides by the human macrophage galactose-type lectin. Chem Eur J. 2014; 20:16147-16155.

130. Tanaka J, Gleinich A S, Zhang Q, Whitfield R, Kempe K, Haddleton D M, et al. Specific and differential binding of N-acetylgalactosamine glycopolymers to the human macrophage galactose lectin and asialoglycoprotein receptor. Biomacromolecules 2017; 18:1624-1633.

131. Nakanishi A, Hatano N, Fujiwara Y, et al. (2017) AMP-activated protein kinase-mediated feedback phosphorylation controls the $Ca^{2+}$/calmodulin (CaM) dependence of $Ca^{2+}$/CaM-dependent protein kinase kinase (3. J Biol Chem 292:19804-19813.

132. Prantner D, Perkins D J, Vogel S N (2017) AMP-activated kinase (AMPK) promotes innate immunity and antiviral defense through modulation of Stimulator of Interferon Genes (STING) signaling. J Biol Chem 292: 292-304.

133. Festing M F W, Legg R, Eydmann T, Brammal A. Mouse strain differences in resident peritoneal cells: a flow cytometric analysis. Lab Animals 1990; 24:53-62.

134. Mombaerts P, Iacomini J, Johnson R S, Herrup K, Tonegawa S, Papaioannou V E. RAG-1-deficient mice have no mature B and T lymphocytes. Cell 1992; 68:869-877.

135. Eskander R N, Tewari K S. Emerging treatment options for management of malignant ascites in patients with ovarian cancer. Internat J Women's Health 2012; 4:395-404.

136. Ahmed N, Stenvers K L. Getting to know ovarian cancer ascites: opportunities for targeted therapy-based translational research. Front Oncol. 2013; 3: article 256; doi: 10.3389/fonc.20130.00256.

137. Hawiger D, Inaba K, Dorsett Y, Guo M, Mahnke K, Rivera M, et al. Dendritic cells induce peripheral T cell unresponsiveness under steady state conditions in vivo. J Exp Med. 2001; 194:769-779.

138. Guan H, McGuire M J, Li S, Brown K C. Peptide-targeted polyglutamic acid doxorubicin conjugates for the treatment of $\alpha_v\beta_6$-positive cancers. Bioconjugate Chem. 2008; 19:1813-1821.

139. Langer C J, Gadjeel S M, Borghaei H, Papadimitrako-poulou V A, Patnaik A, Powell S F, et al. Carboplatin and pemetrexed with or without pembrolizumab for advanced, non-squamous non-small-cell lung cancer: a randomized, phase 2 cohort of the open-label KEYNOTE-021 study. Lancet Oncol. 2016; 17:1497-1508.

What is claimed is:

1. A pharmaceutical composition, comprising:
a pharmaceutically acceptable carrier;
an anti-cancer agent; and
a therapeutic peptide, wherein the therapeutic peptide comprises:
a sequence of $X_1$-$X_2$-$X_3$-$X_4$-$X_5$-$X_6$-$X_7$-$X_8$, or
a construct having a central framework, a linker sequence, and at least two arms,
wherein each arm consists of a core sequence of $X_1$-$X_2$-$X_3$-$X_4$-$X_5$-$X_6$-$X_7$-$X_8$,
and each arm is linked to the central framework via the linker sequence,
wherein
$X_1$ is H or N,
$X_2$ is P or Q,
$X_3$ is S or H,
$X_4$ is H, T, or L,
$X_5$ is P or K,
$X_6$ is R, L, or S,
$X_7$ is S, or L, and
$X_8$ is G, and
wherein the therapeutic peptide and the anti-cancer agent are conjugated by a chemical conjugation or an enzymatic conjugation.

2. A method of reducing cancer cell proliferation, comprising contacting the cancer cell with a pharmaceutical composition in an amount sufficient to reduce cancer cell proliferation, the pharmaceutical composition comprising:
a pharmaceutically acceptable carrier;
an anti-cancer agent; and
a therapeutic peptide, wherein the therapeutic peptide comprises:
a sequence of $X_1$-$X_2$-$X_3$-$X_4$-$X_5$-$X_6$-$X_7$-$X_8$, or
a construct having a central framework, a linker sequence, and at least two arms,
wherein each arm consists of a core sequence of $X_1$-$X_2$-$X_3$-$X_4$-$X_5$-$X_6$-$X_7$-$X_8$,
and each arm is linked to the central framework via the linker sequence,
wherein
$X_1$ is H or N,
$X_2$ is P or Q,
$X_3$ is S or H,
$X_4$ is H, T, or L,
$X_5$ is P or K,
$X_6$ is R, L, or S,
$X_7$ is S, or L, and
$X_8$ is G,
wherein the pharmaceutical composition further comprises a second therapeutic peptide, and
wherein
the anti-cancer agent comprises cyclic dinucleotide (CDN),
the second therapeutic peptide comprises a construct having a central framework,
a linker sequence, and four arms, each arm consisting of a core sequence of NQHTPR (SEQ ID NO: 1) and is linked to the central framework via the linker sequence, and
the second therapeutic peptide and CDN are conjugated via a linker.

3. A method of treating cancer in a subject in need thereof, comprising administering to the subject in an amount sufficient to slow cancer progression in the subject,
an anti-cancer agent; and
a therapeutic peptide, wherein the therapeutic peptide comprises:
a sequence of $X_1$-$X_2$-$X_3$-$X_4$-$X_5$-$X_6$-$X_7$-$X_8$, or
a construct having a central framework, a linker sequence, and at least two arms,
wherein each arm consists of a core sequence of $X_1$-$X_2$-$X_3$-$X_4$-$X_5$-$X_6$-$X_7$-$X_8$,
and each arm is linked to the central framework via the linker sequence,
wherein
$X_1$ is H or N,
$X_2$ is P or Q,
$X_3$ is S or H,
$X_4$ is H, T, or L,
$X_5$ is P or K,
$X_6$ is R, L, or S,
$X_7$ is S, or L, and
$X_8$ is G, and
wherein the administration of the anti-cancer agent precedes the administration of the therapeutic peptide by at least 1 day.

4. The pharmaceutical composition of claim 1, wherein $X_1$ is N, $X_2$ is P, $X_3$ is S, $X_4$ is H, $X_5$ is P, $X_6$ is L, $X_7$ is S, and $X_8$ is G.

5. The pharmaceutical composition of claim 1, wherein the pharmaceutical composition further comprises a second therapeutic peptide comprising
a sequence of NQHTPR (SEQ ID NO: 1), or
a construct having a central framework, a linker sequence, and at least two arms, wherein
each arm consists of a core sequence of NQHTPR (SEQ ID NO:1), and each arm is linked to the central framework via the linker sequence.

6. The pharmaceutical composition of claim 1, wherein the construct comprises a tri-lysine central framework and four arms, and at least one linker sequence is selected from the group consisting of: GGGS (SEQ ID NO: 3), GGGSGGGS (SEQ ID NO: 4), SSSS (SEQ ID NO: 5), and SSSSSSSS (SEQ ID NO: 6).

7. The pharmaceutical composition of claim 1, wherein the therapeutic peptide is in an amount sufficient to trigger endocytosis of Ca'-dependent lectin-type receptor family member 10A (CLEC10A) into a cell.

8. The pharmaceutical composition of claim 1, wherein the therapeutic peptide is in an amount sufficient to increase a peritoneal immune cell population selected from the group consisting of: T cells expressing CD3; activated natural killer T (NKT) cells expressing CD3, NK1.1, and CD69; activated natural killer (NK) cells expressing CD3, NK1.1, and CD69; T cells expressing CD4; activated T cells expressing CD4 and CD69; cytotoxic T cells expressing CD8; activated cytotoxic T cells expressing CD8 and CD69; mature, active macrophages expressing CD11b, F4/80, and CD86; dendritic cells (DCs) expressing CD11c; activated DCs expressing CD11c and CD86; B cells expressing CD19; memory B cells expressing CD19, CD73, CD80, and CD273; and combinations thereof.

9. The pharmaceutical composition of claim 1, wherein the therapeutic peptide is in an amount sufficient to induce release of IFN-γ.

10. The pharmaceutical composition of claim 1, wherein the anti-cancer agent is selected from the group consisting of: a chemotherapy drug, a cancer immunotherapy drug, a photosensitizer, and combinations thereof.

11. The pharmaceutical composition of claim 1, wherein the anti-cancer agent and the therapeutic peptide are present in an average molar ratio of between 10:1 and 12:1.

12. The method of claim 2, wherein the cancer cell expresses CLEC10A, ASGPR-1, CLEC4F, or combinations thereof.

13. The method of claim 2, wherein the cancer is selected from the group consisting of: bladder cancer, breast cancer, cervical cancer, hepatocellular carcinoma, Kaposi sarcoma, lung cancer, lymphoma, malignant melanoma, melanoma, mesothelioma, metastatic melanoma lung cancer, non-small cell lung cancer, ovarian cancer, pancreatic cancer, prostate cancer, peritoneal cancer, renal cell cancer, small-cell lung cancer, and squamous lung cancer.

14. The method of claim 3, wherein the amount of the therapeutic peptide is within the range of 1 nmol to 1,000 nmol per kg of body weight of the subject.

15. The method of claim 3, wherein the therapeutic peptide is not antigenic in the subject.

16. The pharmaceutical composition of claim 5, wherein the second therapeutic peptide comprises a sequence of VQATQSNQHTPR (SEQ ID NO: 2) or a construct having a central framework, a linker sequence, and at least two arms, wherein at least one arm comprises VQATQSNQHTPR (SEQ ID NO: 2), and each arm is linked to the central framework via the linker sequence.

17. The method of claim 2, wherein $X_1$ is N, $X_2$ is P, $X_3$ is S, $X_4$ is H, $X_5$ is P, $X_6$ is L, $X_7$ is S, and $X_8$ is G.

18. The method of claim 3, wherein $X_1$ is N, $X_2$ is P, $X_3$ is S, $X_4$ is H, $X_5$ is P, $X_6$ is L, $X_7$ is S, and $X_8$ is G.

19. The method of claim 3, wherein the anti-cancer agent is selected from the group consisting of: a chemotherapy drug, a cancer immunotherapy drug, a photosensitizer, and combinations thereof.

20. The method of claim 3, wherein the cancer is selected from the group consisting of: bladder cancer, breast cancer, cervical cancer, hepatocellular carcinoma, Kaposi sarcoma, lung cancer, lymphoma, malignant melanoma, melanoma, mesothelioma, metastatic melanoma lung cancer, non-small cell lung cancer, ovarian cancer, pancreatic cancer, prostate cancer, peritoneal cancer, renal cell cancer, small-cell lung cancer, and squamous lung cancer.

* * * * *